United States Patent
Hayoz et al.

(10) Patent No.: US 9,067,942 B2
(45) Date of Patent: Jun. 30, 2015

(54) PYRROLOPYRROLE DERIVATIVES, THEIR MANUFACTURE AND USE AS SEMICONDUCTORS

(75) Inventors: Pascal Hayoz, Hofstetten (CH); Olivier Frederic Aebischer, Duedingen (CH); Mathias Dueggeli, Thuernen (CH); Mathieu G. R. Turbiez, Rixheim (FR); Marta Fonrodona Turon, Blanes (ES); Natalia Chebotareva, Hagenthal le Bas (FR)

(73) Assignee: BASF SE, Ludwigshafen (DE)

( * ) Notice: Subject to any disclaimer, the term of this patent is extended or adjusted under 35 U.S.C. 154(b) by 150 days.

(21) Appl. No.: 13/260,002

(22) PCT Filed: Mar. 30, 2010

(86) PCT No.: PCT/EP2010/054152
§ 371 (c)(1),
(2), (4) Date: Dec. 27, 2011

(87) PCT Pub. No.: WO2010/115767
PCT Pub. Date: Oct. 14, 2010

(65) Prior Publication Data
US 2012/0095236 A1    Apr. 19, 2012

(30) Foreign Application Priority Data

Apr. 8, 2009  (EP) .................................. 09157579
Aug. 24, 2009 (EP) .................................. 09168454

(51) Int. Cl.
| | | |
|---|---|---|
| C07D 417/14 | (2006.01) | |
| H01L 29/02 | (2006.01) | |
| C07D 487/04 | (2006.01) | |
| H01L 51/00 | (2006.01) | |

(52) U.S. Cl.
CPC .......... *C07D 487/04* (2013.01); *H01L 51/0053* (2013.01); *H01L 51/0068* (2013.01); *H01L 51/0069* (2013.01); *Y02E 10/549* (2013.01)

(58) Field of Classification Search
CPC .............................. C07D 417/14; H01L 29/02
USPC ............................................ 548/181; 257/40
See application file for complete search history.

(56) References Cited

U.S. PATENT DOCUMENTS

| | | | |
|---|---|---|---|
| 5,703,436 | A | 12/1997 | Forrest et al. |
| 6,420,031 | B1 | 7/2002 | Parthasarathy et al. |
| 2003/0021913 | A1 | 1/2003 | O'Neill et al. |
| 2004/0004433 | A1 | 1/2004 | Lamansky et al. |
| 2006/0013549 | A1 | 1/2006 | Shtein et al. |
| 2007/0079867 | A1 | 4/2007 | Chittibabu et al. |
| 2007/0228359 | A1 | 10/2007 | Heim et al. |
| 2009/0302311 | A1 | 12/2009 | Turbiez et al. |

FOREIGN PATENT DOCUMENTS

| | | |
|---|---|---|
| JP | 2006 117591 | 5/2006 |
| JP | 2007 266285 | 10/2007 |
| JP | 2007-266285 | * 10/2007 |
| WO | 2004 090046 | 10/2004 |
| WO | 2004 112161 | 12/2004 |
| WO | 2005 049695 | 6/2005 |
| WO | 2008 000664 | 1/2008 |
| WO | 2008 001123 | 1/2008 |
| WO | WO-2008000664 | * 3/2008 |
| WO | 2009 047104 | 4/2009 |
| WO | 2010 049321 | 5/2010 |
| WO | 2010 049323 | 5/2010 |

OTHER PUBLICATIONS

U.S. Appl. No. 13/246,003, filed 2011 and U.S. Appl. No. 12/680,904, filed 2010.*
STN display: Turbiez et al., WO 2008/000664 (2008), STN display Tamayo et al., Journal of Physical Chemistry C, (2008), 112(39), 15543-15552.*
STN display: Advanced Materials (Weinheim, Germany) (2008), 20(11), 2217-2224, Burgi et al., STN display: Ikeda et al., JP 2007266285 (2007).*
STN display: Suda et al., JP 2006117591 (2006).*
U.S. Appl. No. 13/322,506, filed Dec. 21, 2011, Kirner, et al.
International Search Report Issued Jun. 2, 2010 in PCT/EP10/054152 Filed Mar. 30, 2010.
U.S. Appl. No. 13/246,003, filed Sep. 27, 2011, Wuerthner, et al.
Mananya Tantiwiwat, et al. "Oligothiophene Derivatives Functionalized with a Diketopyrrolopyrrolo Core for Solution-Processed Field Effect Transistors, etc." J. Phys. Chem. C, vol. 112, No. 44, 2008, pp. 17402-17407.
U.S. Appl. No. 14/385,696, filed Sep. 16, 2014, Welker, et al.
U.S. Appl. No. 14/386,123, filed Sep. 18, 2014, Hayoz.

* cited by examiner

*Primary Examiner* — Yong Chu
*Assistant Examiner* — Sonya Wright
(74) *Attorney, Agent, or Firm* — Oblon, McClelland, Maier & Neustadt, L.L.P.

(57) ABSTRACT

The present invention relates to compounds of the formula (I) wherein the substituents are as defined in claim 1, and their use as organic semiconductor in organic devices, like diodes, organic field effect transistors and/or solar cells. The compounds of the formula I have excellent solubility in organic solvents. High efficiency of energy conversion, excellent field-effect mobility, good on/off current ratios and/or excellent stability can be observed, when said compounds are used in semiconductor devices or organic photovoltaic (PV) devices (solar cells).

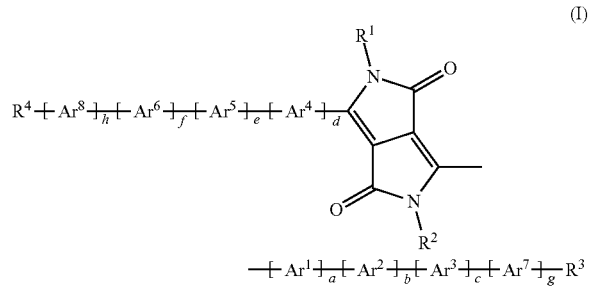

16 Claims, No Drawings

PYRROLOPYRROLE DERIVATIVES, THEIR MANUFACTURE AND USE AS SEMICONDUCTORS

The present invention relates to 1,4-diketopyrrolo[3,4-c] pyrrole (DPP) derivatives of the below formula I, wherein the substituents are as defined herein below, to their manufacture; to their use as organic semiconductors, e.g. in semiconductor devices, especially a sensor, a diode, a photodiode, an organic field effect transistor, a transistor for flexible displays, and/or a solar cell (photovoltaic cell); to such semiconductor devices comprising diketopyrrolopyrrol derivatives of the formula I as a semiconducting effective means, and to devices containing said semiconductor devices.

JP2006117591(A) to Toyo Ink Manufacturing Co. discloses diketopyrrolopyrrol derivatives for use in organic electroluminescent elements, like flat panel displays and liquid crystal displays, but not for use as organic semiconductors.

JP2007266285(A) relates to a field effect transistor comprising a compound represented by a formula

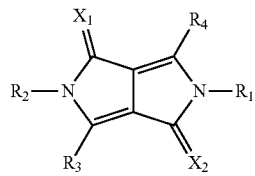

as a semiconductor material, wherein $X_1$ and $X_2$ each independently denote an oxygen atom, a sulfur atom, or a selenium atom, and $R_1$, $R_2$, $R_3$ and $R_4$ each independently denote a hydrogen atom, a substitutable aliphatic hydrocarbon group, or a substitutable aromatic group.

WO2004/090046 A1 to Ciba discloses fluorescent diketopyrrolopyrrol (DPP) derivatives, mainly for use in inks, toners, colorants, pigmented plastics, color changing media, solid dye lasers and electroluminescent devices. Said DPP derivatives have a smaller or shorter side chain on both sides of the diketopyrrolopyrrol moiety than the diketopyrrolopyrrol derivatives claimed per se in the present specification. In addition, specifically disclosed, i.e. individualized, compounds include only those derivatives wherein the DPP nitrogen atoms are substituted by alkyl groups having no more than 5 carbon atoms. As has been found by the present invention, for the overall efficiency of photovoltaic cells the number of carbon atoms in each of the alkyl substituents on the DPP nitrogen atoms is of major importance and should be at least 7, preferably at least 10.

WO05/049695 discloses polymers comprising a repeating unit of the formula

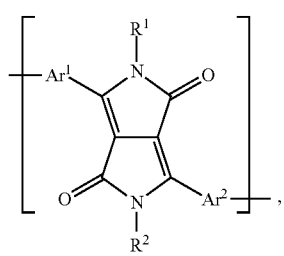
(I)

wherein $Ar^1$ and $Ar^2$ are preferably selected from

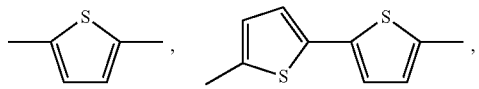

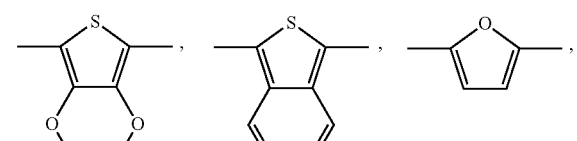

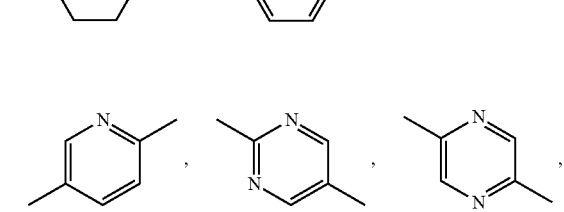

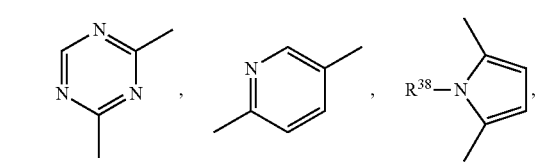

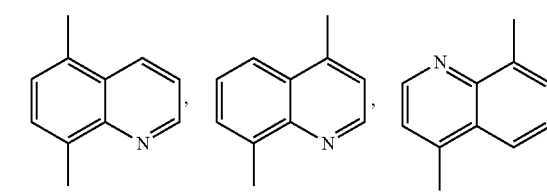

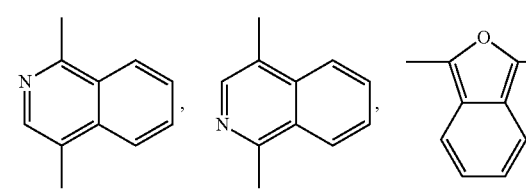

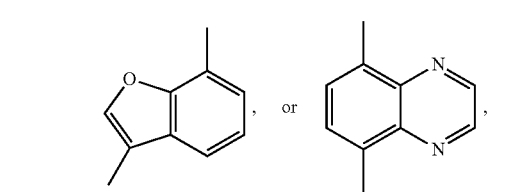

wherein $R^{38}$ stands for hydrogen, $C_6$-$C_{10}$aryl, $C_7$-$C_{12}$alkylaryl, $C_7$-$C_{12}$aralkyl, or $C_1$-$C_8$-alkyl.

WO08/000,664 relates to polymers comprising a repeating unit of the formula

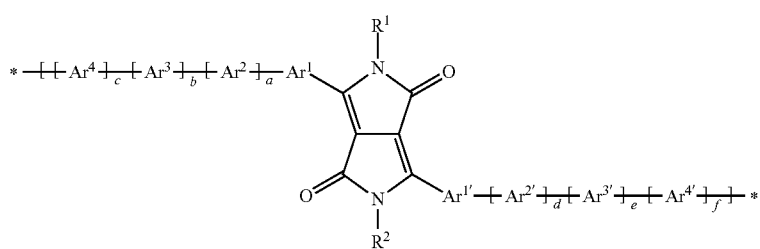
(I)

and their use as organic semiconductor in organic devices, especially a diode, an organic field effect transistor and/or a solar cell, or a device containing a diode and/or an organic field effect transistor, and/or a solar cell.

WO09/047,104 discloses compounds of the formula

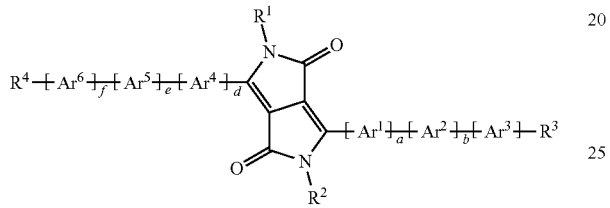

wherein $R^1$ and $R^2$ are independently of each other an aliphatic, cycloaliphatic, cycloaliphatic-aliphatic, aromatic, aromatic-aliphatic, heteroaromatic or heteroaromatic-aliphatic group having up to 49 carbon atoms, a and d independently of each other are 0, 1, 2 or 3, $Ar^1$ and $Ar^4$ are independently of each other a bivalent group of the formula

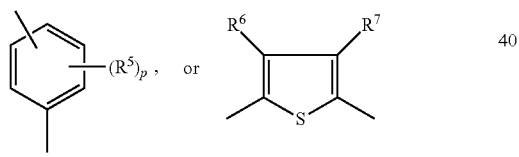

wherein $R^6$ and $R^7$ are as defined below, p represents 0, 1, or 2, $R^5$ is an aliphatic hydrocarbon group having up to 25 carbon atoms, or two vicinal groups $R^5$ together represent alkylene or alkenylene having up to 7 carbon atoms, it being possible that two groups $R^5$ present in the group of formula II differ from each other, b, c, e, and f independently of each other represent 1, 2 or 3, $Ar^2$, $Ar^3$, $Ar^5$, and $Ar^6$ are independently of each other a bivalent group of one of the formulae IV to X and L,

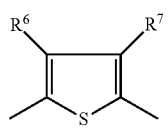
(IV)

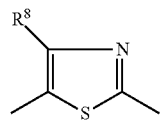
(V)

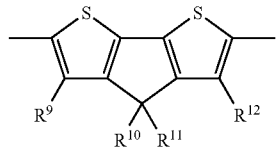
(VI)

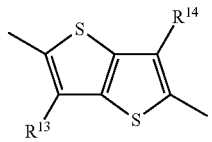
(VII)

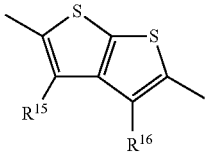
(VIII)

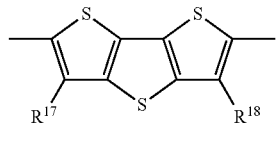
(IX)

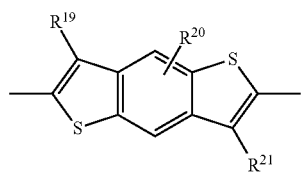
(X)

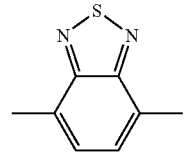
(L)

wherein $R^6$, $R^7$, $R^8$, $R^9$, $R^{12}$, $R^{13}$, $R^{15}$, $R^{16}$, $R^{17}$, $R^{18}$, $R^{19}$, $R^{20}$ and $R^{21}$ are independently of each other hydrogen, $C_1$-$C_{25}$alkyl, $C_1$-$C_{18}$alkoxy, $C_6$-$C_{24}$aryl, $C_7$-$C_{25}$aralkyl, or heteroaryl, or $R^6$ and $R^7$ together represent alkylene or alkenylene which may be both bonded via oxygen and/or sulfur to the thienyl residue and which may both have up to 25 carbon atoms, $R^{10}$ and $R^{11}$ are independently of each other hydrogen, $C_1$-$C_{18}$alkyl, $C_6$-$C_{24}$aryl, heteroaryl, or $R^{10}$ and $R^{11}$ together represent oxo or form a five or six membered ring, which is unsubstituted or substituted by a) an aliphatic hydrocarbon group having up to 18 carbon atoms, b) $C_1$-$C_{18}$alkoxy or $C_2$-$C_{18}$alkylenedioxy in both of which carbon atoms which are not adjacent to oxygen may be replaced by oxygen, or c) $C_6$-$C_{24}$aryl, $C_7$-$C_{25}$aralkyl, heteroaryl, $C_3$-$C_{12}$cycloalkyl or $C_4$-$C_{12}$cycloalkyl-alkyl, and $R^3$ and $R^4$ are independently of each other a group of one of the formulae XI to XIX,

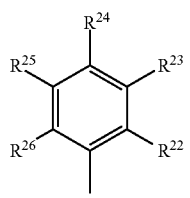
(XI)

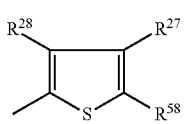
(XII)

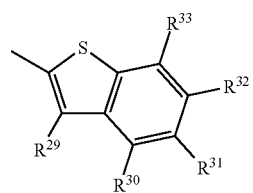
(XIII)

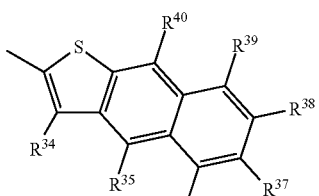
(XIV)

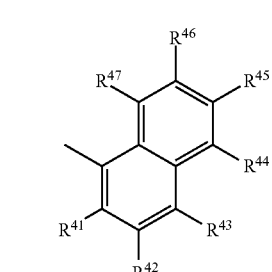
(XV)

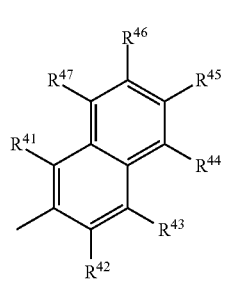
(XVI)

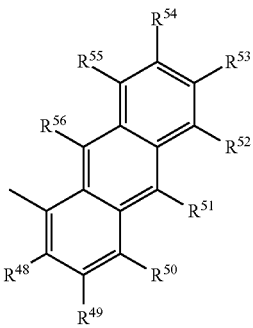
(XVII)

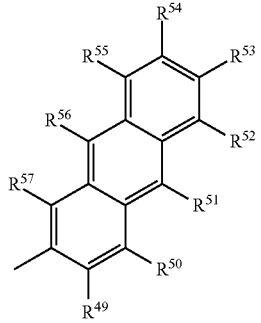
(XVIII)

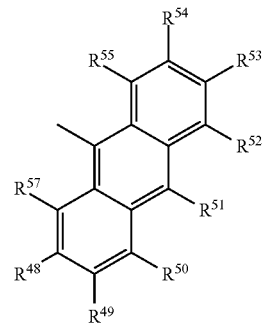
(XIX)

wherein $R^{22}$ to $R^{26}$ and $R^{29}$ to $R^{58}$ represent independently of each other hydrogen, an aliphatic hydrocarbon group having up to 25 carbon atoms, alkoxy or alkenyloxy having up to 18 carbon atoms, halogen, a cycloaliphatic, cycloaliphatic-aliphatic, aromatic, aromatic-aliphatic, heteroaromatic or heteroaromatic-aliphatic group having up to 25 carbon atoms, or a group of the formula (III)

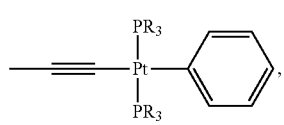
(III)

wherein R represents an aliphatic hydrocarbon group having up to 12 carbon atoms, or two groups $R^{22}$ to $R^{26}$ and $R^{29}$ to $R^{57}$ which are in the neighborhood of each other, together represent alkylene or alkenylene having up to 8 carbon atoms, thereby forming a ring, and $R^{27}$ and $R^{28}$ are independently of each other hydrogen, $C_1$-$C_{25}$alkyl, $C_1$-$C_{18}$alkoxy, $C_6$-$C_{24}$aryl, $C_7$-$C_{25}$aralkyl, heteroaryl, or a group of the formula (III) shown above, wherein R represents an aliphatic hydrocarbon group having up to 12 carbon atoms, or $R^{27}$ and $R^{28}$ together or $R^{27}$ and $R^{58}$ together represent alkylene or alkenylene which may be both bonded via oxygen and/or sulfur to the thienyl residue and which may both have up to 25 carbon atoms.

It has surprisingly been found that certain monomeric diketopyrrolopyrrol derivatives, especially those having longer side chains, can be used as organic semiconductors. Said derivatives have excellent solubility in non-halogenated organic solvents (allowing easy handling). They can be synthesized easier than polymers (allowing cost savings), and they are easy to purify (allowing very pure products to be obtained at low cost).

For semiconducting devices, like solar cells, the power conversion efficiency (PCE), i.e. the percentage of power converted from absorbed light to electrical energy, is decisive. While silicon based solar cells reach already a PCE of up to 20%, the PCE of solar cells based on organic semiconductors is still much lower, i.e. in the range of 5% for polymeric semiconductors. For monomeric, i.e. small molecule based semiconductors the PCE, as reported before the priority date of the present invention, is even lower than for polymeric semiconductors. Solution processed solar cells so far were reaching a PCE just up to about 1.3%.

Despite the lower PCE attained thus far, small molecules potentially offer several advantages over polymer and silicon based materials. With respect to silicon based materials said advantages include lower cost fabrication by solution processing, lightweight and compatibility with flexible substrates. With respect to polymeric materials small molecules do not suffer from batch to batch variations, broad molecular weight distributions, end group contamination, and difficult purification methods. Furthermore, small molecules may display higher hole and electron mobilities than their polymeric analogues, presumably as a result of better molecular ordering.

The object of the present invention was the identification of small molecules with improved PCE, high field effect mobility (charge carrier mobility), high on/off current ratio, and low threshold voltage. A high on/off current ratio is especially useful for an organic field effect transistor (OFET).

The invention relates especially to diketopyrrolopyrrol (DPP) derivatives of the formula

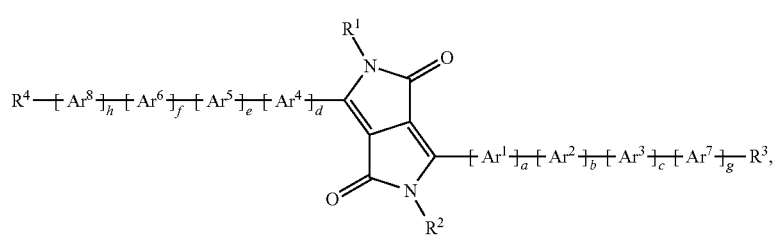

(I)

wherein $R^1$ and $R^2$ may be the same or different and are selected from hydrogen, a $C_1$-$C_{100}$alkyl group, —COOR$^{103}$, a $C_1$-$C_{100}$alkyl group which is substituted by one or more halogen atoms, hydroxyl groups, nitro groups, —CN, or $C_6$-$C_{24}$aryl groups and/or interrupted by —O—, —COO—, —OCO—, or —S—; a $C_7$-$C_{100}$arylalkyl group, a carbamoyl group, $C_5$-$C_{12}$cycloalkyl, which can be substituted one to three times with $C_1$-$C_8$alkyl and/or $C_1$-$C_8$alkoxy, a $C_6$-$C_{24}$aryl group, in particular phenyl or 1- or 2-naphthyl which can be substituted one to three times with $C_1$-$C_8$alkyl, $C_1$-$C_8$thioalkoxy, and/or $C_1$-$C_8$alkoxy, or pentafluorophenyl, $R^{103}$ is H; $C_6$-$C_{24}$aryl; $C_6$-$C_{24}$aryl which is substituted by $C_1$-$C_{25}$alkyl, or $C_1$-$C_{25}$alkoxy; $C_1$-$C_{50}$alkyl; or $C_1$-$C_{50}$alkyl which is interrupted by —O—, especially $C_4$-$C_{25}$alkyl;

a is 1, 2 or 3, and d is 0, 1, 2 or 3, with the proviso that e is not 0, if d is 0, $Ar^1$ and $Ar^4$ are independently of each other a bivalent group of the formula

(II)

wherein
one of $X^3$ and $X^4$ is N and the other is $CR^{100}$, or an annulated (aromatic) heterocyclic ring system, containing at least one thiazole ring, which may be optionally substituted by one, or more groups, $R^{100}$ is hydrogen, $C_1$-$C_{25}$alkyl, $C_1$-$C_{18}$alkoxy, $C_6$-$C_{24}$aryl, $C_7$-$C_{25}$aralkyl, or heteroaryl, b, c, e, f, g and h independently of each other represent 0, 1, 2 or 3, $Ar^2$, $Ar^3$, $Ar^5$, $Ar^6$, $Ar^7$ and $Ar^8$ have the meaning of $Ar^1$, or are independently of each other a group of one of the formulae

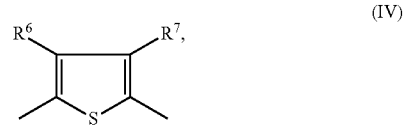

(IV)

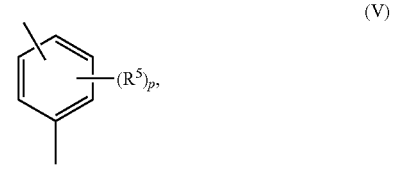

(V)

-continued

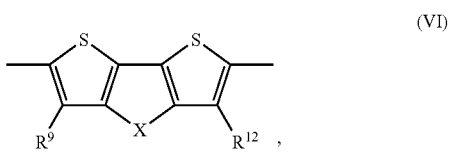

(VI)

-continued

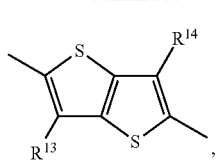
(VII)

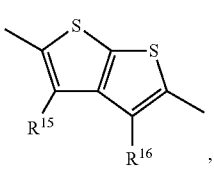
(VIII)

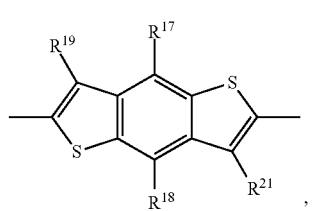
(IX)

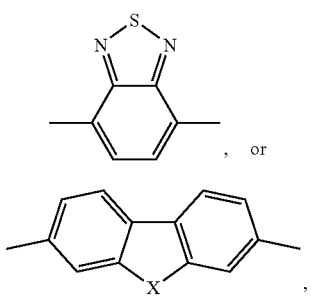
(Xa)

or

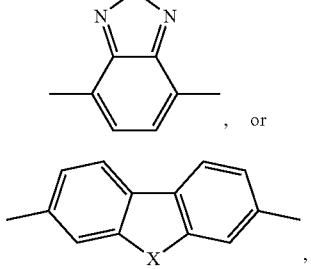
(Xb)

wherein
X is >SiR$^{60}$R$^{61}$, >NR$^{62}$, >CR$^{10}$R$^{11}$, —S—, or —O—,
p represents 0, 1, or 2,
R$^5$ is an aliphatic hydrocarbon group having up to 25 carbon atoms, C$_1$-C$_{25}$alkoxy, or two vicinal groups R$^5$ together represent alkylene or alkenylene having up to 7 carbon atoms, it being possible that two groups R$^5$ present in the group of formula V differ from each other,
R$^6$, R$^7$, R$^9$, R$^{12}$, R$^{13}$, R$^{14}$, R$^{15}$, R$^{16}$, R$^{17}$, R$^{18}$, R$^{19}$, and R$^{21}$ are independently of each other hydrogen, C$_1$-C$_{25}$alkyl, C$_1$-C$_{25}$alkoxy, C$_6$-C$_{24}$aryl, C$_7$-C$_{25}$aralkyl, or heteroaryl, or R$^6$ and R$^7$ together represent alkylene or alkenylene which may be both bonded via oxygen and/or sulfur to the thienyl residue and which may both have up to 25 carbon atoms,
R$^{10}$ and R$^{11}$ are independently of each other hydrogen, C$_1$-C$_{25}$alkyl, C$_7$-C$_{25}$aralkyl, C$_6$-C$_{24}$aryl, heteroaryl, or R$^{10}$ and R$^{11}$ together represent oxo or form a five or six membered ring, which is unsubstituted or substituted by
a) an aliphatic hydrocarbon group having up to 18 carbon atoms,
b) C$_1$-C$_{18}$alkoxy or C$_2$-C$_{18}$alkylenedioxy in both of which carbon atoms which are not adjacent to oxygen may be replaced by oxygen, or
c) C$_6$-C$_{24}$aryl, C$_7$-C$_{25}$aralkyl, heteroaryl, C$_3$-C$_{12}$cycloalkyl or C$_4$-C$_{12}$cycloalkyl-alkyl, and
R$^{60}$ and R$^{61}$ are independently of each other hydrogen, C$_1$-C$_{25}$alkyl, phenyl, especially C$_1$-C$_{12}$alkyl,
R$^{62}$ is hydrogen, C$_7$-C$_{25}$arylalkyl, C$_6$-C$_{24}$aryl; C$_6$-C$_{24}$aryl which is substituted by C$_1$-C$_{25}$alkyl, C$_1$-C$_{25}$ perfluoroalkyl, or C$_1$-C$_{25}$alkoxy; C$_1$-C$_{25}$alkyl; C$_1$-C$_{25}$alkyl, C$_1$-C$_{25}$alkyl which is interrupted by —O—, or —S—; or —COOR$^{103}$; especially C$_1$-C$_{25}$alkyl;

R$^3$ and R$^4$ are independently of each other hydrogen, an aliphatic hydrocarbon group having up to 25 carbon atoms, alkoxy or alkenyloxy having up to 25 carbon atoms, halogen, a cycloaliphatic, cycloaliphatic-aliphatic, aromatic, aromatic-aliphatic, heteroaromatic or heteroaromatic-aliphatic group having up to 25 carbon atoms, or a group of one of the formulae

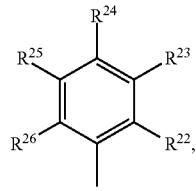
(XI)

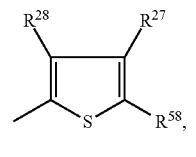
(XII)

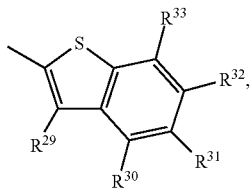
(XIII)

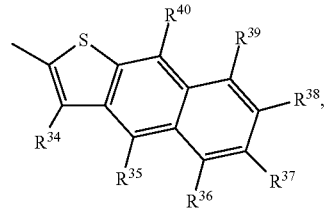
(XIV)

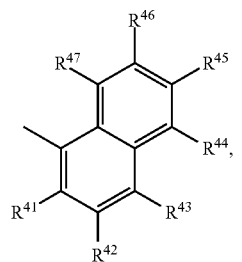
(XV)

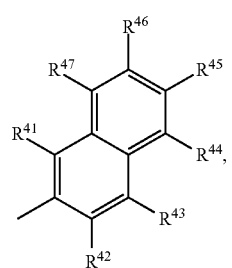
(XVI)

-continued

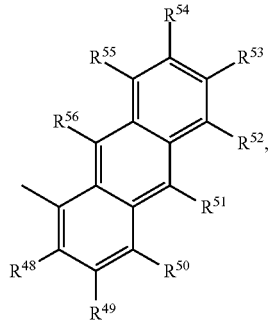
(XVII)

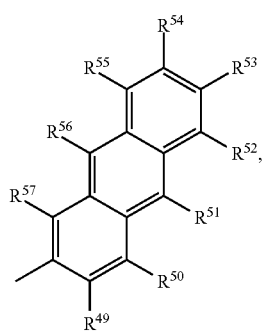
(XVIII)

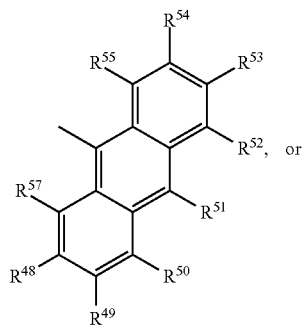
(XIX)

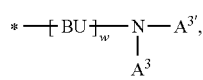
(XX)

wherein w is 0, or 1, BU is a bridging unit and $A^3$ and $A^{3'}$ are independently of each other a $C_6$-$C_{24}$aryl group, or a $C_2$-$C_{26}$heteroaryl group, which can optionally be substituted, $R^{22}$ to $R^{58}$ represent independently of each other hydrogen, an aliphatic hydrocarbon group having up to 25 carbon atoms, alkoxy or alkenyloxy having up to 25 carbon atoms, halogen, a cycloaliphatic, cycloaliphatic-aliphatic, aromatic, aromatic-aliphatic, heteroaromatic or heteroaromatic-aliphatic group having up to 25 carbon atoms, or
$R^{27}$ and $R^{28}$, or $R^{27}$ and $R^{58}$ together represent alkylene or alkenylene which may be both bonded via oxygen and/or sulfur to the thienyl residue and which may both have up to 25 carbon atoms, with the proviso that the following compound

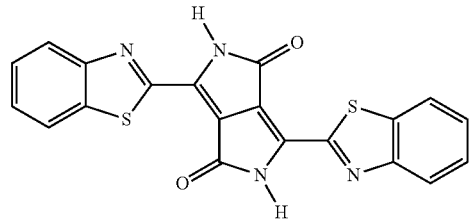 [SMILES: O=C1NC(c2nc3ccccc3s2)=C2C(=O)NC(c3nc4ccccc4s3)=C12]

is excluded.

Examples of an annulated (aromatic) heterocyclic ring system, containing at least one thiazole ring, which may be optionally substituted by one, or more groups, are shown below:

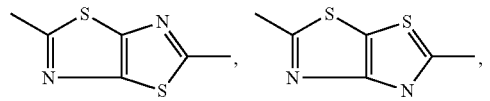

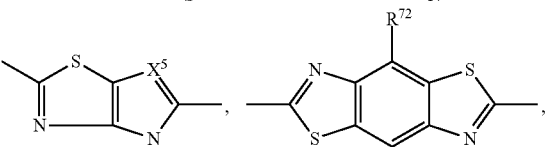

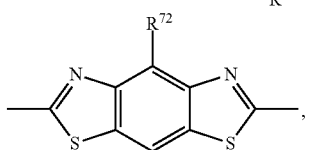

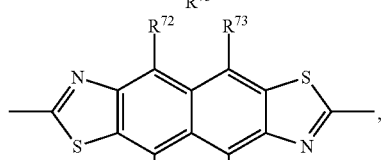

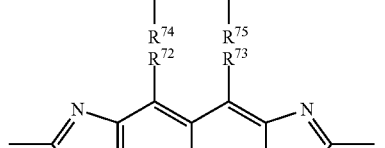

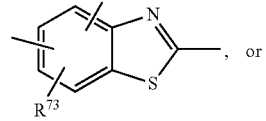

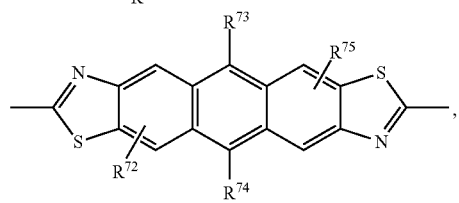

wherein $R^{72}$, $R^{73}$, $R^{74}$ and $R^{75}$ represent independently of each other hydrogen, an aliphatic hydrocarbon group having up to 25 carbon atoms, alkoxy or alkenyloxy having up to 18 carbon atoms, halogen, a cycloaliphatic, cycloaliphatic-aliphatic, aromatic, aromatic-aliphatic, heteroaromatic or heteroaromatic-aliphatic group having up to 25 carbon atoms, and $X^5$ is N, or $CR^{100}$, $R^{100}$ is hydrogen, or $C_1$-$C_{25}$alkyl.

$Ar^1$ is preferably

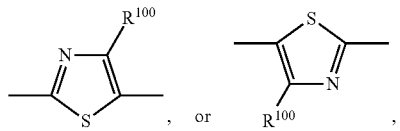

especially

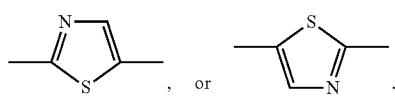

$Ar^4$ is preferably

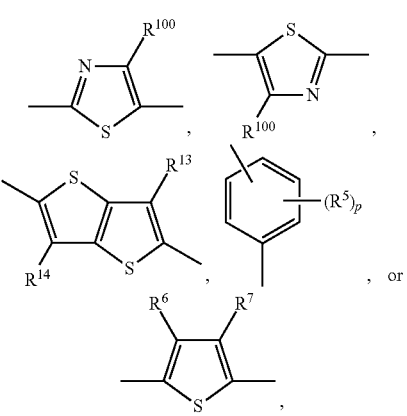

especially

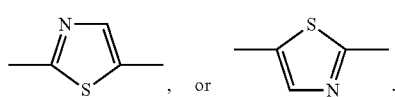

$Ar^2$, $Ar^3$, $Ar^5$, $Ar^6$, $Ar^7$ and $Ar^8$ are preferably

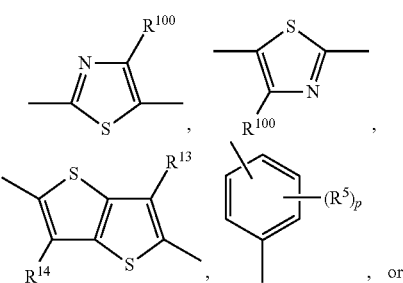

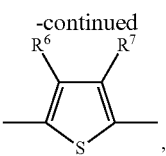

more preferably

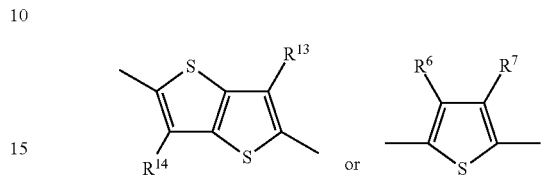

and most preferably

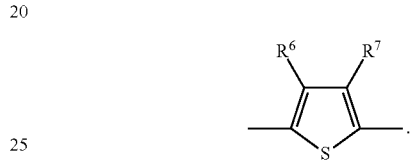

$R^{100}$ is hydrogen, $C_7$-$C_{25}$aralkyl, or $C_1$-$C_{25}$alkyl; $R^5$ is $C_1$-$C_{25}$alkyl; $R^6$, $R^7$, $R^{13}$ and $R^{14}$ are independently of each other hydrogen, $C_7$-$C_{25}$aralkyl, or $C_1$-$C_{25}$alkyl; and p is 0, 1, or 2.

$R^1$ and $R^2$ can be hydrogen, but are preferably different from hydrogen.

$R^1$ and $R^2$ can be different, but are preferably the same. Preferably, $R^1$ and $R^2$ independently from each other stand for $C_1$-$C_{100}$alkyl, $C_5$-$C_{12}$cycloalkyl, which can be substituted one to three times with $C_1$-$C_8$alkyl and/or $C_1$-$C_8$alkoxy, phenyl or 1- or 2-naphthyl which can be substituted one to three times with $C_1$-$C_8$alkyl and/or $C_1$-$C_8$alkoxy, or —$CR^{203}R^{204}$—$(CH_2)_u$—Ar, wherein $R^{203}$ and $R^{204}$ stand for hydrogen, or $C_1$-$C_4$alkyl, Ar stands for phenyl or 1- or 2-naphthyl, which can be substituted one to three times with $C_1$-$C_8$alkyl and/or $C_1$-$C_8$alkoxy, and u stands for 0, 1, 2 or 3.

$R^1$ and $R^2$ are more preferably a $C_1$-$C_{36}$alkyl group, such as n-dodecyl, tridecyl, tetradecyl, pentadecyl, hexadecyl, 2-ethyl-hexyl, 2-butyl-hexyl, 2-butyl-octyl, 2-hexyldecyl, 2-decyl-tetradecyl, heptadecyl, octadecyl, eicosyl, heneicosyl, docosyl, or tetracosyl. In a particularly preferred embodiment of the present invention $R^1$ and $R^2$ are a 2-hexyldecyl, or 2-decyl-tetradecyl group.

Advantageously, the groups $R^1$ and $R^2$ can be represented by formula

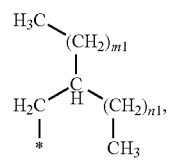

wherein $m1=n1+2$ and $m1+n1 \leq 24$. Chiral side chains, such as $R^1$ and $R^2$, can either be homochiral, or racemic, or have opposite chirality, which can influence the morphology of the compounds of formula I in the solid state.

As indicated by the formula

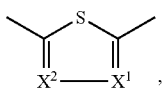

the group

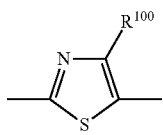

can be arranged in two ways

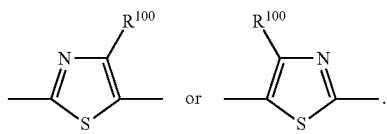

The notation

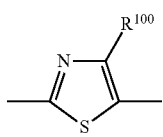

should comprise both possibilities. The same applies for other groups, which can be arranged in different ways in the compounds, monomers and/or polymers.

In one embodiment of the present invention the side chains of the formulae

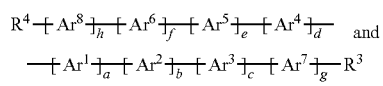

are different. In a more preferred embodiment of the present invention the side chains of the formulae

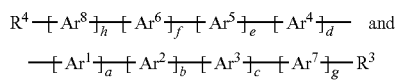

are identical to each other.
X is preferably >NR$^{62}$, >CR$^{10}$R$^{11}$, or —S—.

Compounds of the formula I are preferred, wherein
a and d represent 1,
Ar$^1$ and Ar$^4$ are a bivalent group of the formula

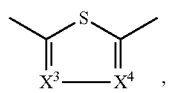

wherein one of X$^3$ and X$^4$ is N and the other is CR$^{160}$, and
R$^{100}$ is hydrogen, or C$_1$-C$_{25}$alkyl; or Ar$^1$ is a bivalent group of the formula II, and Ar$^4$ is a different bivalent group of the formula II;
or
a and e represent 1, d is 0,
Ar$^1$ is a bivalent group of the formula II, and Ar$^5$ is a different bivalent group of the formula II,

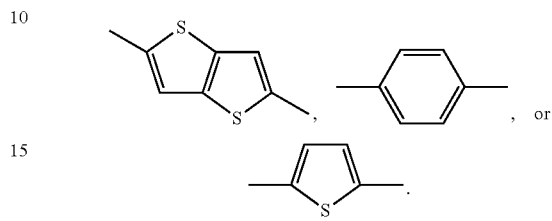

Compounds of the formula I are preferred, wherein
a and d represent 1,
Ar$^1$ and Ar$^4$ are independently of each other a bivalent group of the formula

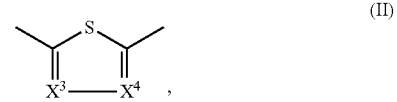

(II)

wherein one of X$^3$ and X$^4$ is N and the other is CR$^{100}$, and
R$^{100}$ is hydrogen, or C$_1$-C$_{25}$alkyl; or
Ar$^1$ and Ar$^4$ are independently of each other a bivalent group of the formula

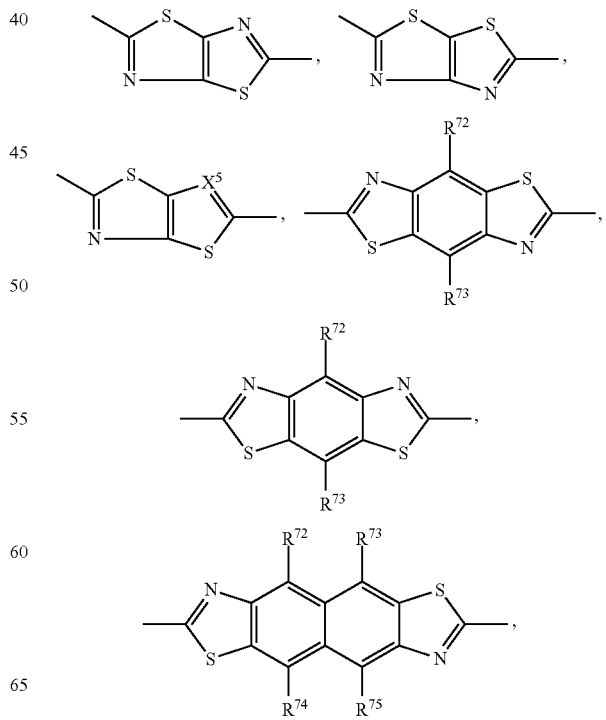

-continued

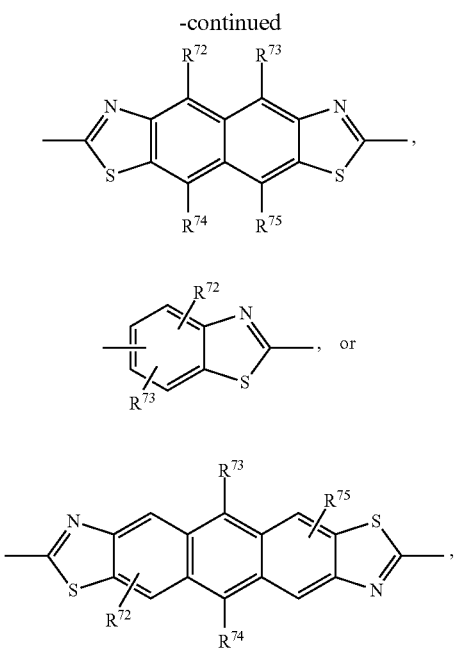

wherein $R^{72}$, $R^{73}$, $R^{74}$ and $R^{75}$ represent independently of each other hydrogen, an aliphatic hydrocarbon group having up to 25 carbon atoms, alkoxy or alkenyloxy having up to 25 carbon atoms, halogen, a cycloaliphatic, cycloaliphatic-aliphatic, aromatic, aromatic-aliphatic, heteroaromatic or heteroaromatic-aliphatic group having up to 25 carbon atoms, and $X^5$ is N, or $CR^{100}$, $R^{100}$ is hydrogen, or $C_1$-$C_{25}$alkyl.

In a preferred embodiment the present invention is directed to compounds of formula I, wherein $Ar^1$ and $Ar^4$ are independently of each other a bivalent group of the formula II, such as for example,

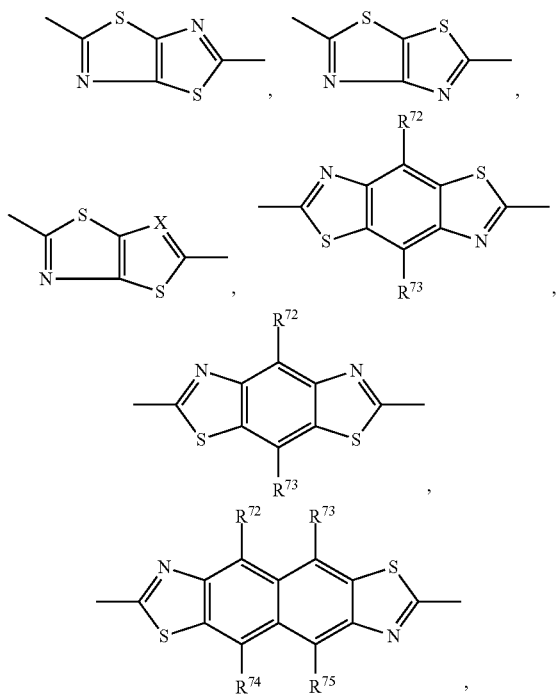

-continued

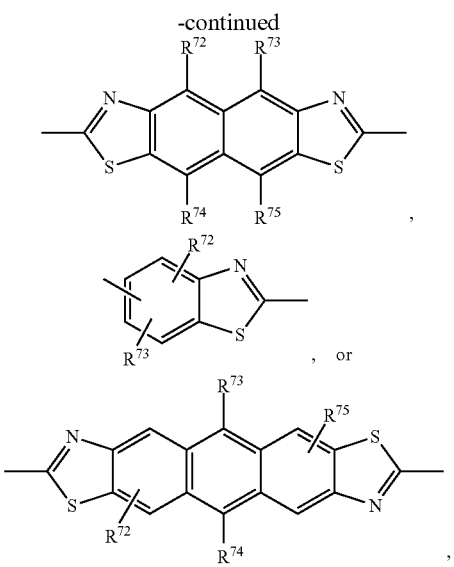

wherein
$R^{72}$, $R^{73}$, $R^{74}$ and $R^{75}$ are as defined above; and $Ar^2$, $Ar^3$, $Ar^5$, $Ar^6$, $Ar^7$ and $Ar^8$ are independently of one another of the formula II, IV, V, VI, VII, IX, Xa, Xb, or Xc. In said embodiment compounds of formula I are more preferred, wherein $Ar^1$ and $Ar^4$ are independently of each other a bivalent group of the formula II, and $Ar^2$, $Ar^3$, $Ar^5$, $Ar^6$, $Ar^7$ and $Ar^8$ are independently of one another of the formula II, IV, V, or VII, especially IV, V, or VII.

Compounds of the formula I are preferred, wherein $Ar^2$, $Ar^3$, $Ar^5$, $Ar^6$, $Ar^7$ and $Ar^8$ are independently of each other a bivalent group of the formula

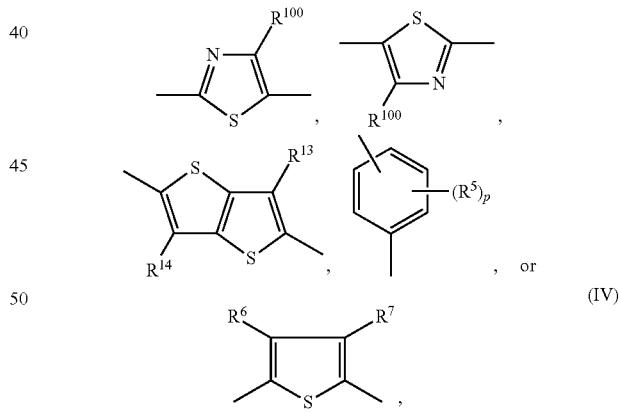

wherein $R^{100}$ is hydrogen, $C_1$-$C_{25}$alkyl, or $C_7$-$C_{25}$aralkyl; $R^5$ is $C_1$-$C_{25}$alkyl; $R^6$, $R^7$, $R^{13}$ and $R^{14}$ are independently of each other hydrogen, $C_7$-$C_{25}$aralkyl, or $C_1$-$C_{25}$alkyl; and p is 0, 1, or 2, such as

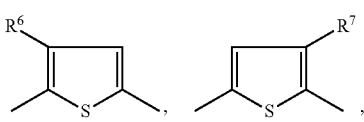

-continued

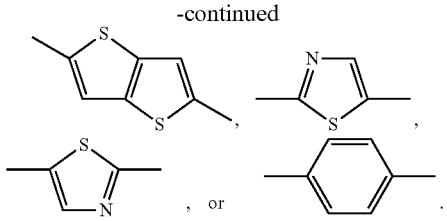

Groups of the formula

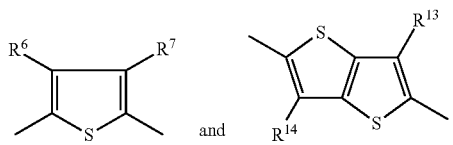

are preferred.

Compounds of the formula I are preferred, wherein $R^3$ and $R^4$ are independently of each other hydrogen, an aliphatic hydrocarbon group having up to 25 carbon atoms, a group of the formula

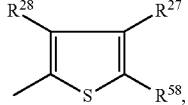 (XII)

especially

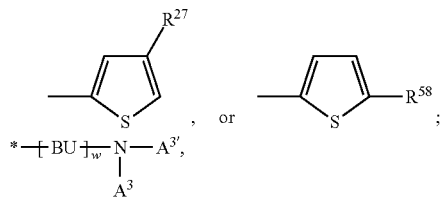 (XX)

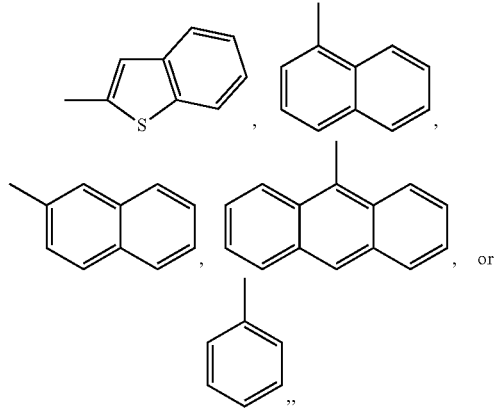

$R^{27}$ and $R^{28}$ are independently of each other hydrogen, $-CR^{203}R^{204}-(CH_2)_u-Ar$, or a $C_1$-$C_{25}$alkyl group, $R^{58}$ has the meaning of $R^{27}$, except hydrogen, $R^{203}$ and $R^{204}$ independently from each other stand for hydrogen, or $C_1$-$C_4$alkyl, Ar stands for phenyl or 1- or 2-naphthyl which can be substituted one to three times with $C_1$-$C_8$alkyl and/or $C_1$-$C_3$alkoxy, u stands for 0, 1, 2, 3 or 4, BU is

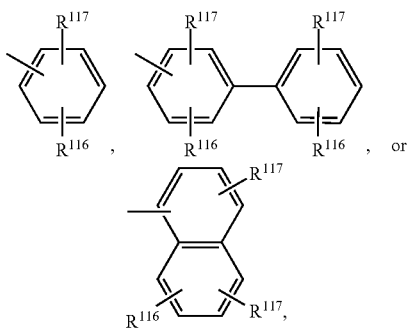

$R^{142}$ is $C_1$-$C_{18}$alkyl, $C_1$-$C_{18}$alkyl which is interrupted by O, $C_1$-$C_{18}$alkoxy,
m2 can be the same or different at each occurrence and is 0, or 1,
$A^3$ and $A^{3'}$ are independently of each other

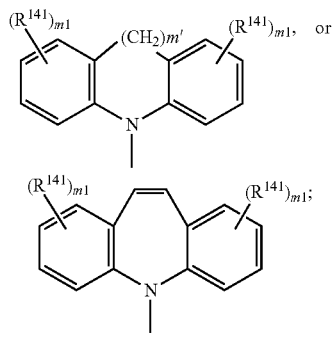

or $A^3$ and $A^{3'}$ together with the nitrogen atom to which they are bonded form a heteroaromatic ring, or ring system, such as

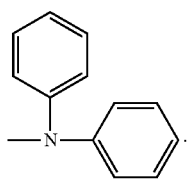

m' is 0, or 1,
$R^{116}$ and $R^{117'}$ are independently of each other H, $C_1$-$C_{18}$alkyl, $C_1$-$C_{18}$alkyl which is interrupted by O,
m1 can be the same or different at each occurrence and is 0, or 1, and
$R^{141}$ is $C_1$-$C_{18}$alkyl, $C_1$-$C_{18}$alkyl which is interrupted by O, $C_1$-$C_{18}$alkoxy, or phenyl, which is optionally substituted by Compounds of the formula I are preferred, wherein $R^1$ and $R^2$ independently from each other stand for $C_1$-$C_{100}$alkyl, $C_5$-$C_{12}$cycloalkyl, which can be substituted one to three times with $C_1$-$C_8$alkyl and/or $C_1$-$C_8$alkoxy, phenyl or 1- or 2-naphthyl which can be substituted one to three times with $C_1$-$C_8$alkyl and/or $C_1$-$C_8$alkoxy, or —$CR^{203}R^{204}$—$(CH_2)_u$— Ar, wherein $R^{203}$ and $R^{204}$ stand for hydrogen, or $C_1$-$C_4$alkyl, Ar stands for phenyl or 1- or 2-naphthyl, which can be substituted one to three times with $C_1$-$C_8$alkyl and/or $C_1$-$C_8$alkoxy, and u stands for 0, 1, 2, or 3, $R^3$ and $R^4$ are independently of each other hydrogen, halogen, especially F, or $C_1$, $C_1$-$C_{25}$alkyl, $C_1$-$C_{25}$alkoxy, or a group of one of the formulae

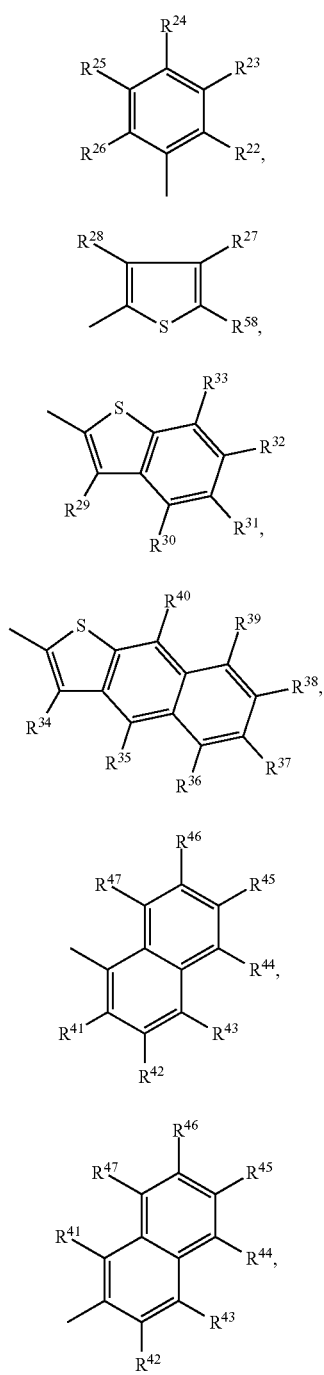

(XI)

(XII)

(XIII)

(XIV)

(XV)

(XVI)

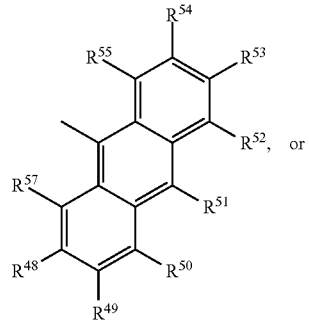

(XIX)

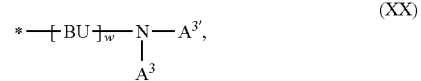

(XX)

wherein $R^{22}$ to $R^{26}$ and $R^{29}$ to $R^{58}$ represent independently of each other hydrogen, an aliphatic hydrocarbon group having up to 25 carbon atoms, w, BU, $A^3$ and $A^{3'}$ are as defined above, $R^{27}$ and $R^{28}$ are independently of each other hydrogen, $C_1$-$C_{25}$alkyl, or $C_1$-$C_{18}$alkoxy, or $R^{27}$ and $R^{28}$ together or $R^{27}$ and $R^{58}$ together represent alkylene or alkenylene which may be both bonded via oxygen and/or sulfur to the thienyl residue and which may both have up to 25 carbon atoms.

Compounds of the formula I are preferred, wherein $R^1$ and $R^2$ independently from each other stand for $C_1$-$C_{100}$alkyl, $C_5$-$C_{12}$cycloalkyl, which can be substituted one to three times with $C_1$-$C_8$alkyl and/or $C_1$-$C_8$alkoxy, phenyl or 1- or 2-naphthyl which can be substituted one to three times with $C_1$-$C_8$alkyl and/or $C_1$-$C_8$alkoxy, or —$CR^{203}R^{204}$—$(CH_2)_u$— Ar, wherein $R^{203}$ and $R^{204}$ stand for hydrogen, or $C_1$-$C_8$alkyl, Ar stands for phenyl or 1- or 2-naphthyl, which can be substituted one to three times with $C_1$-$C_8$alkyl and/or $C_1$-$C_8$alkoxy, and u stands for 0, 1, 2, or 3, a and d represent 1, b, c, e, f, g and h represent 0, 1, 2, or 3, $Ar^2$, $Ar^3$, $Ar^5$, $Ar^6$, $Ar^7$ and $Ar^8$ are independently of each other a bivalent group of the formula

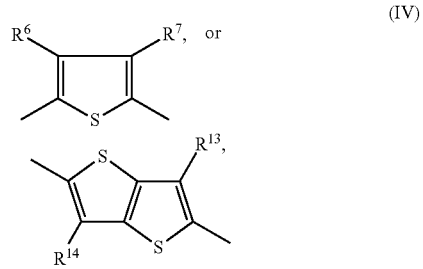

(IV)

wherein $R^6$, $R^7$, $R^{13}$ and $R^{14}$ are independently of each other hydrogen or $C_1$-$C_{25}$alkyl, and $R^3$ and $R^4$ are independently of each other hydrogen, an aliphatic hydrocarbon group having up to 25 carbon atoms, or a group of the formula

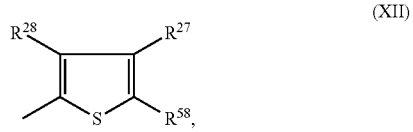

(XII)

$R^{58}$ represents hydrogen or an aliphatic hydrocarbon group having up to 25 carbon atoms, and $R^{27}$ and $R^{28}$ are independently of each other hydrogen or $C_1$-$C_{25}$alkyl.

Compounds of the formula I are preferred, wherein
$R^1$ and $R^2$ are independently of each other a $C_1$-$C_{36}$alkyl group,
a and d are independently of each other 1, or 2,
$Ar^1$ and $Ar^4$ are independently of each other a bivalent group of the formula

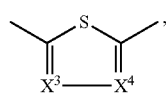
(II)

wherein one of $X^3$ and $X^4$ is N and the other is $CR^{100}$,
$R^{100}$ is hydrogen, or $C_1$-$C_{25}$alkyl,
b, c, e, f, g and h independently of each other represent 0, 1, 2 or 3,
$Ar^2$, $Ar^3$, $A^5$, $Ar^6$, $Ar^7$ and $Ar^8$ are independently of each other a bivalent group of the formula

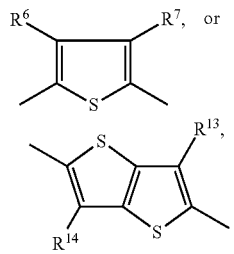
(IV) or (XIII)

wherein
$R^6$, $R^7$, $R^{13}$ and $R^{14}$ are independently of each other hydrogen, $C_1$-$C_{25}$alkyl, or $C_7$-$C_{25}$aralkyl, and
$R^3$ and $R^4$ are independently of each other hydrogen, an aliphatic hydrocarbon group having up to 25 carbon atoms, or a group of one of the formulae

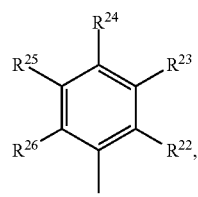
(XI)

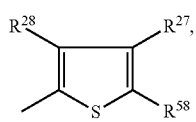
(XII)

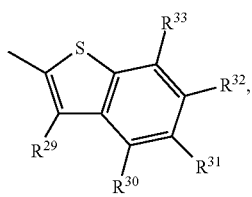
(XIII)

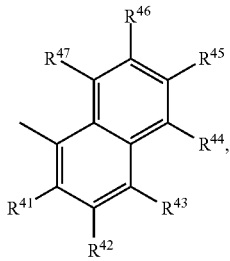
(XV)

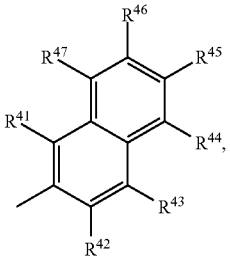
(XVI)

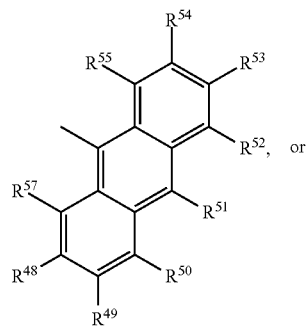
(XIX)

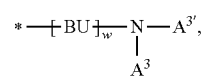
(XX)

wherein $R^{22}$ to $R^{26}$, $R^{29}$ to $R^{33}$, $R^{41}$ to $R^{55}$, $R^{57}$ and $R^{58}$ represent independently of each other hydrogen, an aliphatic hydrocarbon group having up to 25 carbon atoms, aryl, alkoxy having up to 18 carbon atoms, or halogen, or two groups $R^{22}$ to $R^{26}$ which are in the neighborhood of each other, together represent alkylene or alkenylene having up to 8 carbon atoms, thereby forming a ring, w, BU, $A^3$ and $A^{3'}$ are as defined above,
$R^{27}$ and $R^{28}$ are independently of each other hydrogen, $C_1$-$C_{25}$alkyl, or $C_7$-$C_{25}$aralkyl, or $R^{27}$ and $R^{28}$ together represent alkylene or alkenylene which may be both bonded via oxygen and/or sulfur to the thienyl residue and which may both have up to 25 carbon atoms.
$R^3$ and $R^4$ may be a group of formula

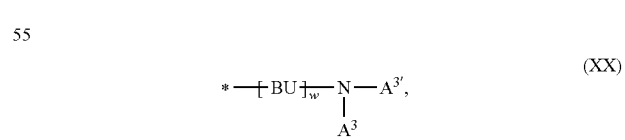
(XX)

wherein
w is 0, or 1, BU is a bridging unit and $A^3$ and $A^{3'}$ are independently of each other a $C_6$-$C_{24}$aryl group, or a $C_2$-$C_{26}$heteroaryl group, which can optionally be substituted. Typical substituents of the $C_6$-$C_{24}$aryl group, or $C_2$-$C_{26}$heteroaryl group are $C_1$-$C_{18}$alkyl, or $C_1$-$C_{18}$alkoxy, which can be present one or more times.

BU is a bridging unit, such as for example,

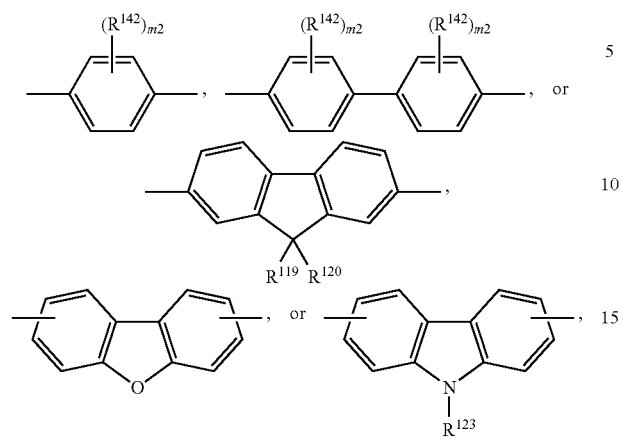

wherein
$R^{119}$ and $R^{120}$ are independently of each other $C_1$-$C_{18}$alkyl, such as methyl, ethyl, n-propyl, iso-propyl, n-butyl, sec-butyl, hexyl, octyl, or 2-ethyl-hexyl, $C_1$-$C_{12}$alkyl which is interrupted by O, such as —$CH_2(OCH_2CH_2)_vOCH_3$, v=1, 2, 3, or 4, $C_6$-$C_{14}$aryl, such as phenyl, naphthyl, or biphenylyl, $C_6$-$C_{14}$aryl which is substituted by $C_1$-$C_8$alkyl, or $C_1$-$C_8$alkoxy, such as —$C_6H_4OCH_3$, —$C_6H_4OCH_2CH_3$, —$C_6H_3(OCH_3)_2$, —$C_6H_3(OCH_2CH_3)_2$, —$C_6H_4CH_3$, —$C_6H_3(CH_3)_2$, —$C_6H_2(CH_3)_3$, or —$C_6H_4tBu$, or $R^{119}$ and $R^{120}$ together form a 4 to 8 membered ring, especially a 5 or 6 membered ring, such as cyclohexyl, or cyclopentyl, which can optionally be substituted by $C_1$-$C_8$alkyl, $R^{123}$ is $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl, or $C_1$-$C_{18}$alkyl which is interrupted by —O—;

m2 can be the same or different at each occurrence and is 0, or 1, and $R^{142}$ is $C_1$-$C_{18}$alkyl, $C_1$-$C_{18}$alkyl which is interrupted by 0, or phenyl, which is optionally substituted by $C_1$-$C_8$alkyl, or $C_1$-$C_8$alkoxy.

$A^3$ and $A^{3'}$ are especially phenyl, naphthyl, anthryl, biphenylyl, 2-fluorenyl, phenanthryl, or perylenyl, which can optionally be substituted, such as

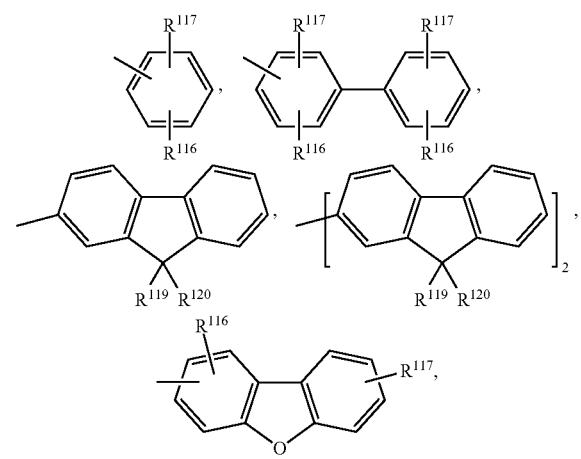

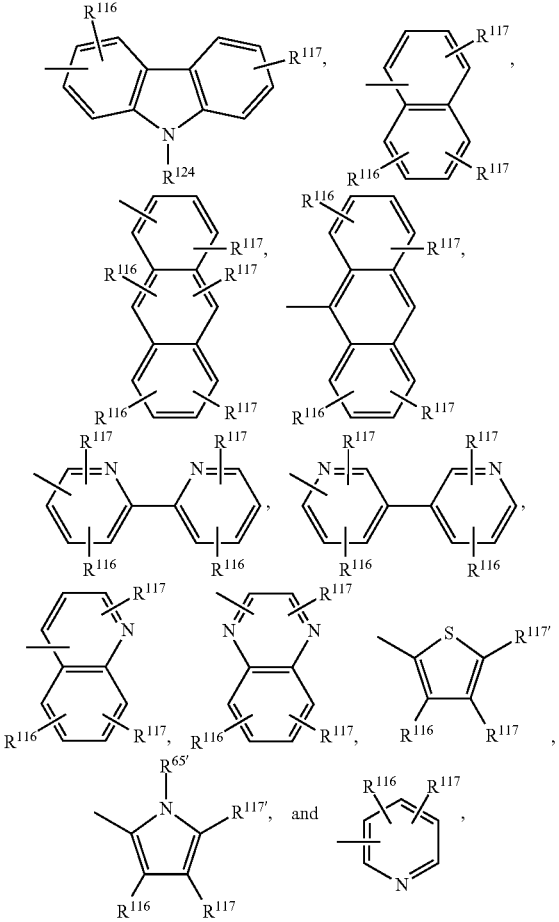

or $A^3$ and $A^{3'}$ together with the nitrogen atom to which they are bonded form a heteroaromatic ring, or ring system, such as

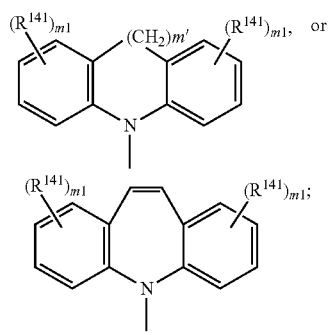

m' is 0, 1, or 2;
m1 can be the same or different at each occurrence and is 0, 1, 2, 3, or 4, especially 0, 1, or 2, very especially 0 or 1;
$R^{65'}$ is $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—;
$R^{116}$, $R^{117}$ and $R^{117'}$ are independently of each other H, halogen, especially F, —CN, $C_1$-$C_{18}$alkyl, $C_1$-$C_{18}$alkyl which is interrupted by O, $C_6$-$C_{24}$aryl, $C_6$-$C_{24}$aryl which is substituted by $C_1$-$C_{18}$alkyl, or $C_1$-$C_{18}$alkoxy; $C_2$-$C_{20}$heteroaryl, $C_2$-$C_{20}$heteroaryl which is substituted by $C_1$-$C_{18}$alkyl, $C_1$-$C_{18}$alkoxy; $C_1$-$C_{18}$alkoxy, $C_7$-$C_{25}$aralkyl, $C_7$-$C_{25}$aralkyl, which is substituted by $C_1$-$C_{18}$alkyl, or $C_1$-$C_{18}$alkoxy; or substituents $R^{116}$, $R^{117}$ and $R^{117'}$, which are adjacent to each other, can form a ring, $R^{124}$ is $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl which is interrupted by —O—; $R^{119}$ and $R^{120}$ are as defined above, and $R^{141}$ is H, or $C_1$-$C_{18}$alkyl, or phenyl, which is optionally be substituted by

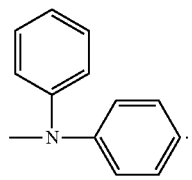

Examples of a heteroaromatic ring, or ring system, which is formed by $A^3$ and $A^{3'}$ together with the nitrogen atom to which they are bonded, are

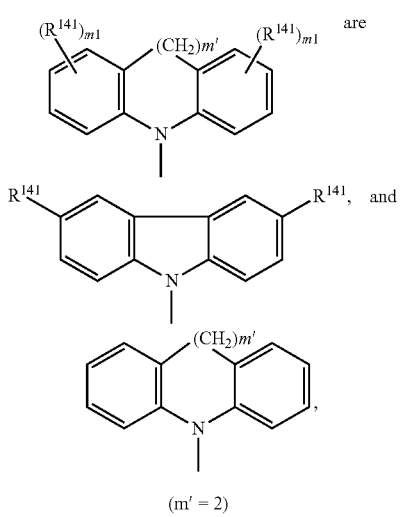

m1 and m' are independently of each other 0, 1, or 2.
Examples of wherein $R^{141}$ is H, or $C_1$-$C_{18}$alkyl, or phenyl, which is optionally be substituted by

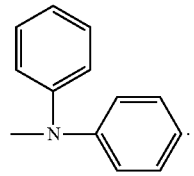

In formula (XX) BU is preferably $R^{142}$ is $C_1$-$C_{18}$alkyl, $C_1$-$C_{18}$alkyl which is interrupted by O, $C_1$-$C_{18}$alkoxy, m2 can be the same or different at each occurrence and is 0, or 1, and $A^3$ and $A^{3'}$ are preferably independently of each other

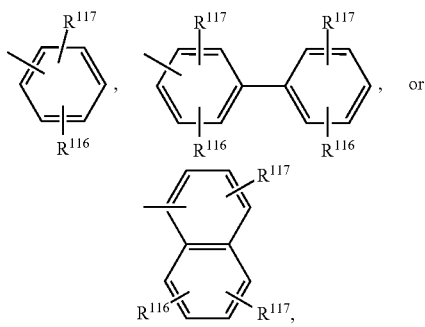

or $A^3$ and $A^{3'}$ together with the nitrogen atom to which they are bonded form a heteroaromatic ring, or ring system, such as m' is 0, or 1, $R^{116}$ and $R^{117'}$ are independently of each other H, $C_1$-$C_{18}$alkyl, $C_1$-$C_{18}$alkyl which is interrupted by O, m1 can be the same or different at each occurrence and is 0, or 1, and $R^{141}$ is $C_1$-$C_{18}$alkyl, $C_1$-$C_{18}$alkyl which is interrupted by O, $C_1$-$C_{18}$alkoxy, or phenyl, which is optionally substituted by

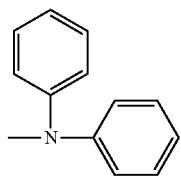
Examples of groups
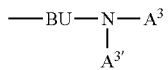
are shown below:
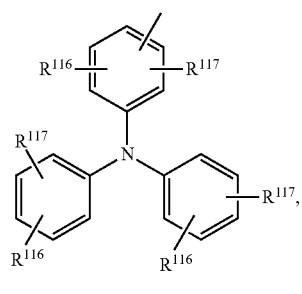
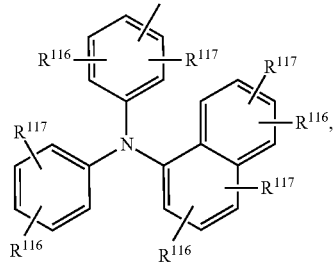
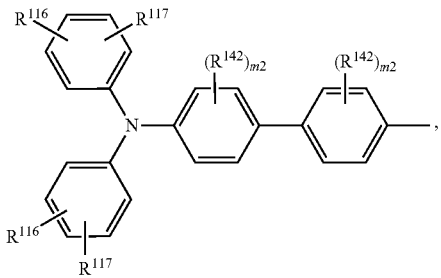
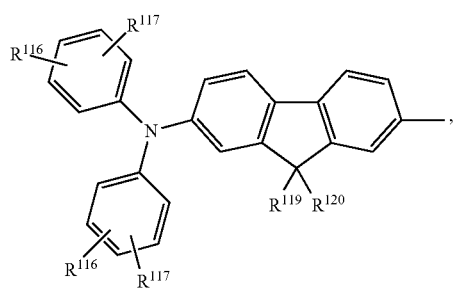
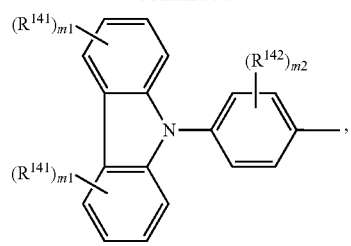
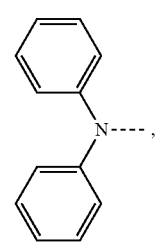
wherein $R^{116}$, $R^{117}$, $R^{119}$, $R^{120}$, $R^{141}$, $R^{142}$, m1 and m2 are as defined above. Specific examples are groups AM-1 to AM-13 shown below:
(AM-1)
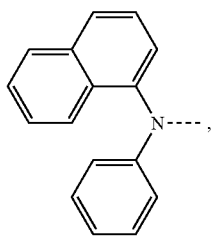
(AM-2)

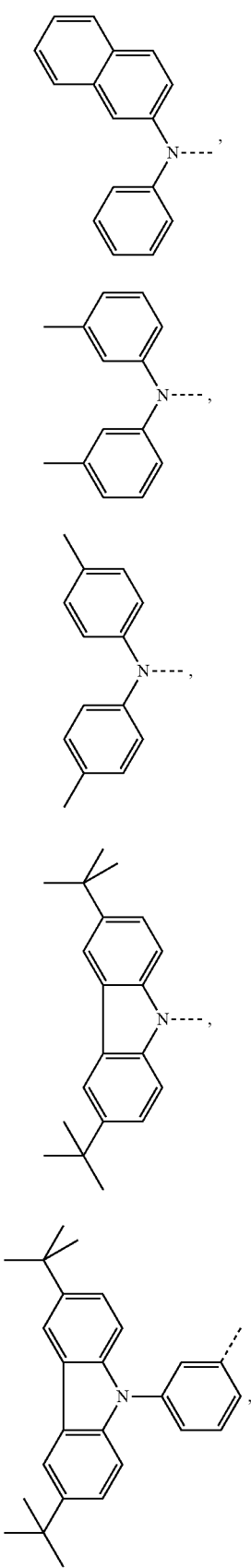
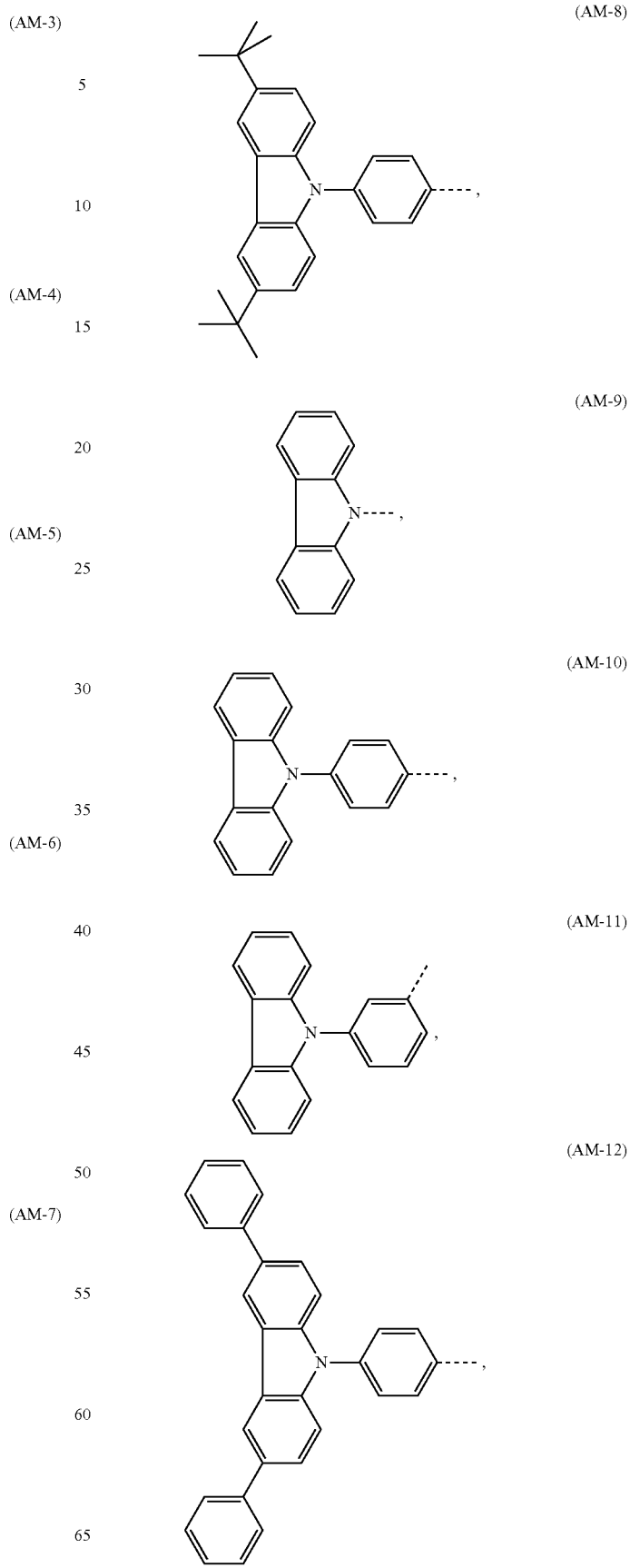

-continued (AM-13)

[structure: triphenylamine-substituted carbazole attached to phenyl group]

R³ and R⁴ are preferably selected from hydrogen,

[structures: 5-methylthiophene with R²⁷, thiophene-R⁵⁸, benzothiophene, naphthyl (1- and 2-), anthracenyl, phenyl]

or a group AM-1 to AM-13, wherein $R^{27}$ is hydrogen, $-CR^{203}R^{204}-(CH_2)_u-Ar$, or a $C_1$-$C_{25}$alkyl group, $R^{58}$ has the meaning of $R^{27}$, except hydrogen, $R^{203}$ and $R^{204}$ independently from each other stand for hydrogen, or $C_1$-$C_4$alkyl, Ar stands for phenyl or 1- or 2-naphthyl which can be substituted one to three times with $C_1$-$C_8$alkyl and/or $C_1$-$C_8$alkoxy, and u stands for 0, 1, 2, 3 or 4.

In a preferred embodiment the present invention is directed to compounds of formula

[structure showing pyrrolopyrrole dione core with R¹, Ar¹—R³, R⁴—Ar⁴', R¹ substituents]

wherein $R^1$ is $-CR^{203}R^{204}-(CH_2)_u-Ar$, or a $C_1$-$C_{36}$alkyl group, $Ar^1$ is

[structures: thiazole isomers]

and $Ar^{4'}$ is

[structures: thiazoles, thienothiophene, phenylene, thiophene-2,5-diyl]

and $R^3$ and $R^4$ are hydrogen, $C_1$-$C_{25}$alkyl, (XX)

[structures: 5-methylthiophene with R²⁷, thiophene-R⁵⁸, benzothiophene, anthracenyl, naphthyl (1- and 2-), phenyl, or *—[BU]_w—N(A³')(A³)]

$R^{27}$ is hydrogen, $-CR^{203}R^{204}-(CH_2)_u-Ar$, or a $C_1$-$C_{25}$alkyl group, $R^{58}$ has the meaning of $R^{27}$, except hydrogen, $R^{203}$ and $R^{204}$ independently from each other stand for hydrogen, or $C_1$-$C_4$alkyl, Ar stands for phenyl or 1- or 2-naphthyl which can be substituted one to three times with $C_1$-$C_8$alkyl and/or $C_1$-$C_8$alkoxy, and u stands for 0, 1, 2, 3 or 4.

In another preferred embodiment the present invention is directed to compounds of formula

[structure showing pyrrolopyrrole dione core with R¹, Ar¹—Ar²—R³, R⁴—Ar⁵—Ar⁴', R¹ substituents]

wherein $R^1$ is $-CR^{203}R^{204}-(CH_2)_u-Ar$, or a $C_1$-$C_{36}$alkyl group, $Ar^1$ is

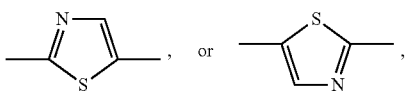

and Ar², Ar⁴' and Ar⁵ are independently of each other (IV)

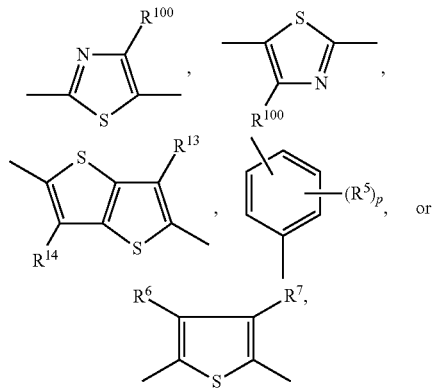

wherein $R^{100}$ is hydrogen, $C_1$-$C_{25}$alkyl, or $C_7$-$C_{25}$aralkyl; $R^5$ is $C_1$-$C_{25}$alkyl; $R^6$, $R^7$, $R^{13}$ and $R^{14}$ are independently of each other hydrogen, $C_7$-$C_{25}$aralkyl, or $C_1$-$C_{25}$alkyl, p is 0, 1, or 2; and $R^3$ and $R^4$ are hydrogen, $C_1$-$C_{25}$alkyl, (XX)

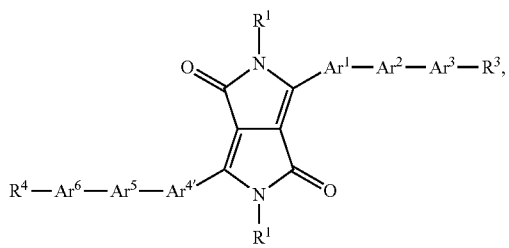

$R^{27}$ is hydrogen, —$CR^{203}R^{204}$—$(CH_2)_u$—Ar, or a $C_1$-$C_{25}$alkyl group, $R^{58}$ has the meaning of $R^{27}$, except hydrogen, $R^{203}$ and $R^{204}$ independently from each other stand for hydrogen, or $C_1$-$C_4$alkyl, Ar stands for phenyl or 1- or 2-naphthyl which can be substituted one to three times with $C_1$-$C_8$alkyl and/or $C_1$-$C_8$alkoxy, and u stands for 0, 1, 2, 3 or 4.

In another preferred embodiment the present invention is directed to compounds of formula

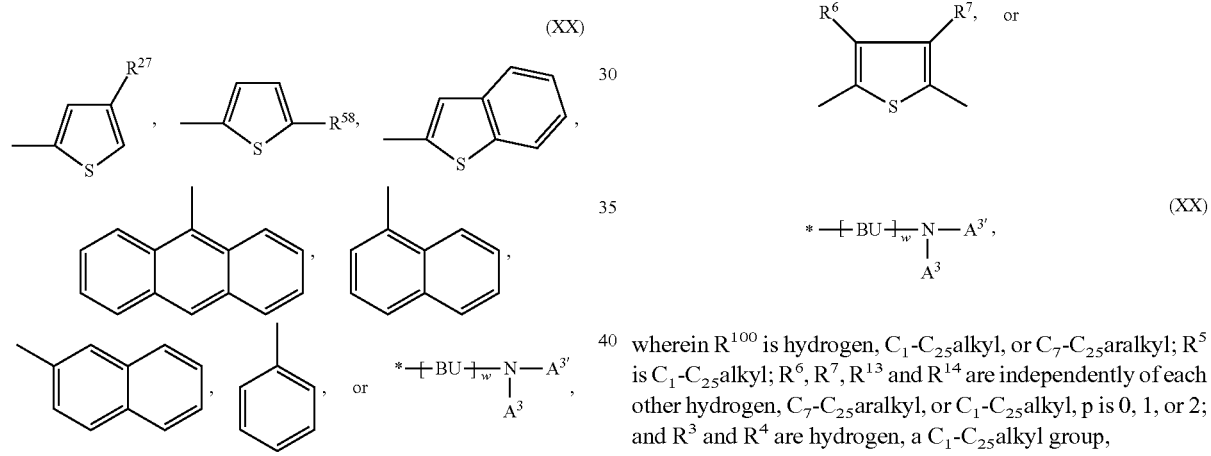

wherein $R^1$ is —$CR^{203}R^{204}$—$(CH_2)_u$—Ar, or a $C_1$-$C_{36}$alkyl group, $Ar^1$ is

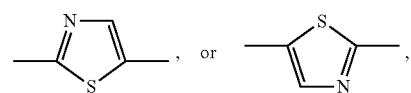

and Ar², Ar⁴', Ar³, Ar⁶ and Ar⁵ are independently of each other (IV)

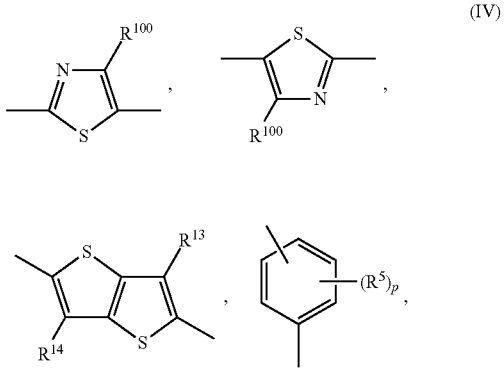

(XX)

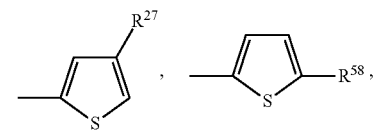

wherein $R^{100}$ is hydrogen, $C_1$-$C_{25}$alkyl, or $C_7$-$C_{25}$aralkyl; $R^5$ is $C_1$-$C_{25}$alkyl; $R^6$, $R^7$, $R^{13}$ and $R^{14}$ are independently of each other hydrogen, $C_7$-$C_{25}$aralkyl, or $C_1$-$C_{25}$alkyl, p is 0, 1, or 2; and $R^3$ and $R^4$ are hydrogen, a $C_1$-$C_{25}$alkyl group,

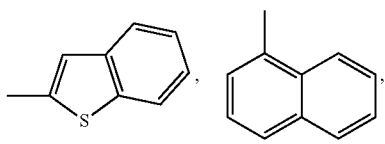

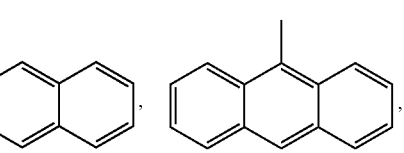

-continued

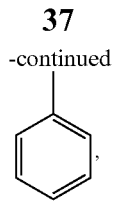,

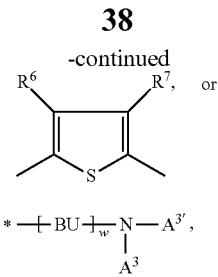

$R^{27}$ is hydrogen, $-CR^{203}R^{204}-(CH_2)_u-Ar$, or a $C_1$-$C_{25}$alkyl group, $R^{58}$ has the meaning of $R^{27}$, except hydrogen, $R^{203}$ and $R^{204}$ independently from each other stand for hydrogen, or $C_1$-$C_4$alkyl, Ar stands for phenyl or 1- or 2-naphthyl which can be substituted one to three times with $C_1$-$C_8$alkyl and/or $C_1$-$C_8$alkoxy, and u stands for 0, 1, 2, 3 or 4.

wherein $R^{100}$ is hydrogen, $C_1$-$C_{25}$alkyl, or $C_7$-$C_{25}$aralkyl; $R^5$ is $C_1$-$C_{25}$alkyl; $R^6$, $R^7$, $R^{13}$ and $R^{14}$ are independently of each other hydrogen, $C_7$-$C_{25}$aralkyl, or $C_1$-$C_{25}$alkyl, p is 0, 1, or 2; and $R^3$ and $R^4$ are hydrogen, $C_1$-$C_{25}$alkyl group, In another preferred embodiment the present invention is directed to compounds of formula

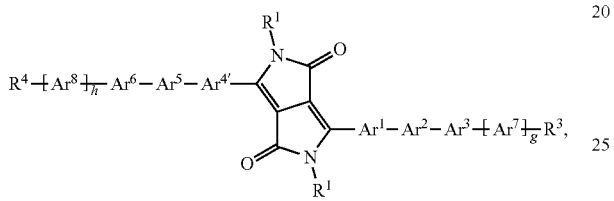

wherein g is 1, or 2, h is 1, or 2, $R^1$ is $-CR^{203}R^{204}-(CH_2)_u-Ar$, or a $C_1$-$C_{36}$alkyl group, $Ar^1$ is

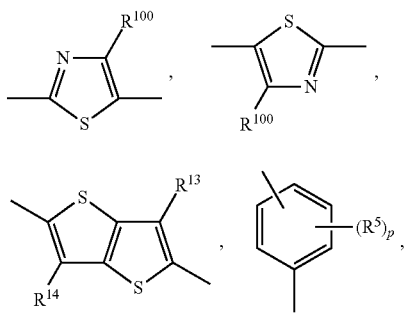

and $Ar^2$, $Ar^3$, $Ar^{4'}$, $Ar^5$, $Ar^6$, $Ar^7$ and $Ar^8$ are independently of each other (IV)

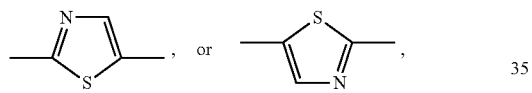

$R^{27}$ is hydrogen, $-CR^{203}R^{204}-(CH_2)_u-Ar$, or a $C_1$-$C_{36}$alkyl group, $R^{58}$ has the meaning of $R^{27}$, except hydrogen, $R^{203}$ and $R^{204}$ independently from each other stand for hydrogen, or $C_1$-$C_4$alkyl, Ar stands for phenyl or 1- or 2-naphthyl which can be substituted one to three times with $C_1$-$C_8$alkyl and/or $C_1$-$C_8$alkoxy, and u stands for 0, 1, 2, 3 or 4. w, BU, $A^3$ and $A^{3'}$ are as defined above.

Examples of particularly preferred compounds are compounds A-1 to A-54 shown in claim 10.

Compounds of the formula

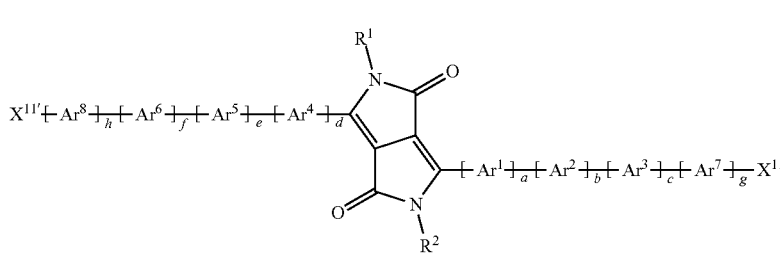

(L)

represent intermediates in the preparation of the compounds of formula I and form a further subject of the present invention.

$X^{11}$ and $X^{11'}$ represent independently of each other halogen, especially Br, or I, $ZnX^{12}$, —$SnR^{267}R^{208}R^{209}$, wherein $R^{207}$, $R^{208}$ and $R^{209}$ are identical or different and are H or $C_1$-$C_6$alkyl, wherein two radicals optionally form a common ring and these radicals are optionally branched or unbranched and $X^{12}$ is a halogen atom, very especially I, or Br; or —OS$(O)_2CF_3$, —OS$(O)_2$-aryl, especially

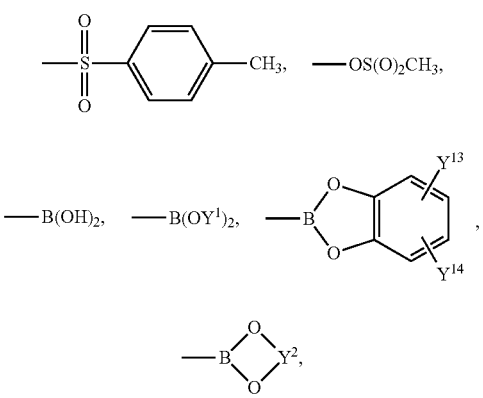

—$BF_4Na$, or —$BF_4K$, wherein $Y^1$ is independently in each occurrence a $C_1$-$C_{10}$alkyl group and $Y^2$ is independently in each occurrence a $C_2$-$C_{10}$alkylene group, such as —$CY^3Y^4$—$CY^5Y^6$—, or —$CY^7Y^8$—$CY^9Y^{10}$—$CY^{11}Y^{12}$—, wherein $Y^3, Y^4, Y^5, Y^6, Y^7, Y^8, Y^9, Y^{10}, Y^{11}$ and $Y^{12}$ are independently of each other hydrogen, or a $C_1$-$C_{10}$alkyl group, especially —$C(CH_3)_2C(CH_3)_2$—, —$C(CH_3)_2CH_2C(CH_3)_2$—, or —$CH_2C(CH_3)_2CH_2$—, and $Y^{13}$ and $Y^{14}$ are independently of each other hydrogen, or a $C_1$-$C_{10}$alkyl group, and a, b, c, d, e, f, g, h, $R^1$, $R^2$, $Ar^1$, $Ar^2$, $Ar^3$, $Ar^4$, $Ar^5$, $Ar^6$, $Ar^7$ and $Ar^8$ are as defined above, with the proviso that the following compounds are excluded

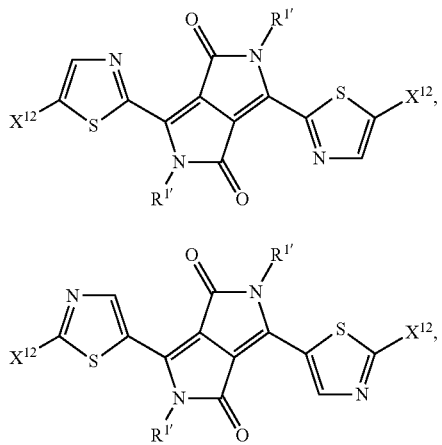

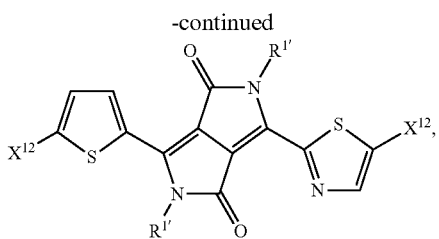

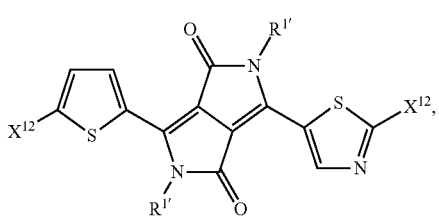

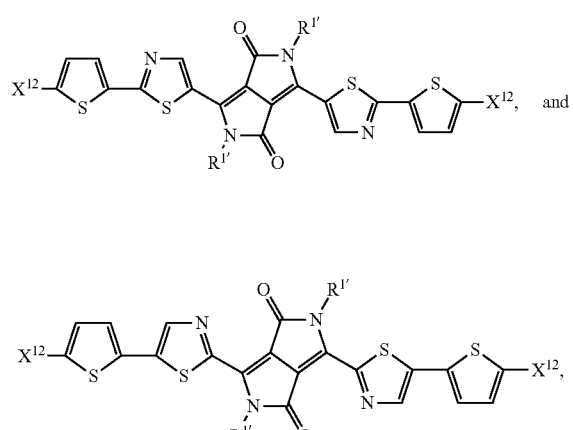

wherein $X^{12}$ is —$B(OH)_2$, —$B(OY^{30})_2$,

—$BF_3Na$, —$BF_3N(Y^{33})_4$, or —$BF_3K$, wherein $Y^{30}$ is independently in each occurrence a $C_1$-$C_{10}$alkyl group and $Y^{31}$ is independently in each occurrence a $C_2$-$C_{10}$alkylene group, and $Y^{33}$ is H, or a $C_1$-$C_{25}$alkyl group, which may optionally be interrupted by O.

In a preferred embodiment of the present invention $Ar^1$ (and optionally $Ar^4$) is an annulated (aromatic) heterocyclic ring system, containing at least one thiazole ring, which may be optionally substituted by one, or more groups.

Particularly suitable intermediates for the production of the compounds of the formula I are, for example, the compounds shown below:

41 42
(B-1)
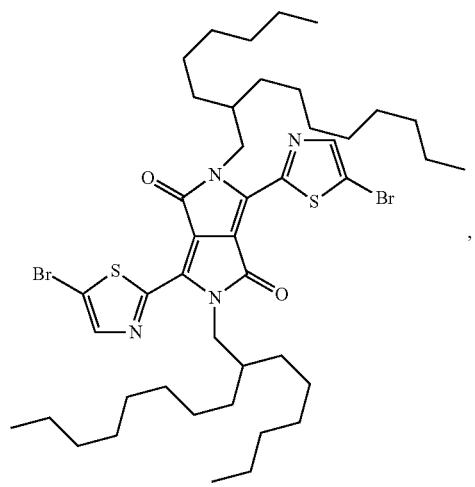
(B-2)
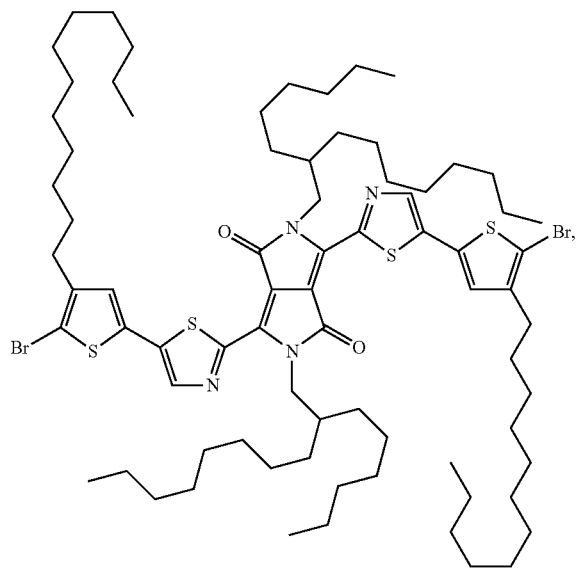
(B-3)
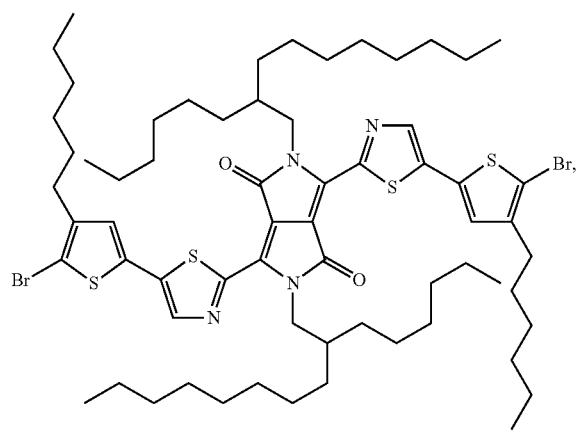
(B-4)
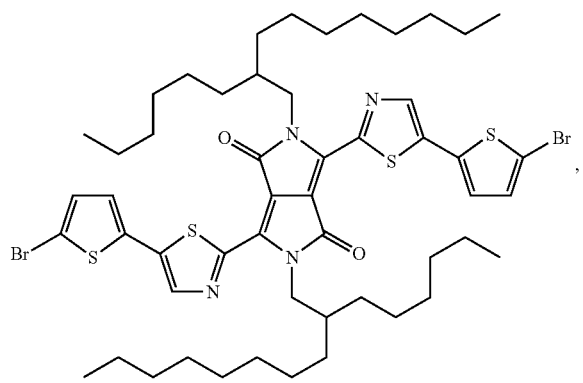
(B-5)
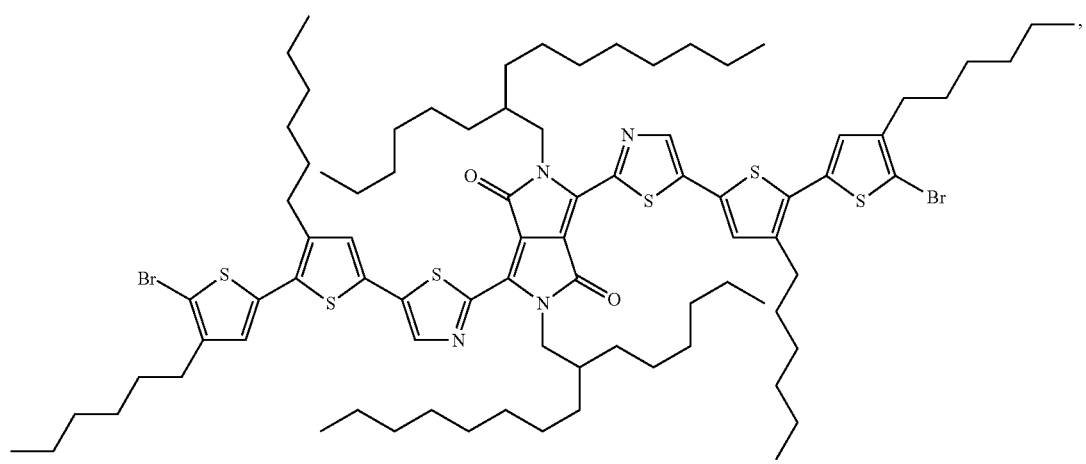

-continued
(B-6)
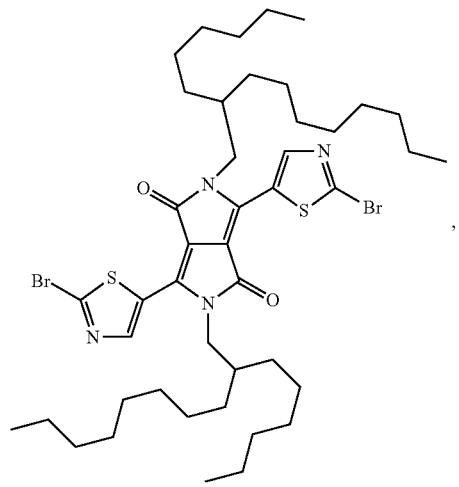
(B-7)
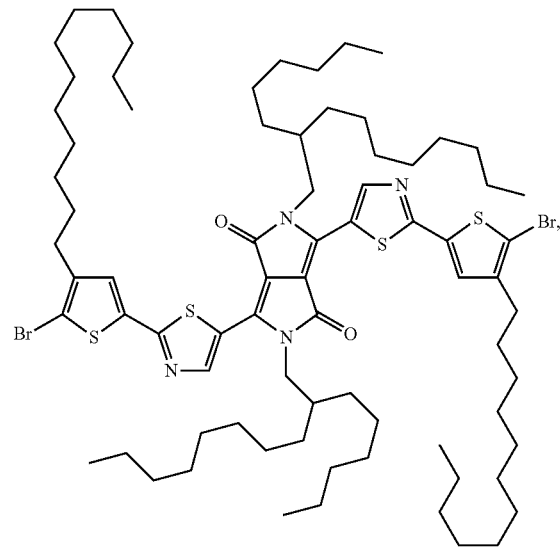
(B-8)
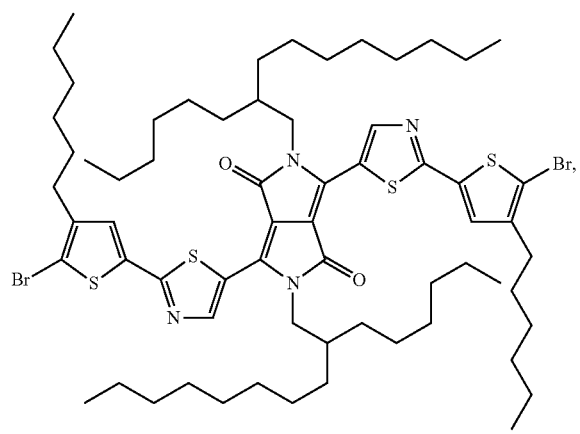
(B-9)
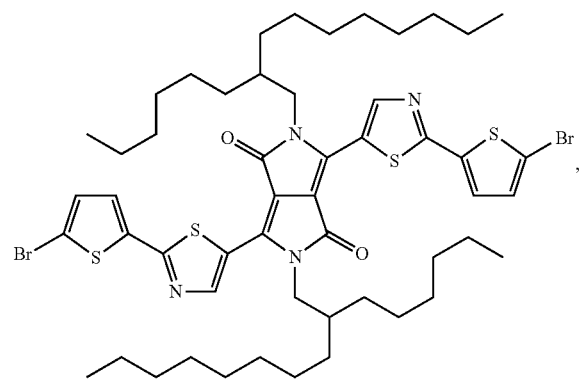
(B-10)
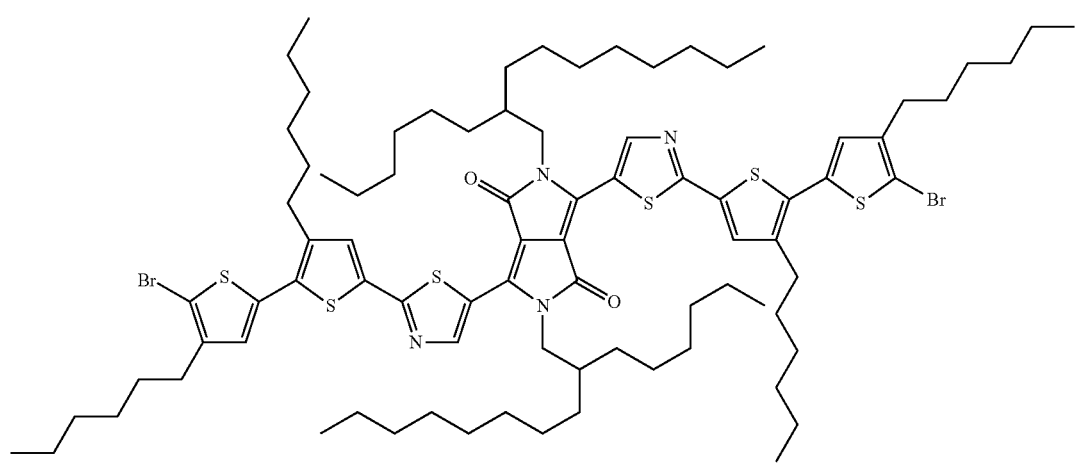

-continued
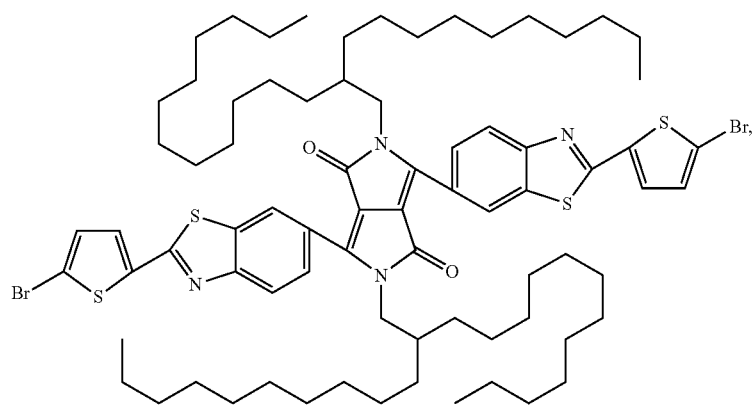
(B-11)
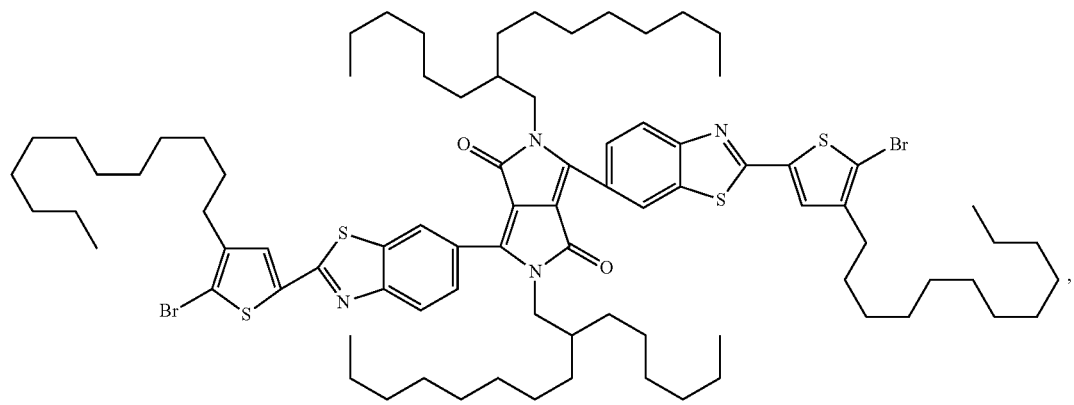
(B-12)
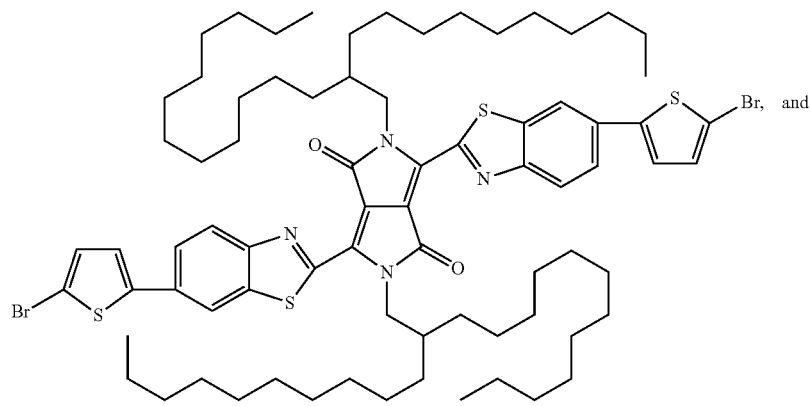
(B-13) and
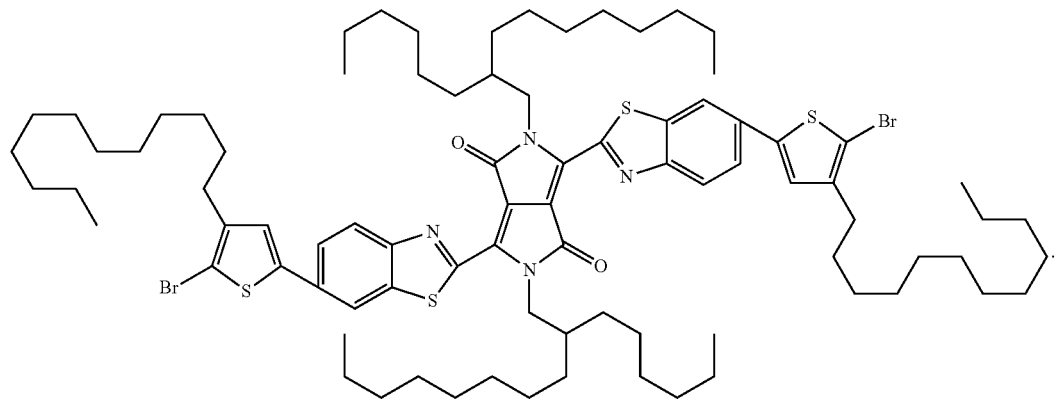
(B-14)

Compounds of the formula L can be used to prepare polymers. Polymers comprising a repeating unit of formula

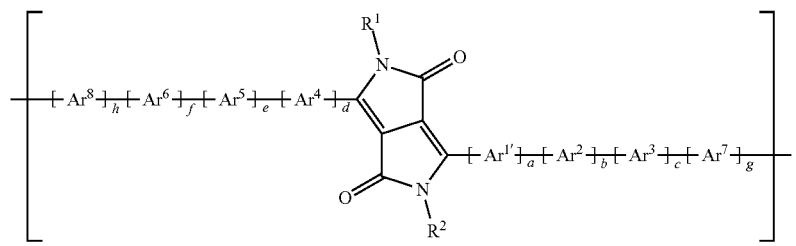

are new and form a further subject of the present invention, wherein $Ar^{1'}$ is an annulated (aromatic) heterocyclic ring system, containing at least one thiazole ring, which may be optionally substituted by one, or more groups, and a, b, c, d, e, f, g, h, $R^1$, $R^2$, $Ar^2$, $Ar^3$, $Ar^4$, $Ar^5$, $Ar^6$, $Ar^7$ and $Ar^8$ are as defined above.

The term polymer comprises oligomers as well as polymers. The oligomers of this invention have a weight average molecular weight of <4,000 Daltons. The polymers of this invention preferably have a weight average molecular weight of 4,000 Daltons or greater, especially 4,000 to 2,000,000 Daltons, more preferably 10,000 to 1,000,000 and most preferably 10,000 to 100,000 Daltons. Molecular weights are determined according to high-temperature gel permeation chromatography (HT-GPC) using polystyrene standards. The polymers of this invention preferably have a polydispersity of 1.01 to 10, more preferably 1.1 to 3.0, most preferred 1.5 to 2.5.

In a preferred embodiment of the present invention the polymer is a homopolymer of formula

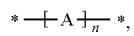

wherein A is a repeating unit of formula

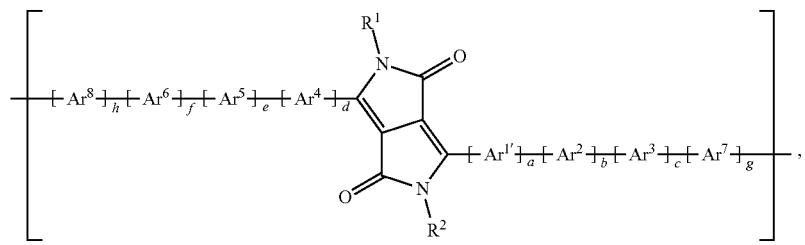

n is number which results in a molecular weight of 4,000 to 2,000,000 Daltons, more preferably 10,000 to 1,000,000 and most preferably 10,000 to 100,000 Daltons. n is usually in the range of 4 to 1000, especially 4 to 200, very especially 5 to 150.

In a further preferred embodiment of the present invention the polymer comprises one or more (repeating) unit(s) of the formula *—[—A—]—* and *—[—COM¹—]—* (II), wherein A is as defined above; and —COM¹— is a repeating unit, which is selected from a group of formula $Ar^2$,

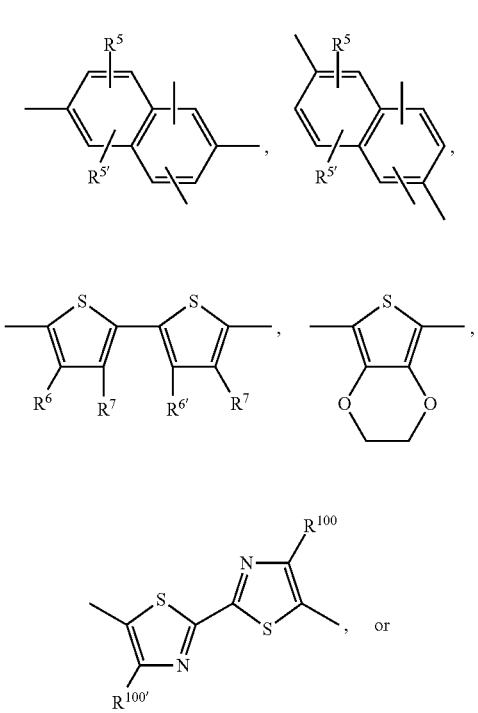

-continued

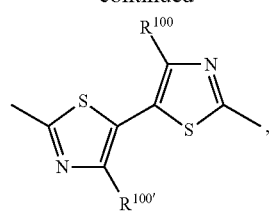

wherein a, b, c, d, e, f, g, h, $R^1$, $R^2$, $R^5$, $R^6$, $R^7$, $R^{100}$, $Ar^2$, $Ar^3$, $Ar^4$, $Ar^5$, $Ar^6$, $Ar^7$ and $Ar^8$ are as defined above, $R^{6'}$ and $R^{7'}$ have the meaning of $R^6$, $R^{5'}$ has the meaning of $R^5$, and $R^{100'}$ has the meaning of $R^{100}$.

In a preferred embodiment of the present invention the polymer is a copolymer, comprising repeating units of formula *─[─A─]─[─COM$^1$─]─* (VII), especially a copolymer of formula

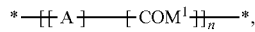

wherein A and COM$^1$ are as defined above; n is number which results in a molecular weight of 4,000 to 2,000,000 Daltons, more preferably 10,000 to 1,000,000 and most preferably 10,000 to 100,000 Daltons. n is usually in the range of 4 to 1000, especially 4 to 200, very especially 5 to 150.

Examples of preferred polymers are shown below:

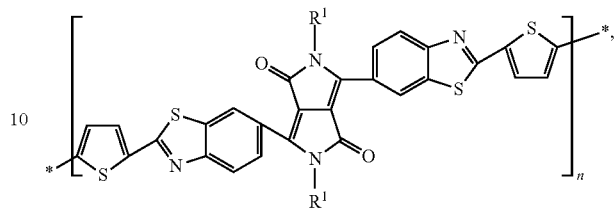

such as, for example,

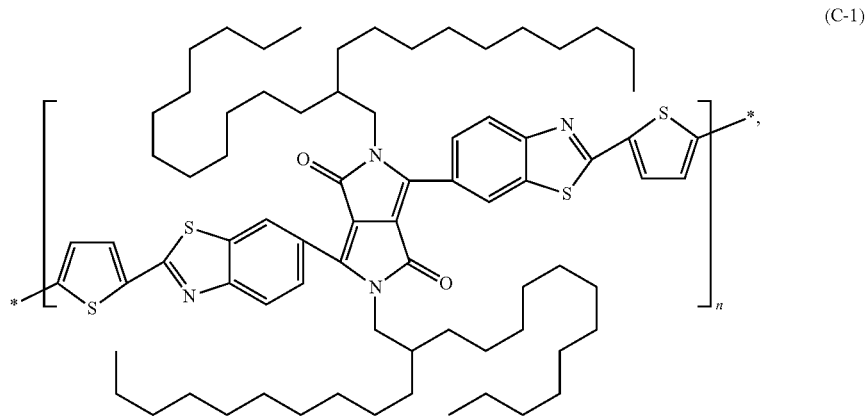
(C-1)

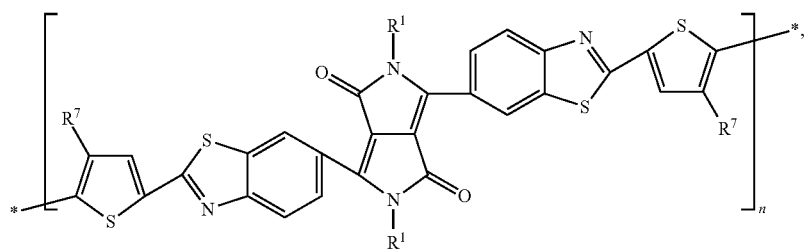

such as, for example,

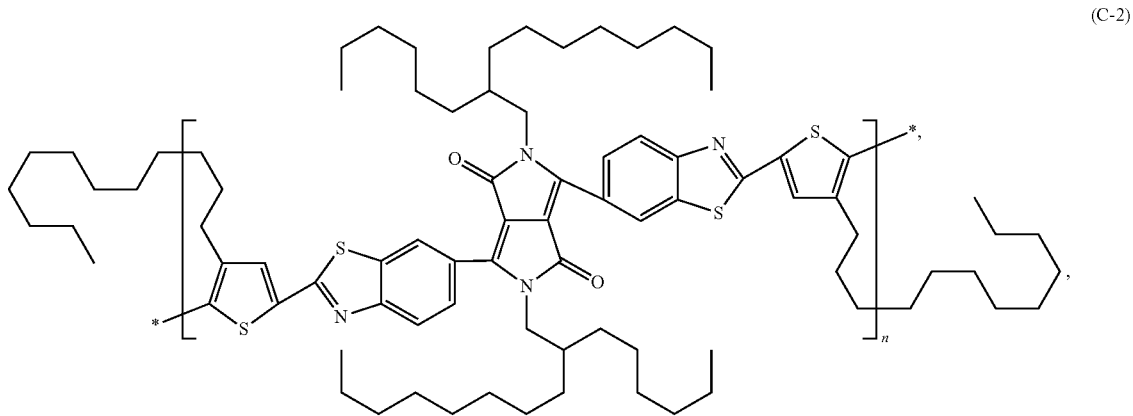
(C-2)

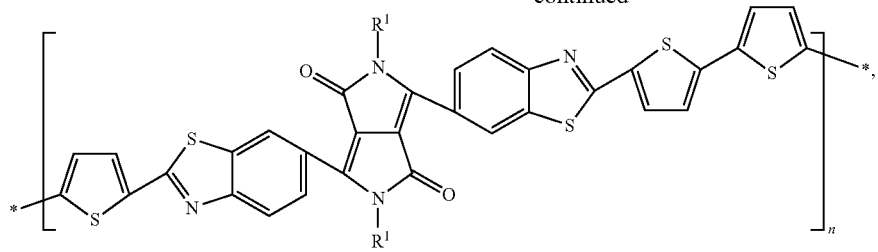
such as, for example,
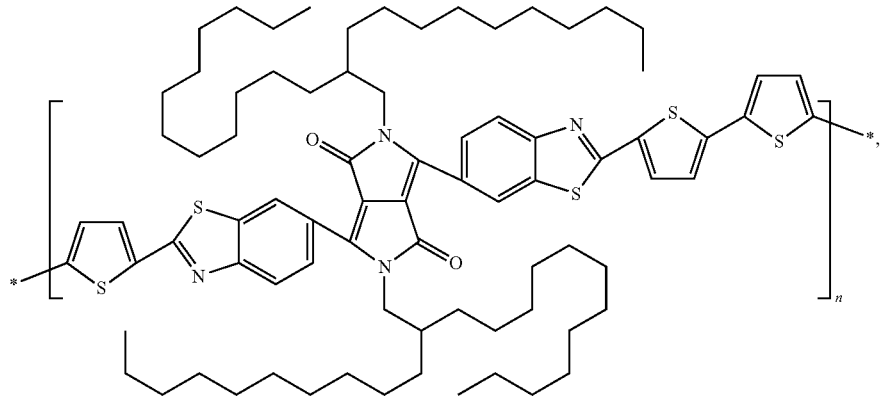
(C-3)
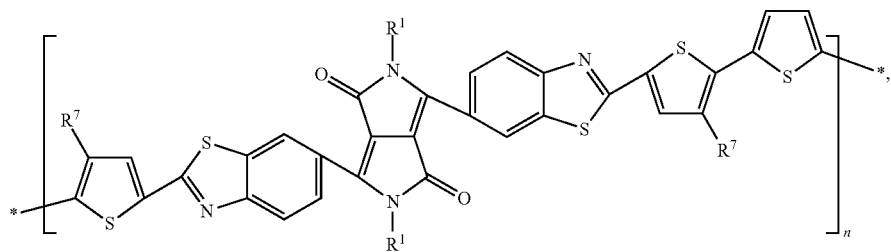
such as, for example,
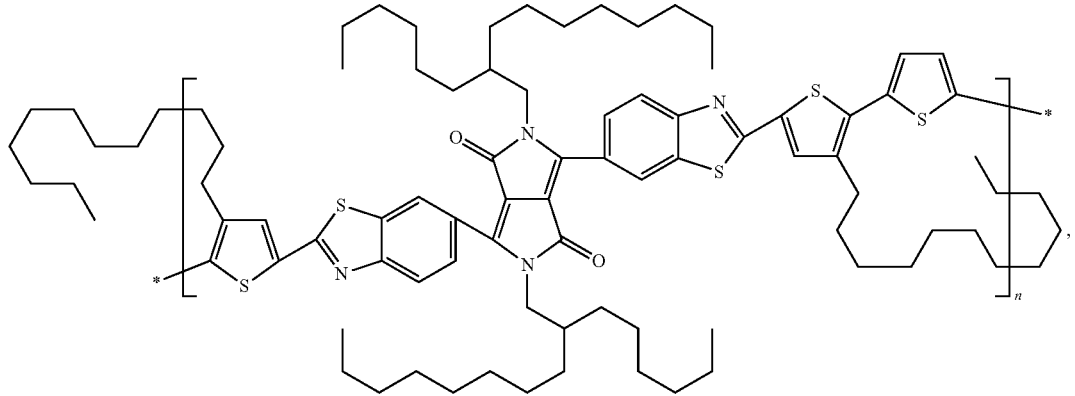
(C-4)

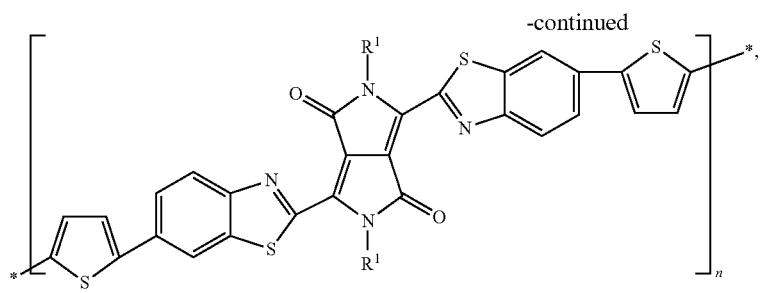
such as, for example,
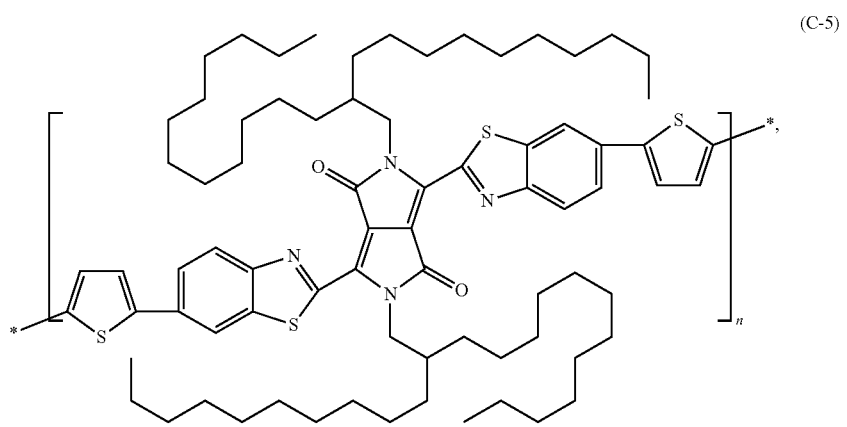
(C-5)
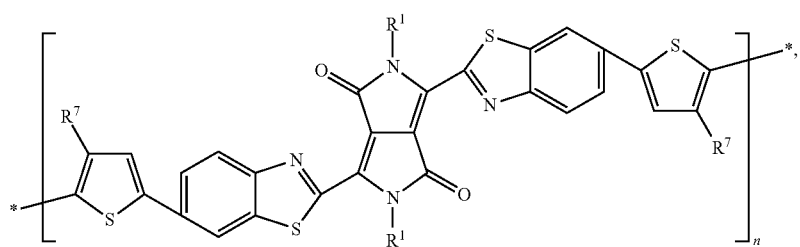
such as, for example,
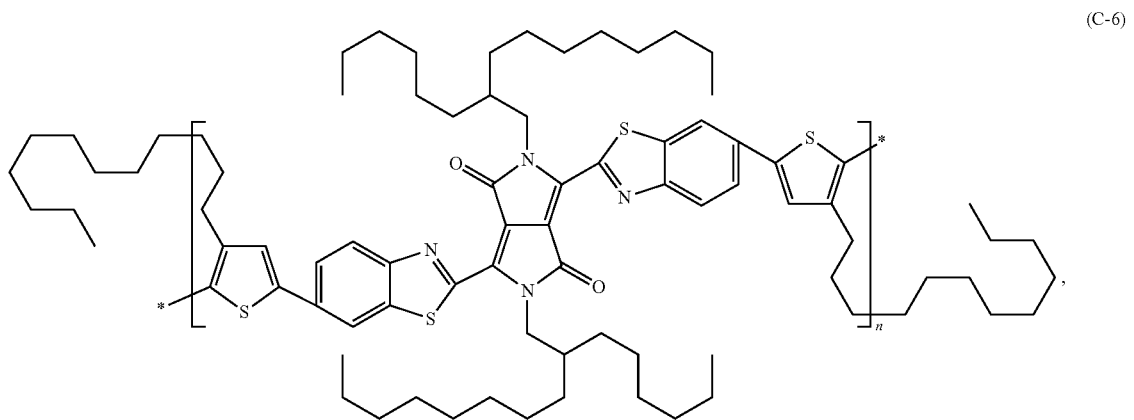
(C-6)

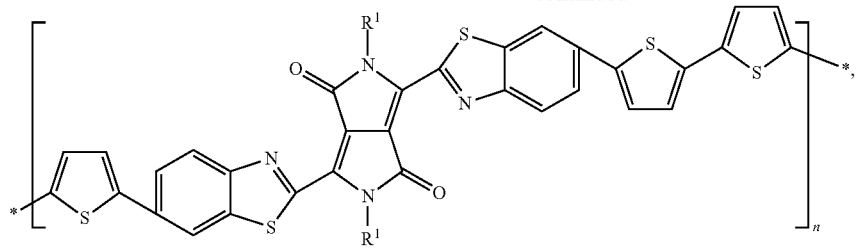
such as, for example,
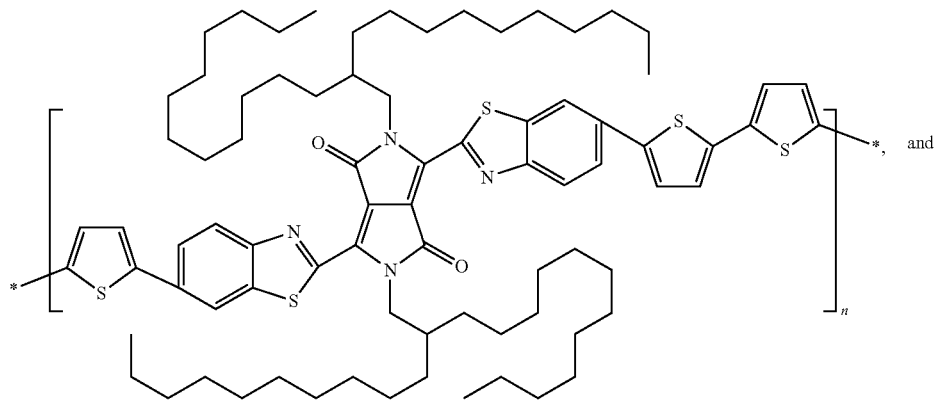
(C-7)
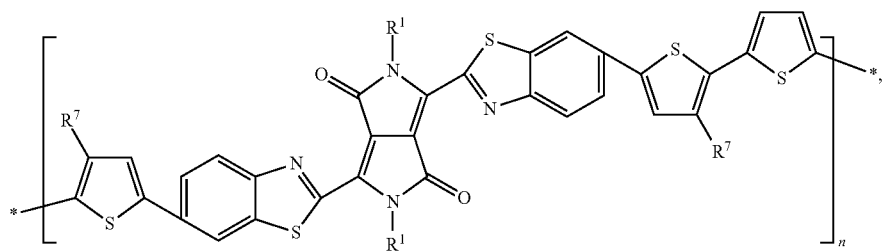
such as, for example,
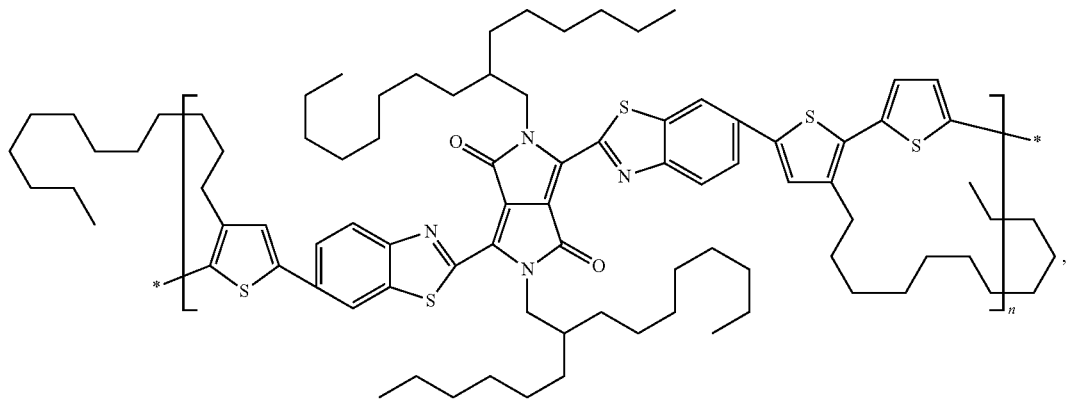
(C-8)

wherein $R^1$ and $R^7$ are as defined above. Preferably, $R^1$ is $C_1$-$C_{35}$alkyl and $R^7$ is $C_1$-$C_{25}$alkyl. Polymers C-5 to C-8 are more preferred than polymers C-1 to C-4.

Copolymers of formula *─[─A─]─[─COM$^1$─]─* can be obtained, for example, by the Suzuki reaction. The condensation reaction of an aromatic boronate and a halogenide, especially a bromide, commonly referred to as the "Suzuki reaction", is tolerant of the presence of a variety of organic functional groups as reported by N. Miyaura and A. Suzuki in Chemical Reviews, Vol. 95, pp. 457-2483 (1995). Preferred catalysts are 2-dicyclohexylphosphino-2',6'-di-alkoxybiphenyl/palladium(11)acetates, tri-alykl-phosphonium salts/palladium (0) derivatives and tri-alkylphosphine/palladium (0) derivatives. Especially preferred catalysts are 2-dicyclohexylphosphino-2',6'-di-methoxybiphenyl (sPhos)/palladium(II) acetate and, tri-tert-butylphosphonium tetrafluoroborate ((t-Bu)$_3$P*HBF$_4$)/tris(dibenzylideneacetone)dipalladium (0) (Pd$_2$(dba)$_3$) and tri-tert-butylphosphine (t-Bu)$_3$P/tris(dibenzylideneacetone)dipalladium (0) (Pd$_2$(dba)$_3$). This reaction can be applied to preparing high molecular weight polymers and copolymers.

To prepare polymers corresponding to formula *─[─A─]─[ COM$^1$─]─* a dihalogenide of formula $X^{20}$-A-$X^{20}$ is reacted with an equimolar amount of a diboronic acid or diboronate corresponding to formula $X^{21}$─[ COM$^1$─]─$X^{21}$, or
a dihalogenide of formula $X^{20}$─[ COM$^{11}$─]─$X^{20}$ is reacted with an equimolar amount of a diboronic acid or diboronate corresponding to formula $X^{21}$-A-$X^{21}$, wherein $X^{20}$ is halogen, especially Br, and $X^{21}$ is independently in each occurrence —B(OH)$_2$, —B(OY$^1$)$_2$,

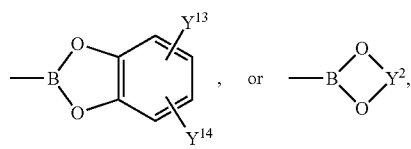

whereinY$^1$ is independently in each occurrence a $C_1$-$C_{10}$alkyl group and Y$^2$ is independently in each occurrence a $C_2$-$C_{10}$alkylene group, such as —CY$^3$Y$^4$—CY$^5$Y$^6$—, or —CY$^7$Y$^8$—CY$^9$Y$^{10}$—CY$^{11}$Y$^{12}$—, wherein Y$^3$, Y$^4$, Y$^5$, Y$^6$, Y$^7$, Y$^8$, Y$^9$, Y$^{10}$, Y$^{11}$ and Y$^{12}$ are independently of each other hydrogen, or a $C_1$-$C_{10}$alkyl group, especially —C(CH$_3$)$_2$C(CH$_3$)$_2$—, —C(CH$_3$)$_2$CH$_2$C(CH$_3$)$_2$—, or —CH$_2$C(CH$_3$)$_2$CH$_2$—, and Y$^{13}$ and Y$^{14}$ are independently of each other hydrogen, or a $C_1$-$C_{10}$alkyl group, in a solvent and in the presence of a catalyst. The reaction is typically conducted at about 0° C. to 180° C. in an aromatic hydrocarbon solvent such as toluene, xylene. Other solvents such as dimethylformamide, dioxane, dimethoxyethan and tetrahydrofuran can also be used alone, or in mixtures with an aromatic hydrocarbon. An aqueous base, preferably sodium carbonate or bicarbonate, potassium phosphate, potassium carbonate or bicarbonate is used as activation agent for the boronic acid, boronate and as the HBr scavenger. A polymerization reaction may take 0.2 to 100 hours. Organic bases, such as, for example, tetraalkylammonium hydroxide, and phase transfer catalysts, such as, for example TBAB, can promote the activity of the boron (see, for example, Leadbeater & Marco; Angew. Chem. Int. Ed. Eng. 42 (2003) 1407 and references cited therein). Other variations of reaction conditions are given by T. I. Wallow and B. M. Novak in J. Org. Chem. 59 (1994) 5034-5037; and M. Remmers, M. Schulze, and G. Wegner in Macromol. Rapid Commun. 17 (1996) 239-252.

Control of molecular weight is possible by using either an excess of dibromide, diboronic acid, or diboronate, or a chain terminator.

If desired, a monofunctional halide, boronate, such as, for example, a monofunctional aryl halide, or aryl boronate, may be used as a chain-terminator in such reactions, which will result in the formation of a terminal aryl group:

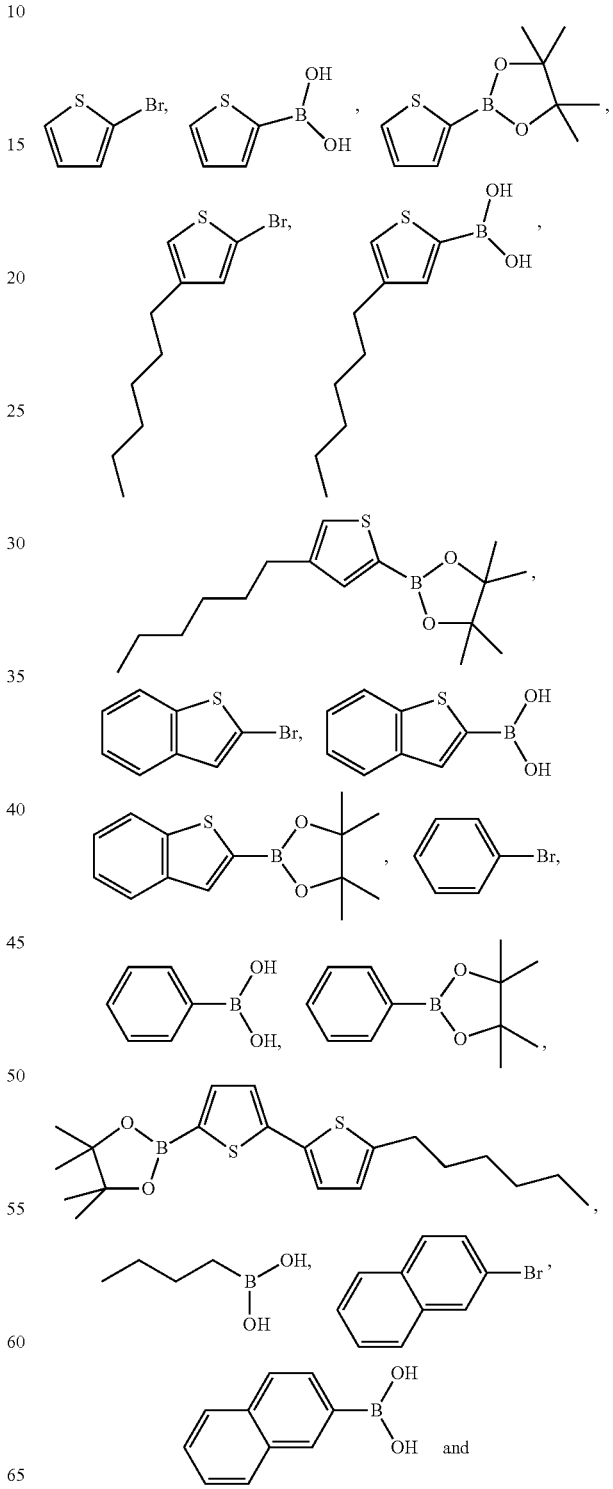

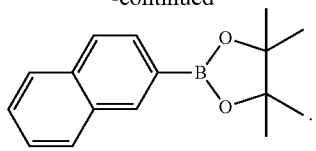

It is possible to control the sequencing of the monomeric units in the resulting copolymer by controlling the order and composition of monomer feeds in the Suzuki reaction.

The polymers of the present invention can also be synthesized by the Stille coupling (see, for example, Babudri et al, J. Mater. Chem., 2004, 14, 11-34; J. K. Stille, Angew. Chemie Int. Ed. Engl. 1986, 25, 508). To prepare polymers corresponding to formula II a dihalogenide of formula $X^{20}$-A-$X^{20}$ is reacted with an equimolar amount of an organo tin compound corresponding to formula $X^{21*}$—$COM^1$—$X^{21*}$, or a dihalogenide of formula $X^{20}$—$COM^1$—$X^{20}$ is reacted with an equimolar amount of an organo tin compound corresponding to formula $X^{21*}$-A-$X^{21*}$, wherein $X^{21'}$ is independently in each occurrence —$SnR^{207}R^{208}R^{209}$, wherein $R^{207}$, $R^{208}$ and $R^{209}$ are identical or different and are H or $C_1$-$C_6$alkyl, or two of the groups $R^{207}$, $R^{208}$ and $R^{209}$ form a ring and these groups are optionally branched, in an inert solvent at a temperature in range from 0° C. to 200° C. in the presence of a palladium-containing catalyst. It must be ensured here that the totality of all monomers used has a highly balanced ratio of organotin functions to halogen functions. In addition, it may prove advantageous to remove any excess reactive groups at the end of the reaction by end-capping with monofunctional reagents. In order to carry out the process, the tin compounds and the halogen compounds are preferably introduced into one or more inert organic solvents and stirred at a temperature of from 0 to 200° C., preferably from 30 to 170° C. for a period of from 1 hour to 200 hours, preferably from 5 hours to 150 hours. The crude product can be purified by methods known to the person skilled in the art and appropriate for the respective polymer, for example repeated re-precipitation or even by dialysis.

Suitable organic solvents for the process described are, for example, ethers, for example diethyl ether, dimethoxyethane, diethylene glycol dimethyl ether, tetrahydrofuran, dioxane, dioxolane, diisopropyl ether and tert-butyl methyl ether, hydrocarbons, for example hexane, cyclohexane, heptane, cyclohexane, benzene, toluene and xylene, alcohols, for example methanol, ethanol, 1-propanol, 2-propanol, ethylene glycol, 1-butanol, 2-butanol and tert-butanol, ketones, for example acetone, ethyl methyl ketone and isobutyl methyl ketone, amides, for example dimethylformamide (DMF), dimethylacetamide and N-methylpyrrolidone, nitriles, for example acetonitrile, propionitrile and butyronitrile, and mixtures thereof.

The palladium and phosphine components should be selected analogously to the description for the Suzuki variant.

Alternatively, the polymers of the present invention can also be synthesized by the Negishi reaction using zinc reagents A-$(ZnX^{22})_2$, wherein $X^{22}$ is halogen and halides, and $COM^1$-$(X^{23})_2$, wherein $X^{23}$ is halogen or triflate, or using A-$(X^{23})_2$, and $COM^1$-$(ZnX^{23})_2$. Reference is, for example, made to E. Negishi et al., Heterocycles 18 (1982) 117-22.

Alternatively, the polymers of the present invention can also be synthesized by the Hiyama reaction using organosilicon reagents A-$(SiR^{210}R^{211}R^{212})_2$, wherein $R^{210}$, $R^{211}$ and $R^{212}$ are identical or different and are halogen, $C_1$-$C_6$alkyl and $COM^1$-$(X^{23})_2$, wherein $X^{23}$ is halogen or triflate, or using A-$(X^{23})_2$ and $COM^1$-$(SiR^{210}R^{211}R^{212})_2$. Reference is, for example, made to T. Hiyama et al., Pure Appl. Chem. 66 (1994) 1471-1478 and T. Hiyama et al., Synlett (1991) 845-853.

Homopolymers of the type $(A)_n$ can be obtained via Yamamoto coupling of dihalides $X^{20}$-A-$X^{20}$, where $X^{20}$ is halogen, preferably bromide. Alternatively homopolymers of the type $(A)_n$ can be obtained via oxidative polymerization of units $X^{20'}$-A-$X^{20'}$, where $X^{20'}$ is hydrogen, e.g. with $FeCl_3$ as oxidizing agent.

The general terms used above have the following meanings:

An aliphatic hydrocarbon group having up to 25 carbon atoms is a linear or branched alkyl, alkenyl or alkynyl (also spelled alkinyl) group having up to 25 carbon atoms ($C_1$-$C_{25}$alkyl group).

Examples for $C_1$-$C_{25}$alkyl ($C_1$-$C_{18}$alkyl) groups are methyl, ethyl, n-propyl, isopropyl, n-butyl, sec.-butyl, isobutyl, tert.-butyl, n-pentyl, 2-pentyl, 3-pentyl, 2,2-dimethylpropyl, 1,1,3,3-tetramethylpentyl, n-hexyl, 1-methylhexyl, 1,1,3,3,5,5-hexamethylhexyl, n-heptyl, isoheptyl, 1,1,3,3-tetramethylbutyl, 1-methylheptyl, 3-methylheptyl, n-octyl, 3,7-dimethyl-octyl, 1,1,3,3-tetramethylbutyl, 2-ethylhexyl, 2-n-butyl-hexyl, n-nonyl, decyl, 2-hexyl-decyl, undecyl, dodecyl, tridecyl, tetradecyl, 2-decyl-tetradecyl, pentadecyl, hexadecyl, heptadecyl, octadecyl, eicosyl, heneicosyl, docosyl, tetracosyl and pentacosyl, of which 2-decyl-tetradecyl is especially preferred as a meaning of $R^1$ and $R^2$.

Examples for $C_2$-$C_{25}$alkenyl groups are vinyl, allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, isododecenyl, n-dodec-2-enyl or n-octadec-4-enyl.

Examples for $C_{2-25}$alkynyl groups are ethynyl, 1-propyn-3-yl, 1-butyn-4-yl, 1-pentyn-5-yl, 2-methyl-3-butyn-2-yl, 1,4-pentadiyn-3-yl, 1,3-pentadiyn-5-yl, 1-hexyn-6-yl, cis-3-methyl-2-penten-4-yn-1-yl, trans-3-methyl-2-penten-4-yn-1-yl, 1,3-hexadiyn-5-yl, 1-octyn-8-yl, 1-nonyn-9-yl, 1-decyn-10-yl, or 1-tetracosyn-24-yl.

Aliphatic groups can, in contrast to aliphatic hydrocarbon groups, be substituted by any acyclic substituents, but are preferably unsubstituted. Preferred substituents are $C_1$-$C_8$alkoxy or $C_1$-$C_8$alkylthio groups as exemplified further below. The term "aliphatic group" comprises also alkyl groups wherein certain non-adjacent carbon atoms are replaced by oxygen, like —$CH_2$—O—$CH_2$—$CH_2$—O—$CH_3$. The latter group can be regarded as methyl substituted by —O—$CH_2$—$CH_2$—O—$CH_3$.

A cycloalkyl group is typically $C_5$-$C_{12}$cycloalkyl, such as cyclopentyl, cyclohexyl, cycloheptyl, cyclooctyl, cyclononyl, cyclodecyl, cycloundecyl, cyclododecyl, preferably cyclopentyl, cyclohexyl, cycloheptyl, or cyclooctyl, which may be unsubstituted or substituted by one or more aliphatic and/or cycloaliphatic hydrocarbon groups and/or condensed with phenyl groups as defined herein and/or condensed with phenyl groups.

An aliphatic hydrocarbon group having up to 25 carbon atoms $R^5$ is a linear or branched alkyl, alkenyl or alkynyl (also spelled alkinyl) group having up to 25 carbon atoms as exemplified above.

Alkylene is bivalent alkyl, i.e. alkyl having two (instead of one) free valencies, e.g. trimethylene or tetramethylene.

Alkenylene is bivalent alkenyl, i.e. alkenyl having two (instead of one) free valencies, e.g. —$CH_2$—CH=CH—$CH_2$—.

A bivalent group of the formula II wherein two vicinal groups $R^5$ together represent alkylene or alkenylene having up to 7 carbon atoms, it being possible that two groups $R^5$ present in the group of formula II differ from each other, is for example a group of the formula

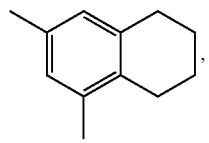
(XXV),

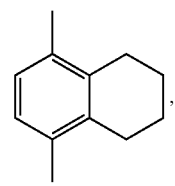
(XXVI),

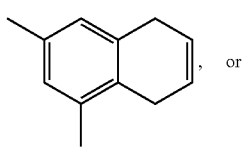
(XXVII), or

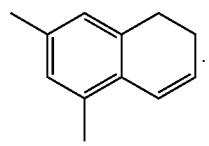
(XXVIII).

$C_1$-$C_{25}$alkoxy ($C_1$-$C_{18}$alkoxy), as represented e.g. by $R^6$, $R^7$, $R^8$, $R^9$, $R^{12}$, $R^{13}$, $R^{15}$, $R^{16}$, $R^{17}$, $R^{18}$, $R^{19}$, $R^{20}$ and $R^{21}$ to $R^{26}$, is e.g. methoxy, ethoxy, n-propoxy, isopropoxy, n-butoxy, sec.-butoxy, isobutoxy, tert.-butoxy, n-pentoxy, 2-pentoxy, 3-pentoxy, 2,2-dimethylpropoxy, n-hexoxy, n-heptoxy, n-octoxy, 1,1,3,3-tetramethylbutoxy, 2-ethylhexoxy, n-nonoxy, decoxy, undecoxy, dodecoxy, tridecoxy, tetradecoxy, pentadecoxy, hexadecoxy, heptadecoxy, and octadecoxy, preferably $C_1$-$C_4$alkoxy. The term "alkylthio group" means the same groups as the alkoxy groups, except that the oxygen atom of ether linkage is replaced by a sulfur atom.

$C_6$-$C_{24}$aryl is e.g. substituted or preferably unsubstituted phenyl, indenyl, azulenyl, naphthyl, biphenyl, as-indacenyl, s-indacenyl, acenaphthylenyl, fluorenyl, phenanthryl, fluoranthenyl, triphenlenyl, chrysenyl, naphthacen, picenyl, perylenyl, pentaphenyl, hexacenyl, pyrenyl, or anthracenyl, preferably phenyl, 1-naphthyl, 2-naphthyl, 3- or 4-biphenyl, 9-phenanthryl, 2- or 9-fluorenyl, 3- or 4-biphenyl, which all may be unsubstituted or substituted, e.g. by alkyl or alkoxy.

$C_7$-$C_{25}$aralkyl, as represented e.g. by $R^6$, $R^7$, $R^8$, $R^9$, $R^{12}$, $R^{13}$, $R^{15}$, $R^{16}$, $R^{17}$, $R^{18}$, $R^{19}R^{20}$, $R^{21}$, $R^{27}$, or $R^{28}$ is e.g. phenyl-alkyl, like benzyl, 2-benzyl-2-propyl, p-phenyl-ethyl, α,α-dimethylbenzyl, 3-phenyl-propyl, ω-phenyl-butyl, ω,ω-dimethyl-ω-phenyl-butyl, ω-phenyl-dodecyl, ω-phenyl-octadecyl, ω-phenyl-eicosyl, and ω-phenyl-docosyl, wherein the phenyl moiety may be unsubstituted or substituted, e.g. by alkyl, alkoxy or halogen. A preferred meaning for $C_7$-$C_{25}$aralkyl, as represented by $R^6$, $R^7$, $R^{27}$, or $R^{28}$ is e.g. 3-phenyl-propyl. A heteroaromatic group having up to 49, preferably up to 25 carbon atoms is a heteroaryl group as defined below, but not having more than 49, preferably not more than 25 carbon atoms. Heteroaryl is e.g. $C_2$-$C_{26}$heteroaryl, i.e. e.g. a ring with five to seven ring atoms or a condensed ring system, wherein nitrogen, oxygen or sulfur are the possible hetero atoms, and is typically an unsaturated heterocyclic group with five to 30 atoms (including both carbon and hetero atoms) having at least six conjugated π-electrons, such as thienyl, benzo[b]thienyl, dibenzo[b,d]thienyl, thianthrenyl, furyl, furfuryl, 2H-pyranyl, benzofuranyl, isobenzofuranyl, dibenzofuranyl, phenoxythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, chinolyl, isochinolyl, phthalazinyl, naphthyridinyl, chinoxalinyl, chinazolinyl, cinnolinyl, pteridinyl, carbazolyl, carbolinyl, benzotriazolyl, benzoxazolyl, phenanthridinyl, acridinyl, pyrimidinyl, phenanthrolinyl, phenazinyl, isothiazolyl, phenothiazinyl, isoxazolyl, furazanyl or phenoxazinyl, which can be unsubstituted or substituted, e.g. by alkyl.

Aliphatic groups can, in contrast to aliphatic hydrocarbon groups, be substituted by any acyclic substituents, but are preferably unsubstituted. Preferred substituents are $C_1$-$C_8$alkoxy or $C_1$-$C_8$alkylthio groups as exemplified further below. The term "aliphatic group" comprises also alkyl groups wherein certain non-adjacent carbon atoms are replaced by oxygen, like —CH$_2$—O—CH$_2$—CH$_2$—O—CH$_3$. The latter group can be regarded as methyl substituted by —O—CH$_2$—CH$_2$—O—CH$_3$.

A cycloaliphatic hydrocarbon group is a cycloalkyl or cycloalkenyl group which may be substituted by one or more aliphatic and/or cycloaliphatic hydrocarbon groups.

A cycloaliphatic-aliphatic group is an aliphatic group substituted by a cycloaliphatic group, wherein the terms "cycloaliphatic" and "aliphatic" have the meanings given herein and wherein the free valency extends from the aliphatic moiety. Hence, a cycloaliphatic-aliphatic group is for example a cycloalkyl-alkyl group.

A cycloalkyl-alkyl group is an alkyl group substituted by a cycloalkyl group, e.g. cyclohexyl-methyl.

A "cycloalkenyl group" means an unsaturated alicyclic hydrocarbon group containing one or more double bonds, such as cyclopentenyl, cyclopentadienyl, cyclohexenyl and the like, which may be unsubstituted or substituted by one or more aliphatic and/or cycloaliphatic hydrocarbon groups and/or condensed with phenyl groups.

For example, a cycloalkyl or cycloalkenyl group, in particular a cyclohexyl group, can be condensed one or two times with phenyl which can be substituted one to three times with $C_1$-$C_4$-alkyl. Examples of such condensed cyclohexyl groups are groups of the formulae:

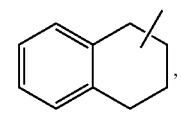
(XXIa),

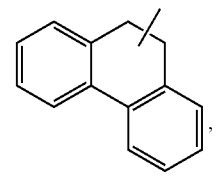
(XXIb),

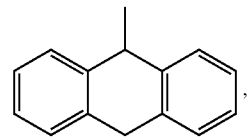
(XXII)

in particular

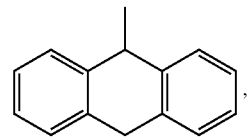

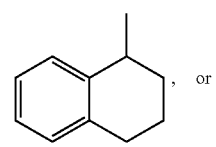
(XXIII), or

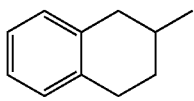
(XXIV)

which can be substituted in the phenyl moieties one to three times with $C_1$-$C_4$-alkyl.

Preferred substituents of a substituted cycloaliphatic hydrocarbon group are e.g. $C_1$-$C_8$alkoxy or $C_1$-$C_8$alkylthio groups.

$C_2$-$C_{18}$alkylenedioxy in which carbon atoms which are not adjacent to oxygen may be replaced by oxygen is e.g. a group of the formula —O—$CH_2$—O—$CH_2$—$CH_2$—O—.

An aliphatic, cycloaliphatic, cycloaliphatic-aliphatic, aromatic, aromatic-aliphatic, heteroaromatic or heteroaromatic-aliphatic group having up to 25 carbon atoms as substituent $R^{22}$ to $R^{26}$ of a group of the formula XI has the meanings defined above. A preferred group of the formula XI is the 4-biphenyl group, which may be unsubstituted or substituted within the scope of the above terms.

A bivalent group of the formula IV wherein $R^6$ and $R^7$ together represent alkylene or alkenylene which may be both bonded via oxygen and/or sulfur to the thienyl residue and which may both have up to 25 carbon atoms, is e.g. a group of the formula

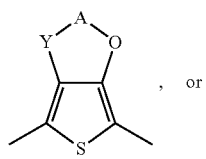
(XXIX)

, or

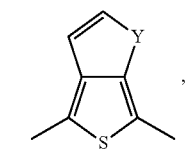
(XXX)

wherein A represents linear or branched alkylene having up to 25 carbon atoms, preferably ethylene or propylene which may be substituted by one or more alkyl groups, and Y represents oxygen or sulphur. For example, the bivalent group of the formula —Y-A-O— represents —O—$CH_2$—$CH_2$—O— or —O—$CH_2$—$CH_2$—$CH_2$—O—.

A bivalent group of the formula VI wherein $R^{10}$ and $R^{11}$ together represent oxo is a group of the formula

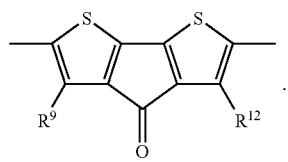
(XXXI)

$C_1$-$C_{18}$alkoxy in which carbon atoms which are not adjacent to oxygen may be replaced by oxygen is e.g. a group of one of the formulae —O—$CH_2$—O—$CH_2$—$CH_2$—O—$CH_3$, —O—$(CH_2)_2OCH_3$, —O—$(CH_2CH_2O)_2CH_2CH_3$, —O—$CH_2$—O—$CH_3$, —O—$CH_2CH_2$—O—$CH_2CH_3$, —O—$CH_2CH_2CH_2$—O—$CH(CH_3)_2$, —O—$[CH_2CH_2O]_{n'}$—$CH_3$ wherein n'=1-10, —O—$CH_2$—$CH(CH_3)$—O—$CH_2$—$CH_2CH_3$ and —O—$CH_2$—$CH(CH_3)$—O—$CH_2$—$CH_3$.

The term "carbamoyl group" is typically a $C_{1-18}$carbamoyl radical, preferably $C_{1-8}$carbamoyl radical, which may be unsubstituted or substituted, such as, for example, carbamoyl, methylcarbamoyl, ethylcarbamoyl, n-butylcarbamoyl, tert-butylcarbamoyl, dimethylcarbamoyloxy, morpholinocarbamoyl or pyrrolidinocarbamoyl.

Halogen is fluoro, chloro, bromo or iodo.

A group of the formula XI wherein two groups $R^{22}$ to $R^{26}$ which are in the neighborhood of each other, together represent alkylene or alkenylene having up to 8 carbon atoms, thereby forming a ring, is e.g. a group of the formula

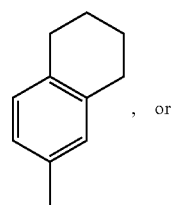
(XXXII)

, or

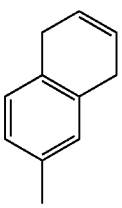
(XXXIII)

, wherein in the group of the formula XXXII $R^{23}$ and $R^{24}$ together represent 1,4-butylene and in the group of the formula XXXIII $R^{23}$ and $R^{24}$ together represent 1,4-but-2-enylene.

A group of the formula XII, wherein $R^{27}$ and $R^{28}$ together represent alkylene or alkenylene which may be both bonded via oxygen and/or sulfur to the thienyl residue and which may both have up to 25 carbon atoms, is e.g. a group of the formula

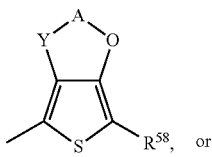
(XXXIV)

, or

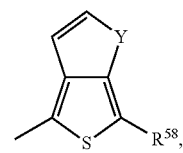
(XXXV)

wherein A represents linear or branched alkylene having up to 25 carbon atoms, preferably ethylene or propylene which may be substituted by one or more alkyl groups, and Y represents oxygen or sulphur. For example, the bivalent group of the formula —Y-A-O— represents —O—$CH_2$—$CH_2$—O— or —O—$CH_2$—$CH_2$—$CH_2$—O—.

The compounds of the formula I can be manufactured by known methods.

A possible route of manufacture starts from a compound of the formula

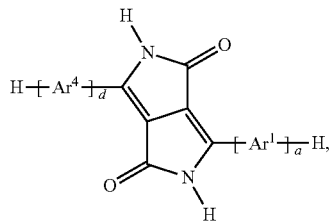

(XXXIV)

wherein a and d represent 1 and $Ar^1$ and $Ar^4$ have the meanings given above, or from a compound of the formula

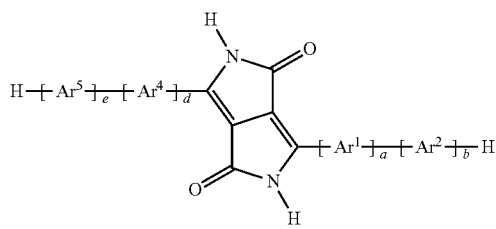

(XXXV)

wherein a and d represent 1, b and e represent 1, and $Ar^1$, $Ar^4$, $Ar^2$ and $Ar^5$ have the meanings given above.

Said starting compounds of the formulae XXXIV and XXXV can be obtained as described in U.S. Pat. No. 4,579,949 by reacting (in the presence of a strong base) one mole of a disuccinate, like dimethyl succinate, with 1 mole of a nitrile of the formulae H—$Ar^1$—CN (XXXVI), or H—$Ar^4$—CN (XXXVII), or 1 mole of a nitrile of the formulae H—$Ar^2$—$Ar^1$—CN (XXXVIII), or H—$Ar^5$—$Ar^4$—CN (XXXIX).

Alternatively, said starting compounds of the formulae XXXIV and XXXV can be obtained as described in U.S. Pat. No. 4,659,775 by reacting a nitrile with a suitable ester, like a pyrrolinon-3-carboxylic ester derivative.

The thus obtained compound of the formula XXXIV or the thus obtained compound of the formula XXXV is then N-alkylated for introduction of the groups $R^1$ and $R^2$, e.g. by reaction with a bromide of the formula $R^1$—Br or $R^2$—Br in the presence of a suitable base, like potassium carbonate, in a suitable solvent, like N-methyl-pyrrolidone. The reaction is carried out at a temperature from about room temperature to about 180° C., preferably from about 100° C. to about 170° C., e.g. at 140° C.

The thus obtained compound of the formula XL

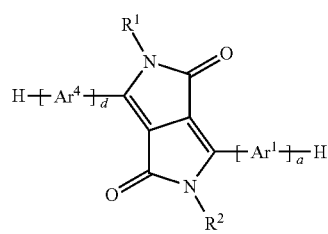

(XL)

wherein a and d represent 1, and $R^1$, $R^2$, $Ar^1$ and $Ar^4$ have the meanings given above, or the thus obtained compound of the formula XLI

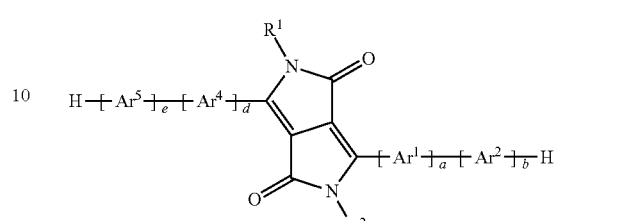

(XLI)

wherein a and d represent 1, b and e represent 1, and $R^1$, $R^2$, $Ar^2$ and $Ar^5$ have the meanings given above, is then reacted with a suitable brominating agent, like N-bromo-succinimide, to yield a compound of the formulae

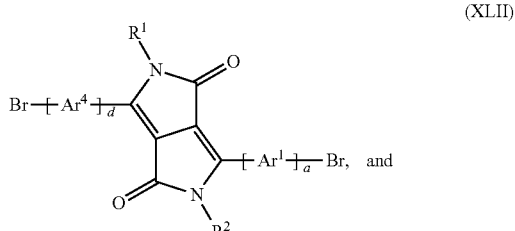

(XLII)

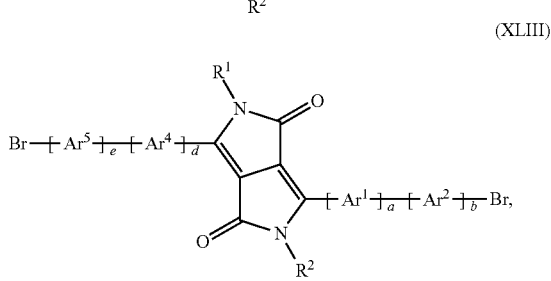

(XLIII)

respectively.

The bromination is carried out in a suitable solvent, like chloroform, using two equivalents of N-bromo-succinimide at a temperature between −30° C. and +50° C., preferably between −10° C. and room temperature, e.g. at 0° C.

The compounds of the formulae XLII or XLIII can then be "side-chain-elongated", by step-wise adding further groups $Ar^2$—H, $Ar^5$—H, $Ar^3$—$R^3$, and $Ar^6$—$R^4$. The step-wise addition of these groups can be effected e.g. by reacting a compound of the formulae XLII or XLIII with a suitable tin compound of the formula $(R^{59})_3$Sn—Ar (XLIV), wherein $R^{59}$ represents $C_{1-7}$alkyl, like butyl, and Ar represents $Ar^2$—H, $Ar^5$—H, $Ar^3$—$R^3$, or $Ar^6$—$R^4$.

The reaction is carried out in the presence of a suitable palladium catalyst, like $Pd(P[C_6H_5]_3)_4$, in a suitable solvent, e.g. an aromatic hydrocarbon solvent, like toluene, at a temperature between about 50° C. and 180° C., e.g. under reflux, and under inert conditions including, inter alia, the use of dry solvents. After cooling down, the reaction mixture may be e.g. filtrated, e.g. on a double layer silica gel/Hyflo®, concentrated and the desired compound precipitated, e.g. by addition of methanol.

The "side-chain-elongation" of the compounds of the formulae XLII or XLIII with an additional thienyl residue can also be effected e.g. by reaction with a mixture of 2-thienylboronic acid pinacol ester, $Pd_2(dba)_3$[tris(dibenzylideneacetone)-di-palladium)] and tri-tert-butyl-phosphonium-tetrafluoroborate in tetrahydrofurane.

The 2-thienylboronic acid pinacol ester may be obtained e.g. by adding substituted or unsubstituted thiophene to a mixture prepared from n-butyl-lithium and diisopropylamine and by adding 2-isopropoxy-4,4,5,5-tetramethyl-1,3,2-dioxaborolane to the thus obtained mixture.

Analogously, the "side-chain-elongation" of the compounds of the formulae XLII or XLIII with an additional phenyl or biphenyl residue may be effected with phenyl-boronic acid pinacol ester or biphenyl-boronic acid pinacol ester.

Alternatively, for the manufacture of compounds of the formula I wherein the side chains of the formulae

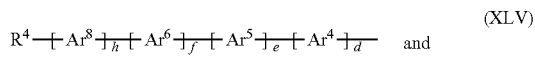  (XLV)

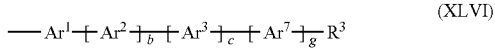  (XLVI)

are identical to each other, it is also possible to build up the complete side chains first and then reacting a nitrile of the formula

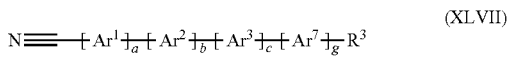  (XLVII)

with a suitable disuccinate, e.g. di-tert-amyl succinate. For example, a mixture of iron(III)chloride ($FeCl_3$), sodium, and tert-amylalcohol may be heated to 60-160° C., e.g. 110° C., before a mixture of the nitrile of the formula XLVII and di-tert-amyl succinate is added drop wise. After stirring the reaction mixture until the reaction is complete, e.g. for about 19 hours at 110° C., the reaction mixture is poured onto a water-methanol mixture.

Compounds of the formulae

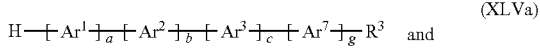  (XLVa)

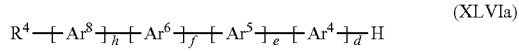  (XLVIa)

containing the complete side chains can be manufactured e.g. by reacting a bromo derivative of the formula Br—$Ar^1$ etc. first with magnesium in diethyl ether and then adding the thus obtained Grignard solution to a solution in diethyl ether of Ni(dppp)$Cl_2$ and a mono- or, if desired, dibromo compound of the formula Br—$Ar^2$ or Br—$Ar^2$—Br, respectively, etc.

The conversion of a compound of the formula XLVIa into the nitrile of the formula XLVII may be effected e.g. by adding a solution of a compound of the formula XLVIa, e.g. in toluene, to the reaction mixture obtained by adding triflic anhydride to a solution of N-formylmethylaniline in e.g. toluene, and reacting the obtained aldehyde of the formula

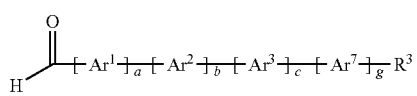  (XLVIII)

with hydroxylamine sulfate in e.g. dimethyl formamide.

The thus obtained compound of the formula I wherein $R^1$ and $R^2$ are hydrogen may then be transformed into a desired end product of the formula I wherein $R^1$ and $R^2$ are e.g. an aliphatic, cycloaliphatic, cycloaliphatic-aliphatic, or aromatic-aliphatic group, like especially such an hydrocarbon group, by N-alkylation, e.g. analogously as described above, or by heating a solution thereof and potassium carbonate in dimethyl formamide followed by addition of $R^1$—Br or $R^2$—Br, or by reaction with a suitable iodide of the formula $R^1$—I or $R^2$—I. For example, a mixture of a compound of the formula I wherein $R^1$ and $R^2$ are hydrogen in N-methylpyrrolidone is treated, preferably under cooling, e.g. to a temperature between about 0° C. and 10° C., e.g. about 5° C., with a suitable strong base, e.g. a suitable hydride, like an alkali metal hydride, e.g. sodium hydride. Thereafter, the iodide of the formula $R^1$—I or $R^2$—I is added. $R^1$ and $R^2$ are preferably identical.

The present invention relates also to new starting materials, especially to compounds of the formula I wherein one or both of $R^1$ and $R^2$ are hydrogen, preferably to such compounds which, like the end products of the formula I can also be used as the semiconductor layer in semiconductor devices.

The compounds of the formula I show clear p-type transistor behavior and can be used as the semiconductor layer in semiconductor devices. Accordingly, the present invention also relates to a semiconductor device comprising as a semiconducting effective means a compound of the formula I.

The invention relates especially to a semiconductor device comprising as as a semiconducting effective means a compound of the formula I described in the Examples selected from the compounds having the formulae A-1 to A-54, respectively, which are depicted in claim 10.

Preferably, the invention relates to a semiconductor device comprising as a semiconducting effective means a compound of the general formula I selected from the compounds having the formulae A-1 to A-54, respectively, which are depicted in claim 10.

Preferably said semiconductor device is a diode, a photodiode, a sensor, an organic field effect transistor (OFET), a transistor for flexible displays, or a solar cell, or a device containing a diode and/or an organic field effect transistor, and/or a solar cell. There are numerous types of semiconductor devices. Common to all is the presence of one or more semiconductor materials. Semiconductor devices have been described, for example, by S. M. Sze in Physics of Semiconductor Devices, $2^{nd}$ edition, John Wiley and Sons, New York (1981). Such devices include rectifiers, transistors (of which there are many types, including p-n-p, n-p-n, and thin-film transistors), light emitting semiconductor devices (for example, organic light emitting diodes in display applications or backlight in e.g. liquid crystal displays), photoconductors, current limiters, solar cells, thermistors, p-n junctions, field-effect diodes, Schottky diodes, and so forth. In each semiconductor device, the semiconductor material is combined with one or more metals and/or insulators to form the device. Semiconductor devices can be prepared or manufactured by known methods such as, for example, those described by Peter Van Zant in Microchip Fabrication, Fourth Edition, McGraw-Hill, New York (2000). In particular, organic electronic components can be manufactured as described by D. R. Gamota et al. in Printed Organic and Molecular Electronics, Kluver Academic Publ., Boston, 2004.

A particularly useful type of transistor device, the thin-film transistor (TFT), generally includes a gate electrode, a gate dielectric on the gate electrode, a source electrode and a drain electrode adjacent to the gate dielectric, and a semiconductor layer adjacent to the gate dielectric and adjacent to the source and drain electrodes (see, for example, S. M. Sze, Physics of Semiconductor Devices, $2^{nd}$ edition, John Wiley and Sons, page 492, New York (1981)). These components can be assembled in a variety of configurations. More specifically, an organic thin-film transistor (OTFT) has an organic semiconductor layer.

Typically, a substrate supports the OTFT during manufacturing, testing, and/or use. Optionally, the substrate can provide an electrical function for the OTFT. Useful substrate materials include organic and inorganic materials. For example, the substrate can comprise silicon materials inclusive of various appropriate forms of silicon, inorganic glasses, ceramic foils, polymeric materials (for example, acrylics, polyester, epoxies, polyamides, polycarbonates, polyimides, polyketones, poly(oxy-1,4-phenyleneoxy-1,4-phenylenecarbonyl-1,4-phenylene) (sometimes referred to as poly(ether ether ketone) or PEEK), polynorbornenes, polyphenyleneoxides, poly(ethylene naphthalenedicarboxylate) (PEN), poly(ethylene terephthalate) (PET), poly(phenylene sulfide) (PPS)), filled polymeric materials (for example, fiber-reinforced plastics (FRP)), and coated metallic foils.

The gate electrode can be any useful conductive material. For example, the gate electrode can comprise doped silicon, or a metal, such as aluminum, chromium, gold, silver, nickel, palladium, platinum, tantalum, and titanium. Conductive oxides, such as indium tin oxide (ITO), or conducting inks/pastes comprised of carbon black/graphite or colloidal silver dispersions, optionally containing polymer binders can also be used. Conductive polymers also can be used, for example polyaniline or poly(3,4-ethylenedioxythiophene)/poly(styrene sulfonate) (PEDOT:PSS). In addition, alloys, combinations, and multilayers of these materials can be useful. In some OTFTs, the same material can provide the gate electrode function and also provide the support function of the substrate. For example, doped silicon can function as the gate electrode and support the OTFT.

The gate dielectric is generally provided on the gate electrode. This gate dielectric electrically insulates the gate electrode from the balance of the OTFT device. Useful materials for the gate dielectric can comprise, for example, an inorganic electrically insulating material.

The gate dielectric (insulator) can be a material, such as, an oxide, nitride, or it can be a material selected from the family of ferroelectric insulators (e.g. organic materials such as poly (vinylidene fluoride/trifluoroethylene or poly(m-xylylene adipamide)), or it can be an organic polymeric insulator (e.g. poly(methacrylate)s, poly(acrylate)s, polyimides, benzocyclobutenes (BCBs), parylenes, polyvinylalcohol, polyvinylphenol (PVP), polystyrenes, polyester, polycarbonates) as for example described in J. Veres et al. Chem. Mat. 2004, 16, 4543 or A. Facchetti et al. Adv. Mat. 2005, 17, 1705. Specific examples of materials useful for the gate dielectric include strontiates, tantalates, titanates, zirconates, aluminum oxides, silicon oxides, tantalum oxides, titanium oxides, silicon nitrides, barium titanate, barium strontium titanate, barium zirconate titanate, zinc selenide, and zinc sulphide, including but not limited to $PbZr_xTi_{1-x}O_3$ (PZT), $Bi_4Ti_3O_{12}$, $BaMgF_4$, $Ba(Zr_{1-x}Ti_x)O_3$ (BZT). In addition, alloys, hybrid materials (e.g. polysiloxanes or nanoparticle-filled polymers) combinations, and multilayers of these materials can be used for the gate dielectric. The thickness of the dielectric layer is, for example, from about 10 to 1000 nm, with a more specific thickness being about 100 to 500 nm, providing a capacitance in the range of 0.1-100 nanofarads (nF).

The source electrode and drain electrode are separated from the gate electrode by the gate dielectric, while the organic semiconductor layer can be over or under the source electrode and drain electrode. The source and drain electrodes can be any useful conductive material favourably providing a low resistance ohmic contact to the semiconductor layer. Useful materials include most of those materials described above for the gate electrode, for example, aluminum, barium, calcium, chromium, gold, silver, nickel, palladium, platinum, titanium, polyaniline, PEDOT:PSS, other conducting polymers, alloys thereof, combinations thereof, and multilayers thereof. Some of these materials are appropriate for use with n-type semiconductor materials and others are appropriate for use with p-type semiconductor materials, as is known in the art.

The thin film electrodes (that is, the gate electrode, the source electrode, and the drain electrode) can be provided by any useful means such as physical vapor deposition (for example, thermal evaporation or sputtering) or (ink jet) printing methods. The patterning of these electrodes can be accomplished by known methods such as shadow masking, additive photolithography, subtractive photolithography, printing, microcontact printing, and pattern coating.

The present invention further provides a thin film transistor device comprising
a plurality of electrically conducting gate electrodes disposed on a substrate;
a gate insulator layer disposed on said electrically conducting gate electrodes;
a plurality of sets of electrically conductive source and drain electrodes disposed on said insulator layer such that each of said sets is in alignment with each of said gate electrodes;
an organic semiconductor layer disposed in the channel between source and drain electrodes on said insulator layer substantially overlapping said gate electrodes; wherein
said organic semiconductor layer comprise a compound of the formula I.

The present invention further provides a process for preparing a thin film transistor device comprising the steps of:
depositing a plurality of electrically conducting gate electrodes on a substrate;
depositing a gate insulator layer on said electrically conducting gate electrodes;
depositing a plurality of sets of electrically conductive source and drain electrodes on said layer such that each of said sets is in alignment with each of said gate electrodes;
depositing a layer comprising a compound of the formula I on said insulator layer such that said layer comprising the compound of formula I substantially overlaps said gate electrodes, thereby producing the thin film transistor device.

The above-mentioned layer comprising a compound of formula I may additionally comprise at least another material. The other material can be, but is not restricted to another compound of the formula I, a semi-conducting polymer, a polymeric binder, organic small molecules different from a compound of the formula I, carbon nanotubes, a fullerene derivative, inorganic particles (quantum dots, quantum rods, quantum tripods, $TiO_2$, ZnO etc.), conductive particles (Au, Ag etc.), and insulator materials like the ones described for the gate dielectric (PET, PS etc.). As stated above, the semiconductive layer can also be composed of a mixture of one or more small molecules of the formula I and a polymeric binder. The ratio of the small molecules of formula I to the polymeric binder can vary from 5 to 95 percent. Preferably, the polymeric binder is a semicristalline polymer such as polystyrene (PS), high-density polyethylene (HDPE), polypropylene (PP) and polymethylmethacrylate (PMMA). With this technique, a degradation of the electrical performance can be avoided (cf. WO 2008/001123 A1).

For heterojunction solar cells (bulk heterojunction solar cells) the active layer comprises preferably a mixture of a compound of the formula I and a fullerene, such as [60] PCBM (=6,6-phenyl-$C_{61}$-butyric acid methyl ester), or [70] PCBM, in a weight ratio of 1:1 to 1:3. Methanofullerene Phenyl-$C_{61}$-Butyric-Acid-Methyl-Ester ([60]PCBM), i.e. 1-[3-(methoxy-carbonyl)propyl]-1-phenyl-[6.6]$C_{61}$-3'H-cyclopropa[1,9][5,6]fullerene-$C_{60}$-lh-3'-butanoic acid 3'-phenyl methyl ester, is an effective solution processable n-type organic semiconductor. It is blended with conjugated polymers with nano-particles such as $C_{60}$.

Any suitable substrate can be used to prepare the thin films of the compounds of the formula I. Preferably, the substrate used to prepare the above thin films is a metal, silicon, plastic, paper, coated paper, fabric, glass or coated glass.

Alternatively, a TFT is fabricated, for example, by solution deposition of a compound of the formula I on a highly doped silicon substrate covered with a thermally grown oxide layer followed by vacuum deposition and patterning of source and drain electrodes.

In yet another approach, a TFT is fabricated by deposition of source and drain electrodes on a highly doped silicon substrate covered with a thermally grown oxide and then solution deposition of the compound of the formula I to form a thin film.

The gate electrode could also be a patterned metal gate electrode on a substrate or a conducting material such as a conducting polymer, which is then coated with an insulator applied either by solution coating or by vacuum deposition on the patterned gate electrodes.

Any suitable solvent can be used to dissolve, and/or disperse a compound of the formula I, provided it is inert and can be removed partly, or completely from the substrate by conventional drying means (e.g. application of heat, reduced pressure, airflow etc.). Suitable organic solvents for processing the semiconductors of the invention include, but are not limited to, aromatic or aliphatic hydrocarbons, halogenated such as chlorinated or fluorinated hydrocarbons, esters, ethers amides, such as chloroform, tetrachloroethane, tetrahydrofuran, toluene, tetraline, anisole, xylene, ethyl acetate, methyl ethyl ketone, dimethyl formamide, dichlorobenzene, trichlorobenzene, propylene glycol monomethyl ether acetate (PGMEA) and mixtures thereof. The solution, and/or dispersion is then applied by a method, such as, spin-coating, dip-coating, screen printing, microcontact printing, doctor blading or other solution application techniques known in the art on the substrate to obtain thin films of the semiconducting material.

The term "dispersion" covers any composition comprising a compound of the formula I, which is not fully dissolved in a solvent. The dispersion can be done selecting a composition including at least a compound of formula I, or a mixture containing a compound of formula I, and a solvent, wherein the polymer exhibits lower solubility in the solvent at room temperature but exhibits greater solubility in the solvent at an elevated temperature, wherein the composition gels when the elevated temperature is lowered to a first lower temperature without agitation;

dissolving at the elevated temperature at least a portion of the compound of the formula I in the solvent; lowering the temperature of the composition from the elevated temperature to the first lower temperature; agitating the composition to disrupt any gelling, wherein the agitating commences at any time prior to, simultaneous with, or subsequent to the lowering the elevated temperature of the composition to the first lower temperature; depositing a layer of the composition wherein the composition is at a second lower temperature lower than the elevated temperature; and drying at least partially the layer.

The dispersion can also be constituted of (a) a continuous phase comprising a solvent, a binder resin, and optionally a dispersing agent, and (b) a disperse phase comprising a compound of formula I, or a mixture containing a compound of formula I of the present invention. The degree of solubility of the compound of formula I in the solvent may vary for example from 0.5% to about 20% solubility, particularly from 1% to about 5% solubility.

Preferably, the thickness of the organic semiconductor layer is in the range of from about 5 to about 1000 nm, especially the thickness is in the range of from about 10 to about 100 nm.

The compounds of the formula I can be used alone or in combination as the organic semiconductor layer of the semiconductor device. The layer can be provided by any useful means, such as, for example, vapor deposition and printing techniques. The compounds of the formula I which are sufficiently soluble in organic solvents can be solution deposited and patterned (for example, by spin coating, dip coating, ink jet printing, gravure printing, flexo printing, offset printing, screen printing, microcontact (wave)-printing, drop or zone casting, or other known techniques).

The compounds of the formula I can be used in integrated circuits comprising a plurality of OTFTs, as well as in various electronic articles. Such articles include, for example, radio-frequency identification (RFID) tags, backplanes for flexible displays (for use in, for example, personal computers, cell phones, or handheld devices), smart cards, memory devices, sensors (e.g. light-, image-, bio-, chemo-, mechanical- or temperature sensors), especially photodiodes, or security devices and the like. Due to its ambi-polarity the material can also be used in Organic Light Emitting Transistors (OLET).

The invention provides organic photovoltaic (PV) devices (solar cells) comprising a compound of the formula I.

The PV device comprise in this order:
(a) a cathode (electrode),
(b) optionally a transition layer, such as an alkali halogenide, especially lithium fluoride,
(c) a photoactive layer,
(d) optionally a smoothing layer,
(e) an anode (electrode),
(f) a substrate.

The photoactive layer comprises the compounds of the formula I. Preferably, the photoactive layer is made of a compound of the formula I, as an electron donor and an acceptor material, like a fullerene, particularly a functionalized fullerene PCBM, as an electron acceptor. As stated above, the photoactive layer may also contain a polymeric binder. The ratio of the small molecules of formula I to the polymeric binder can vary from 5 to 95 percent. Preferably, the polymeric binder is a semicrystalline polymer such as polystyrene (PS), high-density polyethylene (HDPE), polypropylene (PP) and polymethylmethacrylate (PMMA).

The fullerenes useful in this invention may have a broad range of sizes (number of carbon atoms per molecule). The term fullerene as used herein includes various cage-like molecules of pure carbon, including Buckminsterfullerene ($C_{60}$) and the related "spherical" fullerenes as well as carbon nanotubes. Fullerenes may be selected from those known in the art ranging from, for example, $C_{20}$-$C_{1000}$. Preferably, the fullerene is selected from the range of $C_{60}$ to $C_{96}$. Most preferably the fullerene is $C_{60}$ or $C_{70}$, such as [60]PCBM, or [70]PCBM. It is also permissible to utilize chemically modified fullerenes, provided that the modified fullerene retains acceptor-type and electron mobility characteristics. The acceptor material can also be a material selected from the group consisting of another polymer of formula I or any semi-conducting polymer provided that the polymers retain acceptor-type and electron mobility characteristics, organic small molecules, carbon nanotubes, inorganic particles (quantum dots, quantum rods, quantum tripods, $TiO_2$, ZnO etc.).

The electrodes are preferably composed of metals or "metal substitutes". Herein the term "metal" is used to embrace both materials composed of an elementally pure metal, e.g., Mg, and also metal alloys which are materials composed of two or more elementally pure metals, e.g., Mg and Ag together, denoted Mg:Ag. Here, the term "metal substitute" refers to a material that is not a metal within the normal definition, but which has the metal-like properties that are desired in certain appropriate applications. Commonly used metal substitutes for electrodes and charge transfer layers would include doped wide-bandgap semiconductors, for example, transparent conducting oxides such as indium tin oxide (ITO), gallium indium tin oxide (GITO), and zinc indium tin oxide (ZITO). Another suitable metal substitute is the transparent conductive polymer polyanaline (PANI) and its chemical relatives, or PEDOT:PSS. Metal substitutes may be further selected from a wide range of non-metallic materials, wherein the term "non-metallic" is meant to embrace a wide range of materials provided that the material is free of metal in its chemically uncombined form. Highly transparent, non-metallic, low resistance cathodes or highly efficient, low resistance metallic/non-metallic compound cathodes are, for example, disclosed in U.S. Pat. No. 6,420,031 and U.S. Pat. No. 5,703,436.

The substrate can be, for example, a plastic (flexible substrate), or glass substrate.

In another preferred embodiment of the invention, a smoothing layer is situated between the anode and the photoactive layer. A preferred material for this smoothing layer comprises a film of 3,4-polyethylenedioxythiophene (PEDOT), or 3,4-polyethylenedioxythiophene:poly-styrene-sulfonate (PEDOT:PSS).

In a preferred embodiment of the present invention, the photovoltaic cell comprises, as described for example, in U.S. Pat. No. 6,933,436 a transparent glass carrier, onto which an electrode layer made of indium/tin oxide (ITO) is applied. This electrode layer generally has a comparatively rough surface structure, so that it is covered with a smoothing layer made of a polymer, typically PEDOT, which is made electrically conductive through doping. The photoactive layer is made of two components, has a layer thickness of, for example, 100 nm to a few µm depending on the application method, and is applied onto this smoothing layer. The photoactive layer is made of a compound of the formula I, as an electron donor and a fullerene, particularly functionalized fullerene PCBM, as an electron acceptor. These two components are mixed with a solvent and applied as a solution onto the smoothing layer by, for example, the spin-coating method, the drop casting method, the Langmuir-Blodgett ("LB") method, the ink jet printing method and the dripping method. A squeegee or printing method could also be used to coat larger surfaces with such a photoactive layer. Instead of toluene, which is typical, a dispersion agent such as chlorobenzene is preferably used as a solvent. Among these methods, the vacuum deposition method, the spin-coating method, the ink jet printing method and the casting method are particularly preferred in view of ease of operation and cost.

In the case of forming the layer by using the spin-coating method, the casting method and ink jet printing method, the coating can be carried out using a solution and/or dispersion prepared by dissolving, or dispersing the composition in a concentration of from 0.01 to 90% by weight in an appropriate organic solvent such as benzene, toluene, xylene, tetrahydrofurane, methyltetrahydrofurane, N,N-dimethylformamide, acetone, acetonitrile, anisole, dichloromethane, dimethylsulfoxide, chlorobenzene, 1,2-dichlorobenzene and mixtures thereof.

Before a counter electrode is applied, a thin transition layer, which must be electrically insulating, having a layer thickness of, for example, 0.6 nm, is applied to the photoactive layer. In this exemplary embodiment, this transition layer is made of an alkali halogenide, namely a lithium fluoride, which is vapor deposited in a vacuum of $2 \cdot 10^{-6}$ torr at a rate of 0.2 nm/minute.

If ITO is used as a hole-collecting electrode, aluminum, which is vapor deposited onto the electrically insulating transition layer, is used as an electron-collecting electrode. The electric insulation properties of the transition layer obviously prevent influences which hinder the crossing of the charge carrier from being effective, particularly in the transition region from the photoactive layer to the transition layer.

In a further embodiment of the invention, one or more of the layers may be treated with plasma prior to depositing the next layer. It is particularly advantageous that prior to the deposition of the PEDOT:PSS layer the anode material is subjected to a mild plasma treatment.

As an alternative to PEDOT:PSS a crosslinkable hole-transport material based on triarylamines as referenced in Macromol. Rapid Commun. 20, 224-228 (1999) can be used. In addition to the triarylamine material the layer can also include an electron acceptor to improve electron transport. Such compounds are disclosed in US 2004/0004433. Preferably, the electron acceptor material is soluble in one or more organic solvents. Typically, the electron acceptor material is present in the range for 0.5 to 20% by weight of the triarylamine material.

The photovoltaic (PV) device can also consist of multiple junction solar cells that are processed on top of each other in order to absorb more of the solar spectrum. Such structures are, for example, described in App. Phys. Let. 90, 143512 (2007), Adv. Funct. Mater. 16, 1897-1903 (2006) and WO2004/112161.

A so called 'tandem solar cell' comprise in this order:
(a) a cathode (electrode),
(b) optionally a transition layer, such as an alkali halogenide, especially lithium fluoride,
(c) a photoactive layer,
(d) optionally a smoothing layer,
(e) a middle electrode (such as Au, Al, ZnO, $TiO_2$ etc.)
(f) optionally an extra electrode to match the energy level,
(g) optionally a transition layer, such as an alkali halogenide, especially lithium fluoride,
(h) a photoactive layer,
(i) optionally a smoothing layer,
(j) an anode (electrode),
(k) a substrate.

The PV device can also be processed on a fiber as described, for example, in US20070079867 and US 20060013549.

Due to their excellent self-organising properties the materials or films comprising the compounds of the formula I can also be used alone or together with other materials in or as alignment layers in LCD or OLED devices, as described for example in US200310021913.

The following examples are included for illustrative purposes only and do not limit the scope of the claims. Unless otherwise stated, all parts and percentages are by weight.

Abbreviations: m.p. melting point; In the reported NMR spectra the following abbreviations are used: d: dublet, dd: dublet of dublet, m: multiplet, s: singulet, t: triplet, quint: quintet, sext: sextet

EXAMPLES

Example 1

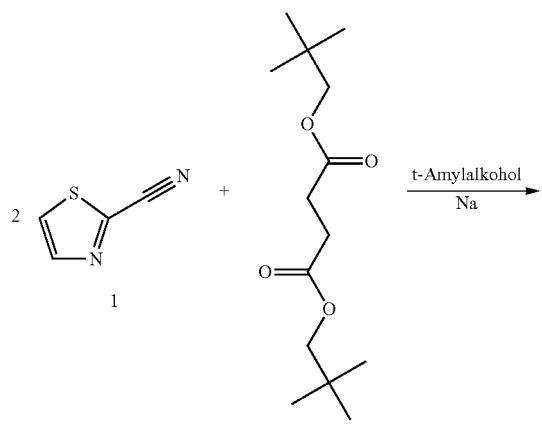

a) A mixture of 5 mg iron trichloride ($FeCl_3$), 2.6 g of sodium and 100 ml of t-amylalcohol is heated to 110° C. for 20 minutes before a mixture of 5.0 g of the thiazole-2-nitrile of the formula 1 and 8.25 g of di-tert-amyl succinate of the formula 2 is added drop wise. The reaction mixture is stirred at 110° C. for 3 hours before it is poured onto 8.15 g acetic acid in a water-methanol mixture (200 ml/100 ml). Büchner filtration and exhaustive washing with methanol affords 5.2 g of the desired 1,4-diketopyrrolo[3,4-c]pyrrole (DPP) derivative of the formula 3 as dark blue powder: ESI-MS m/z (% int.): 303.13 ([M+H]+, 100%).

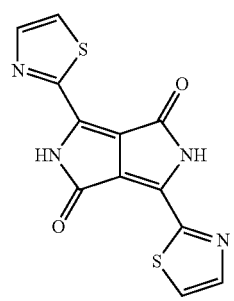

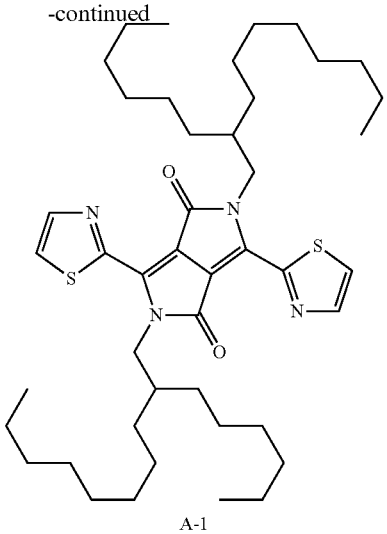

b) A solution of 4 g of the 1,4-diketopyrrolo[3,4-c]pyrrole (DPP) derivative of the formula 3, 2.9 g of KOH in 3 ml of water and 18.5 g of 1-bromo-2-hexyl-decyl in 50 ml of N-methyl-pyrrolidone (NMP) is heated to 140° C. for 6 h. The mixture is washed with water and extracted with dichloromethane. Purification is achieved by column chromatography over silica gel and precipitation out of chloroform/methanol which affords 0.4 g of the desired DPP compound A-1 as blue solid. ESI-MS m/z (% int.): 751.93 ([M+H]+, 100%).

Example 2

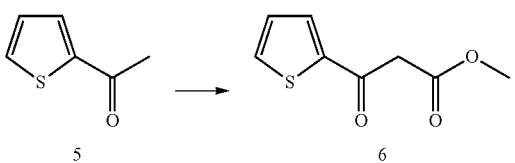

a) 554.6 g of potassium tert-butoxide, 424.2 g of dimethyl carbonate and 3 L of anhydrous toluene are heated to 100° C. with stirring. 300 g of 1-acetyl thiophene 5 is added drop by drop during three hours and stirred at 100° C. for 15 hours. The reaction mixture is allowed to cool to room temperature and poured onto 4 L of ice. The water layer is separated and two times extracted with 200 ml of ethyl acetate. The organic layers are combined and dried over sodium sulfate, filtered, evaporated and dried, giving 363.7 g of 6. The crude product is used for the next reaction step without further purification.

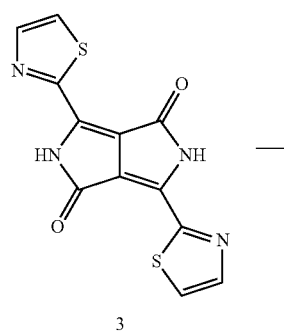

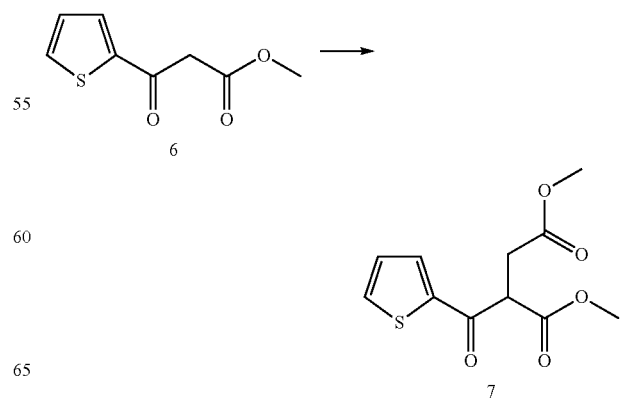

b) 363.7 g of 6, 322.7 g of methyl bromooacetate, 288.7 g potassium carbonate, 1100 ml of acetone and 750 ml of 1,2-dimethoxyethane are placed in a vessel. The mixture is stirred at 80° C. for 20 hours. After the mixture has cooled down to room temperature, it is filtered and dried. 460 g of 7 are obtained. The crude product is used for the next reaction step without further purification.

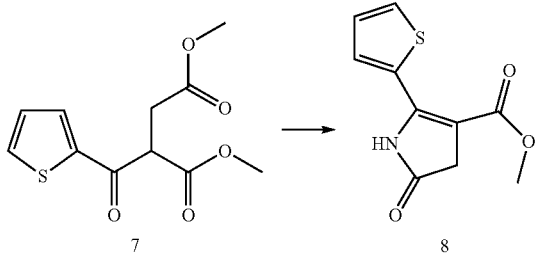 [SMILES: COC(=O)CC(C(=O)OC)C(=O)c1cccs1 ; COC(=O)C1=C(c2cccs2)NC(=O)C1]

c) 218 g of 7, 643 g of ammonium acetate and 680 ml of acetic acid are stirred at 115° C. for 3 hours. After the reaction mixture has cooled down to room temperature, it is poured into 3 L of acetone. The produced solid is separated and washed with methanol and dried. 99.6 g of 8 are obtained.

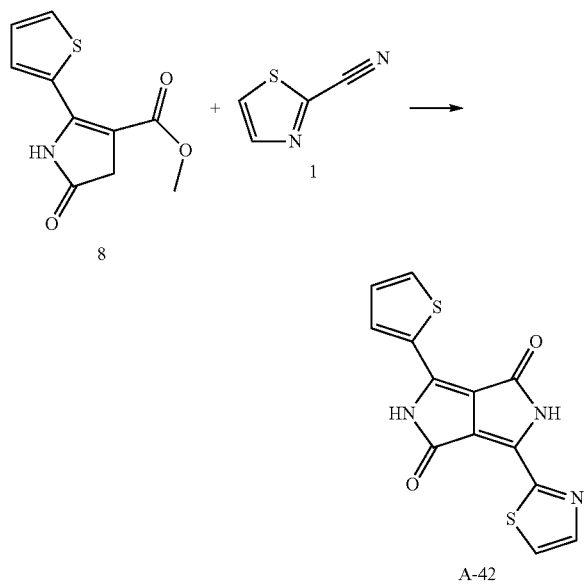

d) a) A mixture of 5 mg iron trichloride (FeCl$_3$), 2 g of sodium and 40 ml of t-amylalcohol is heated to 110° C. for 20 minutes before a mixture of 3.9 g of the thiazole-2-nitrile of the formula 1 and 7.82 g of 8 is added portion-wise. The reaction mixture is stirred at 110° C. for 3 hours before it is poured onto 6.3 g acetic acid in a water-methanol mixture (100 ml/100 ml). Büchner filtration and exhaustive washing with methanol affords 4.5 g of the desired 1,4-diketopyrrolo[3,4-c]pyrrole (DPP) derivative of the formula A-42 as dark blue powder; ESI-MS m/z (% int.): 302.15 ([M+H]+, 100%).

Example 3

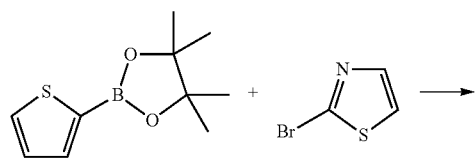

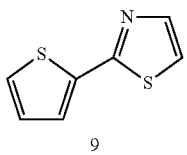

a) In a three neck-flask, 83.6 g of potassium phosphate (K$_3$PO$_4$) dissolved in 110 ml of water (previously degassed) is added to a degassed solution of 20 g 2-thiophene-boronic acid, 22 g 2-bromo-thiazole, 2.26 g of tri-tert-butylphosphonium tetrafluoroborate ((t-Bu)$_3$P*HBF$_4$) and 3.57 g of tris(dibenzylideneacetone)dipalladium (0) (Pd$_2$(dba)$_3$) in 350 ml of tetrahydrofuran. The reaction mixture is heated at reflux temperature over night. The reaction mixture is quenched with water and extracted with ethylacetate. The organic layers are dried with sodium sulfate and evaporated under reduced pressure The crude product is purified by flash column chromatography in dichloromethane. 6.9 g of 2-thiophen-2-yl-thiazole (9) are obtained. $^1$H (CDCl$_3$): 7.7, 1H, d; 7.5, 1H, d; 7.4, 1H, d; 7.3, 1H, d; 7.1, 1H, dd. $^{13}$C (CDCL$_3$) 170.2 Cq, 162.0 Cq, 143.2 CH, 127.9 CH, 127.6 CH, 126.6 CH, 118.1 CH.

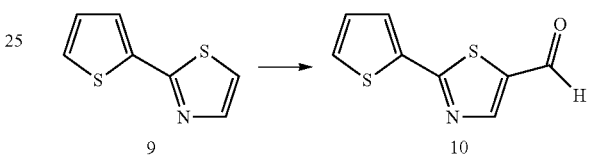

b) In a 100 ml three neck-flask, the LDA-solution is prepared as following: 5.12 g diisopropylamine in 30 ml THF are cooled to –78° C., then 20.24 ml buthyllithium are added over 10 minutes. The reaction mixture is stirred at –78° C. for five minutes and then warmed to 0° C. and stirred for 15 minutes. In a 250 ml three neck-flask 7.694 g 2-thiophen-2-yl-thiazole in 60 ml THF are cooled to –40° C., then the LDA solution is added over one 1 hour at –40° C. and stirred for an additional hour. 10 g of dimethylformamide are added within 5 minutes and stirred for additional 10 minutes at –40° C. The reaction mixture is warmed to room temperature and stirred overnight. The reaction mixture is quenched with 250 ml water and extracted with 150 ml ethylacetate. The organic layers are dried with sodium sulfate and evaporated under reduced pressure The crude product is purified by flash column chromatography using a gradient of ethylacetate and hexane. 7.1 g of 2-thiophen-2-yl-thiazole-5-carbaldehyde (10) are obtained. $^1$H (CDCl$_3$): 10.0, 1H, s, CHO, 8.4, 1H, d; 7.7, 1H, d; 7.6, 1H, d; 7.2, 1H, dd.

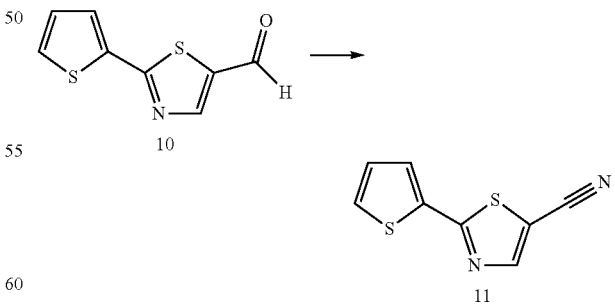

c) 6.6 g 2-thiophen-2-yl-thiazole-5-carbaldehyde, 2.8 g hydroxylamine hydrochloride in 45 ml dimethylamide are heated to 150° C. for 2 hours. The solvent is removed under reduced pressure. The crude product is purified by flash column chromatography in ethylacetate:hexane=1:5. 4.7 g of 2-thiophen-2-yl-thiazole-5-carbonitrile (11) are obtained. $^1$H (CDCl$_3$): 8.2, 1H, d; 7.6, 1H, d; 7.5, 1H, d; 7.1, 1H, dd. $^{13}$C (CDCL$_3$) 166.8 Cq, 152.5 Cq, 135.6 CH, 130.7 CH, 129.0 CH, 128.5 CH, 111.9 Cq 104.4 Cq.

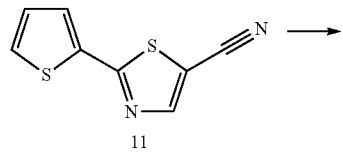

11

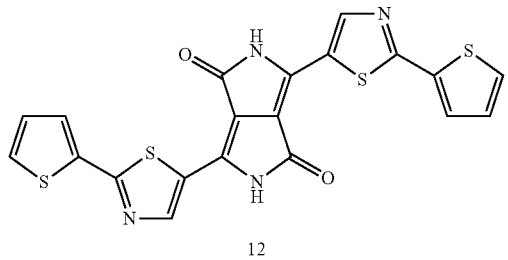

12 d) The DPP compound 12 is obtained in analogy to example 1a. MALDI-TOF (pos): 467.05 MH$^+$

12 ⟶

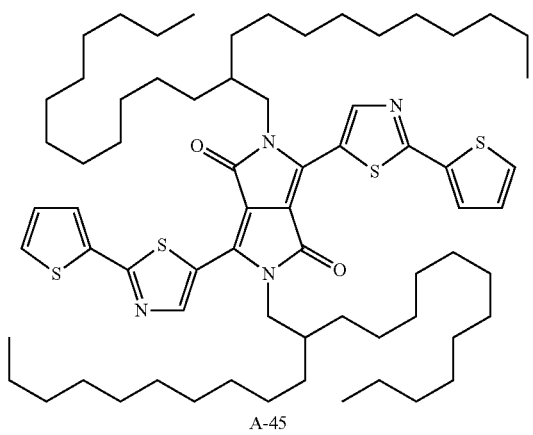

A-45 e) in a 25 ml three neck-flask, 0.28 g 12 and 0.2 g potassium carbonate in 13 ml dimethylformamide are heated to 110° C. and stirred for 1 hour. To this reaction mixture 0.84 g 2-decyl-tetradecyliodide are added within 10 minutes and stirred for 21 hours at 110° C. The solvent is removed under reduced pressure. The residue is dissolved in 25 ml of chloroform and extracted with 25 ml water. The combined organic layers are washed with water, dried over sodium sulfate and removed under reduced pressure. The crude product is further purified over flash column chromatography in chloroform. 0.14 g of the desired product A-45 are obtained. $^1$H (CDCl$_3$): 9.3, 2H, d; 7.7, 2H, d; 7.6, 2H, d; 7.2, 2H, dd; 4.0, 4H, d; 1.7, 2H, m, 1.3-1.1, 80H, m; 0.9, 12H, m.

Example 4

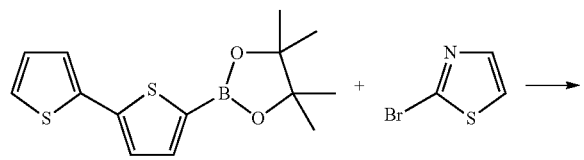

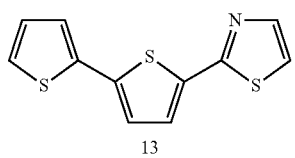

13 a) 2-[2,2']bithiophenyl-5-yl-thiazole (13) is obtained in analogy to example 3a) using 5-(4,4,5,5-tetramethyl-1,3,2-dioxaborolan-2-yl)-2,2'-bithiophene and 2-bromo-thiazole.

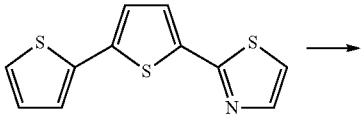

13

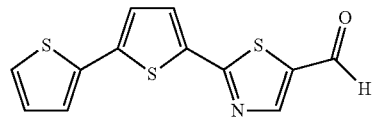

14 b) 2-[2,2']bithiophenyl-5-yl-thiazole-5-carbaldehyde (14) is obtained in analogy to example 3b).

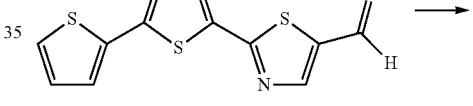

14

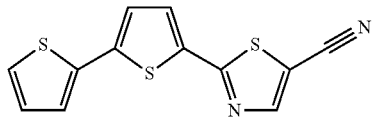

15 c) 2-[2,2']bithiophenyl-5-yl-thiazole-5-carbonitrile (15) is obtained in analogy to example 3c).

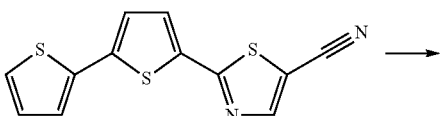

15

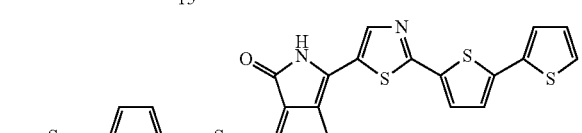

16 d) The DPP compound 16 is obtained in analogy to example 1a).

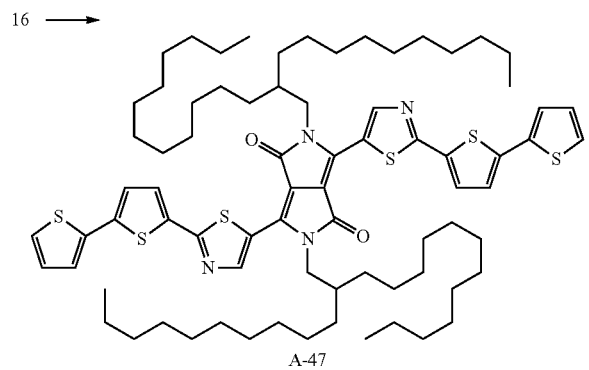

e) Compound A-47 is obtained in analogy to example 3e).

Example 5

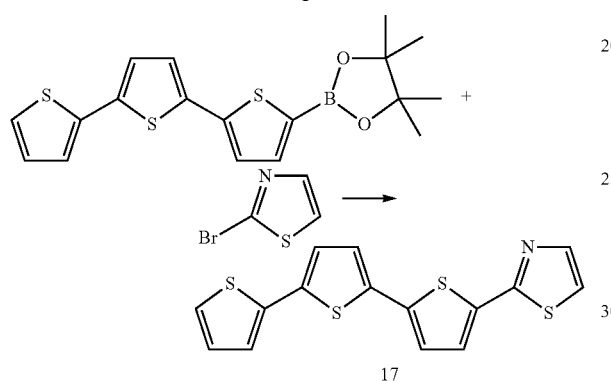

a) 2-[2,2':5',2"]terthiophene-5-yl-thiazole (17) is obtained in analogy to example 3a).

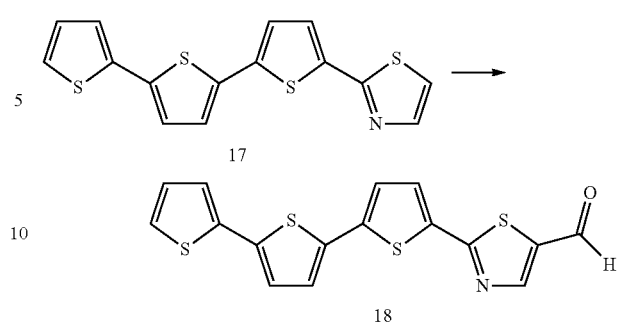

b) 2-[2,2':5',2"]terthiophene-5-yl-thiazole-5-carbaldehyde (18) is obtained in analogy to example 3b).

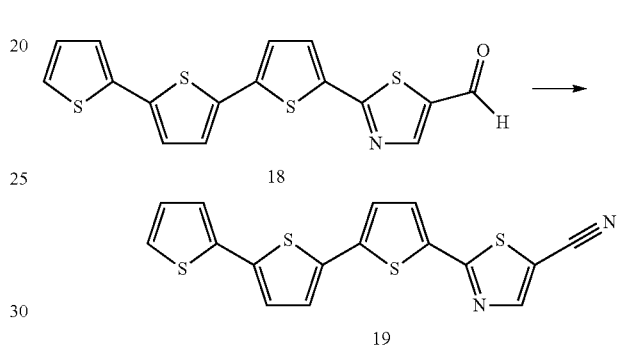

c) 2-[2,2':5',2"]terthiophene-5-yl-thiazole-5-carbonitrile (18) is obtained in analogy to example 3c).

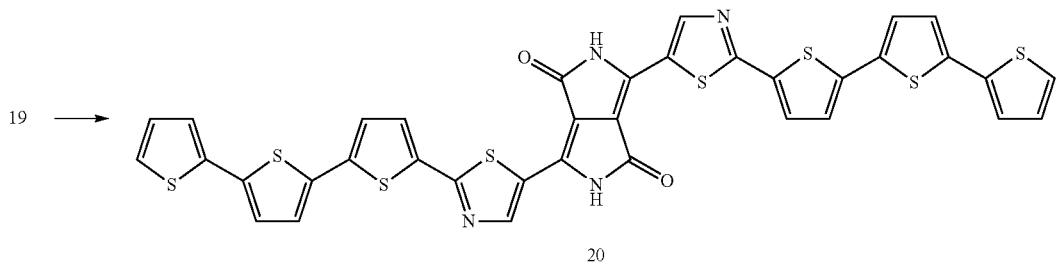 [SMILES: O=C1NC(c2cnc(-c3ccc(-c4ccc(-c5cccs5)s4)s3)s2)=C2C(=O)NC(c3cnc(-c4ccc(-c5ccc(-c6cccs6)s5)s4)s3)=C12]

d) Compound 20 is obtained in analogy to example 1a).

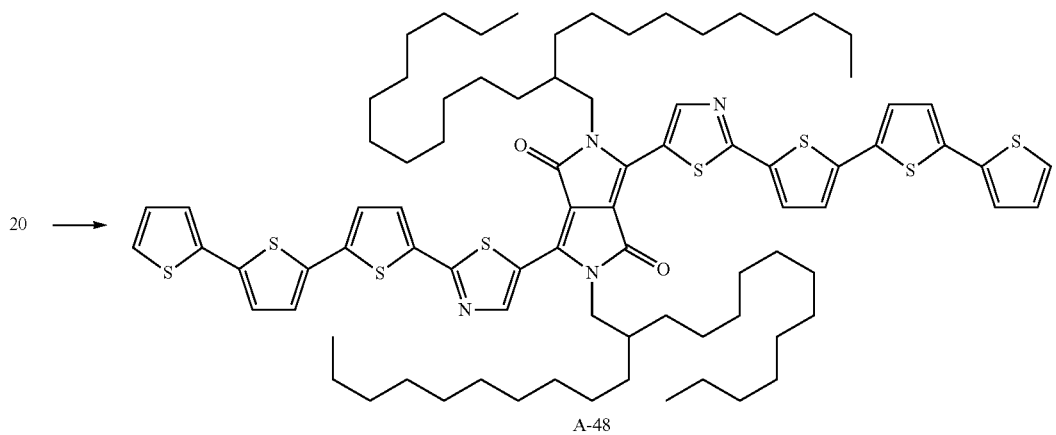

e) Compound A-48 is obtained in analogy to example 3e).

The invention claimed is:
1. A compound of formula (I)

$$R^4 \!-\!\!\left[\!-\!Ar^8\!-\!\right]_h\!\!\left[\!-\!Ar^6\!-\!\right]_f\!\!\left[\!-\!Ar^5\!-\!\right]_e\!\!\left[\!-\!Ar^4\!-\!\right]_d\!-$$

[structure of formula (I): a pyrrolopyrrole-1,4-dione core with $R^1$ on one N, $R^2$ on the other N, and a chain $-[Ar^1]_a-[Ar^2]_b-[Ar^3]_c-[Ar^7]_g-R^3$]

wherein $R^1$ and $R^2$ are independently selected from the group consisting of:
hydrogen;
a $C_1$-$C_{100}$ alkyl group;
—COOR$^{103}$;
a $C_1$-$C_{100}$ alkyl group that is substituted by one or more halogen atoms, a hydroxyl group, a nitro group, —CN, or a $C_6$-$C_{24}$ aryl group;
a $C_1$-$C_{100}$ alkyl group that is interrupted by —O—, —COO—, —OCO—, or —S—;
a $C_7$-$C_{100}$ arylalkyl group;
a carbamoyl group;
a $C_5$-$C_{12}$ cycloalkyl, which can be substituted one to three times with at least one selected from the group consisting of $C_1$-$C_8$ alkyl and $C_1$-$C_8$ alkoxy;
a $C_6$-$C_{24}$ aryl group,
and pentafluorophenyl,
$R^{103}$ is:
H;
$C_6$-$C_{24}$ aryl;
$C_6$-$C_{24}$ aryl substituted by $C_1$-$C_{25}$ alkyl or $C_1$-$C_{25}$ alkoxy;
$C_1$-$C_{50}$ alkyl;
or $C_1$-$C_{50}$ alkyl interrupted by —O—;
a is 1 and d is 1,
$Ar^1$ and $Ar^4$ are each independently a bivalent group of formula (II)

[structure of formula (II): thiophene-like ring with S and $X^3$—$X^4$]

wherein one of $X^3$ and $X^4$ is N, and the other of $X^3$ and $X^4$ is CR$^{100}$ and
$R^{100}$ is hydrogen or $C_1$-$C_{25}$alkyl,
b, c, e, f, g and h are each independently 0, 1, 2 or 3,
$Ar^2$, $Ar^3$, $Ar^5$, $Ar^6$, $Ar^7$ and $Ar^8$ are as described for $Ar^1$ or are each independently

[structure of formula (IV): thiophene with $R^6$ and $R^7$]

[structure of formula (V): phenyl with $(R^5)_p$]

[structure of formula (VI): dithienyl fused ring with $R^9$, X, $R^{12}$]

[structure of formula (VII): thieno-thiophene with $R^{13}$, $R^{14}$]

[structure of formula (VIII): thieno-thiophene with $R^{15}$, $R^{16}$]

[structure of formula (IX): benzodithiophene with $R^{17}$, $R^{18}$, $R^{19}$, $R^{21}$]

[structure of formula (Xa): benzothiadiazole]

[structure of formula (Xb): dibenzofuran/fluorene-type with X]

wherein X is SiR$^{60}$R$^{61}$, NR$^{62}$, CR$^{10}$R$^{11}$, S, or O,
p is 0, 1, or 2,
$R^5$ is an aliphatic hydrocarbon group comprising up to 25 carbon atoms, $C_1$-$C_{25}$ alkoxy, or two vicinal groups $R^5$ together represent alkylene or alkenylene comprising up to 7 carbon atoms, where, when p is 2, two $R^5$ groups are independent,
$R^6$, $R^7$, $R^9$, $R^{12}$, $R^{13}$, $R^{14}$, $R^{15}$, $R^{16}$, $R^{17}$, $R^{18}$, $R^{19}$, and $R^{21}$ are each independently hydrogen, $C_1$-$C_{25}$alkyl, $C_1$-$C_{25}$alkoxy, $C_6$-$C_{24}$aryl, $C_7$-$C_{25}$aralkyl, or heteroaryl, or $R^6$ and $R^7$ together represent alkylene or alkenylene comprising up to 25 carbon atoms and that are both optionally bonded via at least one selected from the group consisting of oxygen and sulfur to the thienyl residue,
$R^{10}$ and $R^{11}$ are each independently selected from the group consisting of hydrogen, $C_1$-$C_{25}$ alkyl, $C_7$-$C_{25}$ aralkyl, $C_6$-$C_{24}$ aryl, and heteroaryl, or $R^{10}$ and $R^{11}$ together represent oxo or form a five or six membered ring, which is unsubstituted or substituted by
a) an aliphatic hydrocarbon group comprising up to 18 carbon atoms, b) $C_1$-$C_{18}$ alkoxy or $C_2$-$C_{18}$ alkylenedioxy, in both of which at least one carbon atom that is not adjacent to oxygen is optionally replaced by oxygen, or
c) $C_6$-$C_{24}$ aryl, $C_7$-$C_{25}$ aralkyl, heteroaryl, $C_3$-$C_{12}$ cycloalkyl or $C_4$-$C_{12}$ cycloalkyl-alkyl;

wherein $R^{60}$ and $R^{61}$ are each independently hydrogen, $C_1$-$C_{25}$ alkyl, or phenyl;

$R^{62}$ is:
hydrogen;
$C_7$-$C_{25}$ arylalkyl;
$C_6$-$C_{24}$ aryl;
$C_6$-$C_{24}$ aryl substituted by $C_1$-$C_{25}$ alkyl, $C_1$-$C_{25}$ perfluoroalkyl, or $C_1$-$C_{25}$ alkoxy;
$C_1$-$C_{25}$ alkyl;
$C_1$-$C_{25}$ alkyl interrupted by —O—, or —S—; or
—COOR$^{103}$;

wherein $R^3$ and $R^4$ are each independently:
hydrogen;
an aliphatic hydrocarbon group comprising up to 25 carbon atoms, alkoxy or alkenyloxy comprising up to 25 carbon atoms;
a halogen;
a cycloaliphatic, cycloaliphatic-aliphatic, aromatic, aromatic-aliphatic, heteroaromatic or heteroaromatic-aliphatic group comprising up to 25 carbon atoms;

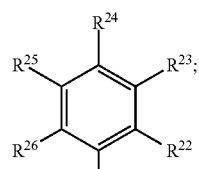   (XI)

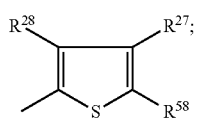   (XII)

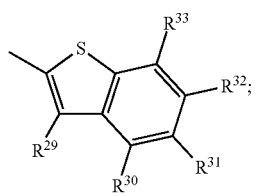   (XIII)

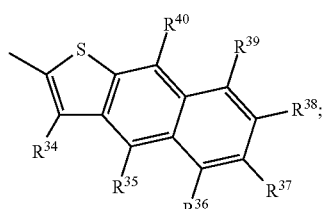   (XIV)

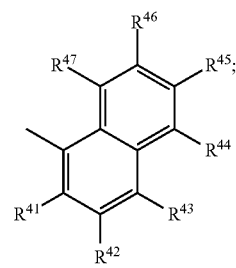   (XV)

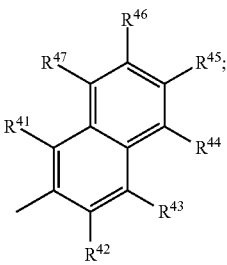   (XVI)

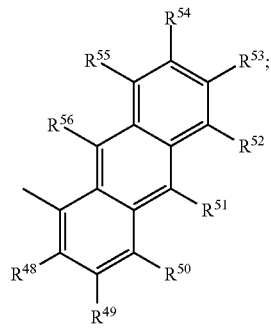   (XVII)

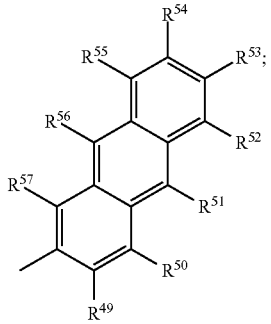   (XVIII)

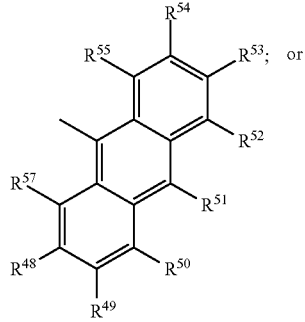   (XIX)

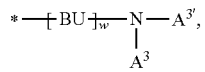   (XX)

wherein w is 0 or 1,
BU is a bridging unit, and
$A^3$ and $A^{3'}$ are each independently a $C_6$-$C_{24}$ aryl group, or a $C_2$-$C_{26}$ heteroaryl group, which are optionally substituted,
and wherein either
$R^{22}$ to $R^{58}$ are each independently
hydrogen,
an aliphatic hydrocarbon group comprising up to 25 carbon atoms,
an alkoxy comprising up to 25 carbon atoms,
an alkenyloxy comprising up to 25 carbon atoms,
a halogen, or a cycloaliphatic, cycloaliphatic-aliphatic, aromatic, aromatic-aliphatic, heteroaromatic or heteroaromatic-aliphatic group comprising up to 25 carbon atoms, or $R^{27}$ and $R^{28}$, or $R^{27}$ and $R^{58}$ together represent alkylene or alkenylene comprising up to 25 carbon atoms and that are both optionally bonded via at least one selected from the group consisting of oxygen and sulfur to the thienyl residue.

2. The compound of claim 1, wherein $Ar^2$, $Ar^3$, $Ar^5$, $Ar^6$, $Ar^7$ and $Ar^8$ are each independently selected from the group consisting of

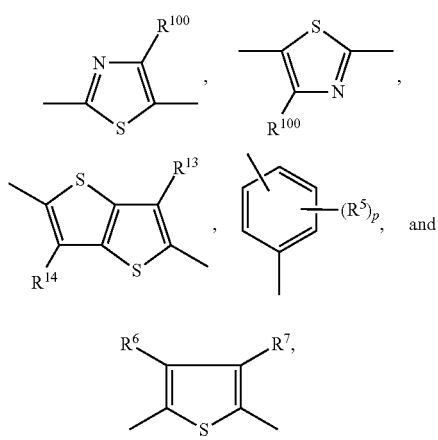

(IV)

wherein $R^{100}$ is hydrogen or $C_1$-$C_{25}$ alkyl;

$R^5$ is $C_1$-$C_{25}$ alkyl;

$R^6$, $R^7$, $R^{13}$ and $R^{14}$ are each independently hydrogen, $C_7$-$C_{25}$ aralkyl, or $C_1$-$C_{25}$ alkyl; and p is 0, 1, or 2.

3. The compound of claim 1, wherein:

$R^3$ and $R^4$ are each independently hydrogen, an aliphatic hydrocarbon group comprising up to 25 carbon atoms, or a group of formula (XII)

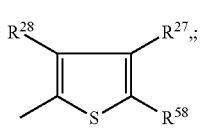

(XX)

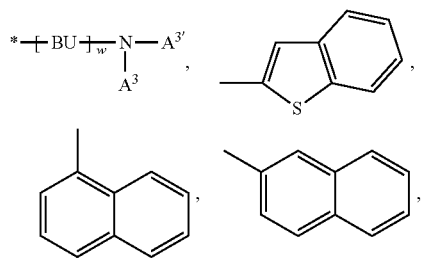

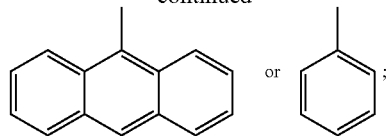

$R^{27}$ and $R^{28}$ are each independently hydrogen, —$CR^{203}R^{204}$—$(CH_2)_u$—Ar, or a $C_1$-$C_{25}$ alkyl group;

$R^{58}$ is —$CR^{203}R^{204}$—$(CH_2)_u$—Ar, or a $C_1$-$C_{25}$ alkyl group;

$R^{203}$ and $R^{204}$ are each independently hydrogen or $C_1$-$C_4$ alkyl;

Ar is selected from the group consisting of phenyl, 1-napthyl, and 2-naphthyl, each of which are optionally substituted with one to three groups independently selected from the group consisting of $C_1$-$C_8$ alkyl and $C_1$-$C_8$ alkoxy;

u is 0, 1, 2, 3 or 4;

BU is

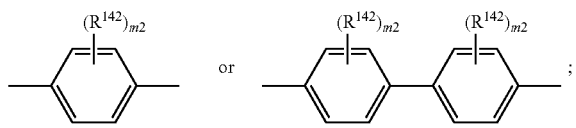

$R^{142}$ is $C_1$-$C_{18}$ alkyl, $C_1$-$C_{18}$ alkyl interrupted by O, or $C_1$-$C_{18}$ alkoxy;

m2 can be the same or different at each occurrence and is 0 or 1;

$A^3$ and $A^{3'}$ are independently of each other

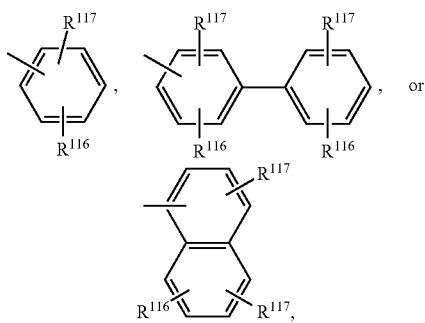

and $R^{116}$ and $R^{117'}$ are independently of each other H, $C_1$-$C_{18}$ alkyl, or $C_1$-$C_{18}$ alkyl interrupted by O.

4. The compound of claim 1, wherein $R^1$ and $R^2$ are each independently:

$C_1$-$C_{100}$ alkyl;

$C_5$-$C_{12}$ cycloalkyl optionally substituted with one to three groups independently selected from the group consisting of $C_1$-$C_8$ alkyl and $C_1$-$C_8$ alkoxy;

phenyl or 1- or 2-naphthyl optionally substituted with one to three groups independently selected from the group consisting of $C_1$-$C_8$ alkyl and $C_1$-$C_8$ alkoxy;

—$CR^{203}R^{204}$—$(CH_2)_u$—Ar;

wherein $R^{203}$ and $R^{204}$ are each independently hydrogen or $C_1$-$C_4$ alkyl;

Ar is selected from the group consisting of phenyl, 1-naphthyl, and 2-naphthyl, each of which are optionally substituted with one to three groups independently selected from the group consisting of $C_1$-$C_8$ alkyl and $C_1$-$C_8$ alkoxy;

u is 0, 1, 2, or 3;

$R^3$ and $R^4$ are each independently hydrogen, a halogen, $C_1$-$C_{25}$ alkyl, $C_1$-$C_{25}$ alkoxy,

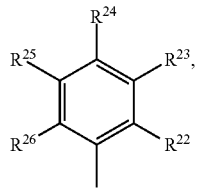
(XI)

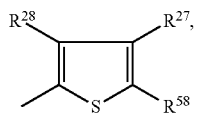
(XII)

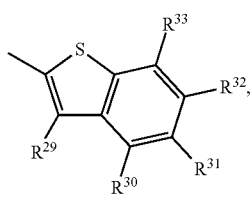
(XIII)

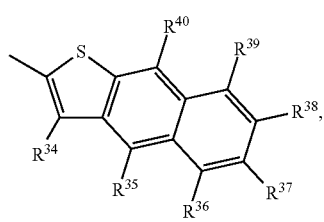
(XIV)

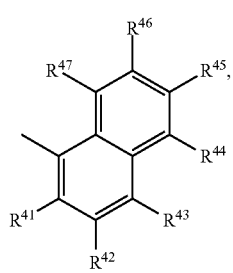
(XV)

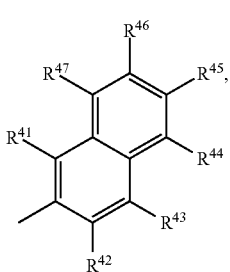
(XVI)

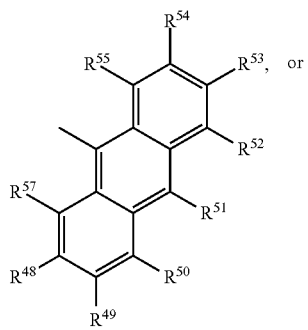
(XIX)

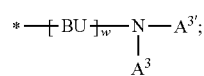
(XX)

wherein $R^{22}$ to $R^{26}$ and $R^{29}$ to $R^{58}$ are each independently hydrogen or an aliphatic hydrocarbon group comprising up to 25 carbon atoms, BU is

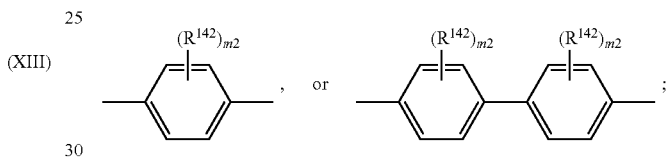

$R^{142}$ is $C_1$-$C_{18}$alkyl, $C_1$-$C_{18}$alkyl interrupted by O, or $C_1$-$C_{18}$alkoxy;

m2 can be the same or different at each occurrence and is 0 or 1;

$A^3$ and $A^{3'}$ are independently of each other

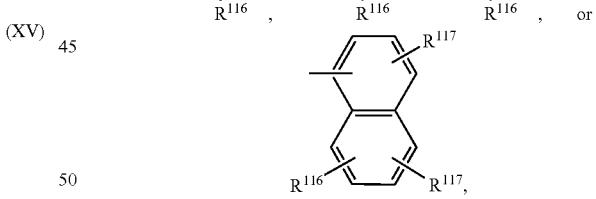

and $R^{116}$ and $R^{117'}$ are independently of each other H, $C_1$-$C_{18}$ alkyl, or $C_1$-$C_{18}$ alkyl interrupted by O;

$R^{27}$ and $R^{28}$ are each independently hydrogen, $C_1$-$C_{25}$ alkyl, or $C_1$-$C_{18}$ alkoxy, or $R^{27}$ and $R^{28}$ together or $R^{27}$ and $R^{58}$ together represent alkylene or alkenylene comprising up to 25 carbon atoms and both optionally bonded via at least one selected from the group consisting of oxygen and sulfur to the thienyl residue.

5. The compound of claim 1,
wherein $R^1$ and $R^2$ are each independently:
$C_1$-$C_{100}$ alkyl;
$C_5$-$C_{12}$ cycloalkyl optionally substituted with one to three groups selected from the group consisting of $C_1$-$C_8$ alkyl and $C_1$-$C_8$ alkoxy;

phenyl, 1-naphthyl, or 2-naphthyl, optionally substituted with one to three groups selected from the group consisting of $C_1$-$C_8$ alkyl and $C_1$-$C_8$ alkoxy; or
—$CR^{203}R^{204}$—$(CH_2)_u$—Ar,
wherein $R^{203}$ and $R^{204}$ are each independently hydrogen or $C_1$-$C_4$ alkyl,
Ar is phenyl, 1-naphthyl, or 2-naphthyl, optionally substituted with one to three groups selected from the group consisting of $C_1$-$C_8$ alkyl and $C_1$-$C_8$ alkoxy,
u stands for 0, 1, 2, or 3,
a and d are 1,
b, c, e, f, g and h are each independently 0, 1, 2, or 3,
$Ar^2$, $Ar^3$, $Ar^5$, $Ar^6$, $Ar^7$ and $Ar^8$ are each independently a bivalent group of the formula

(IV)

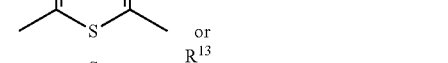

wherein $R^6$, $R^7$, $R^{13}$ and $R^{14}$ are each independently hydrogen or $C_1$-$C_{25}$ alkyl,
$R^3$ and $R^4$ are each independently hydrogen, an aliphatic hydrocarbon group comprising up to 25 carbon atoms, or a group of formula (XII)

(XII)

$R^{58}$ is hydrogen or an aliphatic hydrocarbon group comprising up to 25 carbon atoms, and
$R^{27}$ and $R^{28}$ are each independently hydrogen or $C_1$-$C_{25}$ alkyl.

6. The compound of claim 1, wherein
$Ar^2$, $Ar^3$, $Ar^5$, $Ar^6$, $Ar^7$ and $Ar^8$ are each independently a bivalent group of formula

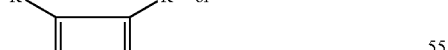
(IV)

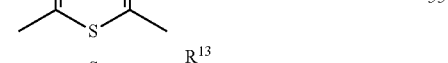

$R^6$, $R^7$, $R^{13}$ and $R^{14}$ are each independently hydrogen, $C_1$-$C_{25}$alkyl, or $C_7$-$C_{25}$aralkyl,
$R^3$ and $R^4$ are each independently hydrogen, an aliphatic hydrocarbon group comprising up to 25 carbon atoms,

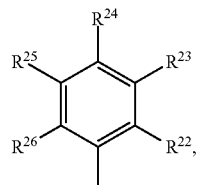
(XI)

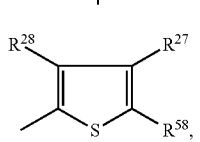
(XII)

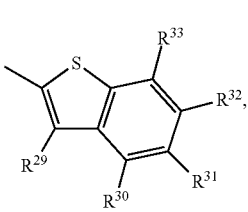
(XIII)

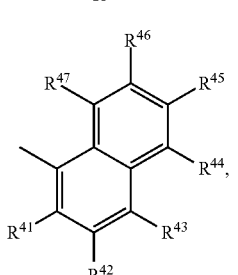
(XV)

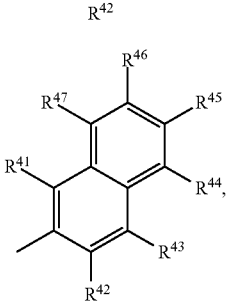
(XVI)

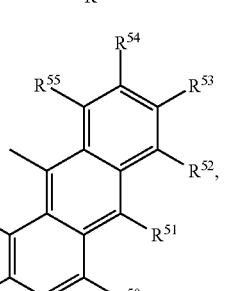
(XIX)

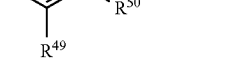

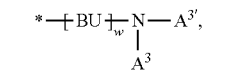
(XX)

$R^{22}$ to $R^{26}$, $R^{29}$ to $R^{33}$, $R^{41}$ to $R^{55}$, $R^{57}$, $R^{58}$ are each independently hydrogen, an aliphatic hydrocarbon group comprising up to 25 carbon atoms, aryl, alkoxy comprising up to 18 carbon atoms, or halogen, or two groups $R^{22}$ to $R^{26}$, together represent alkylene or alkenylene comprising up to 8 carbon atoms, thereby forming a ring, BU is

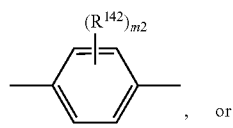, or

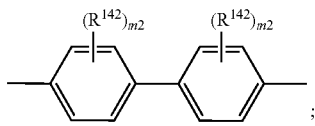;

$R^{142}$ is $C_1$-$C_{18}$alkyl, $C_1$-$C_{18}$alkyl interrupted by O, or $C_1$-$C_{18}$alkoxy;

m2 can be the same or different at each occurrence and is 0 or 1;

$A^3$ and $A^{3'}$ are independently of each other

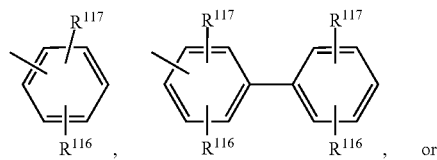, or

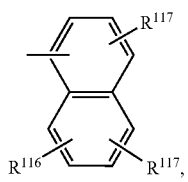, and $R^{116}$ and $R^{117'}$ are independently of each other H, $C_1$-$C_{18}$ alkyl, or $C_1$-$C_{18}$ alkyl interrupted by O;

$R^{27}$ and $R^{28}$ are each independently hydrogen, $C_1$-$C_{25}$alkyl, or $C_7$-$C_{25}$aralkyl, or $R^{27}$ and $R^{28}$ together represent alkylene or alkenylene comprising up to 25 carbon atoms and that are both optionally bonded via at least one selected from the group consisting of oxygen and sulfur to the thienyl residue.

7. The compound of claim 1,
wherein $R^1$ and $R^2$ are the same and
side chains of the formulae

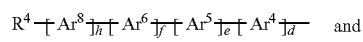 and

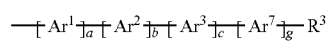

are identical to each other.

8. An organic semiconductor material, layer or component, comprising the compound of claim 1.

9. A semiconductor device comprising the compound of claim 1.

10. The semiconductor device of claim 9, wherein the device is selected from the group consisting of a diode, a photodiode, a sensor, an organic field effect transistor, a transistor for flexible displays, and a (heterojunction) solar cell.

11. A p-type transistor comprising the compound of claim 1.

12. The compound of claim 1, wherein at least one of $R^1$ and $R^2$ is a $C_6$-$C_{24}$ aryl group substituted with a group selected from the group consisting of phenyl, 1-naphthyl, or 2-naphthyl, each of which are optionally substituted with one to three groups selected from the group consisting of $C_1$-$C_8$ alkyl, $C_1$-$C_8$ thioalkoxy, and $C_1$-$C_8$ alkoxy.

13. A compound of claim 1, wherein $Ar^1$ is a bivalent group of the formula II and $Ar^4$ is a different bivalent group of the formula II.

14. The compound of claim 3,
wherein at least one of $R^3$ and $R^4$ is

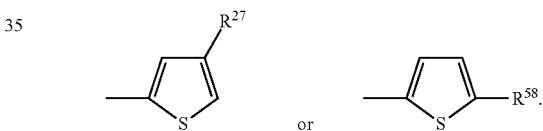

15. The compound of claim 1, having a formula selected from the group consisting of

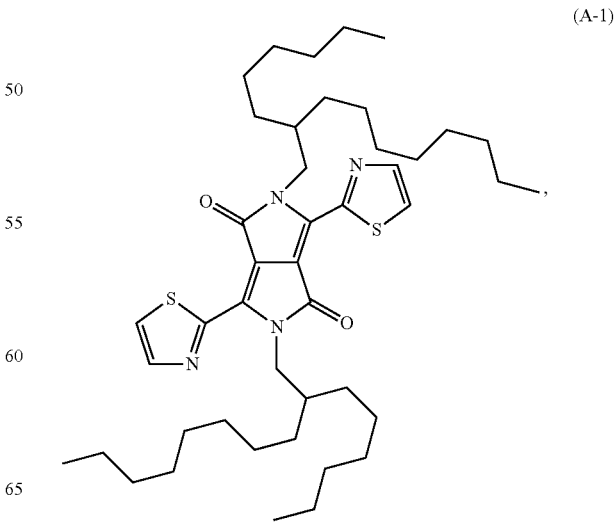 (A-1)

-continued
(A-2)
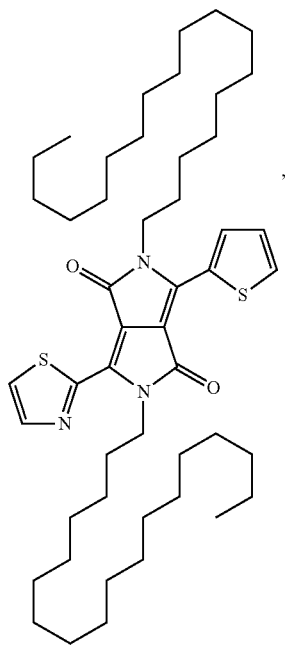
(A-3)
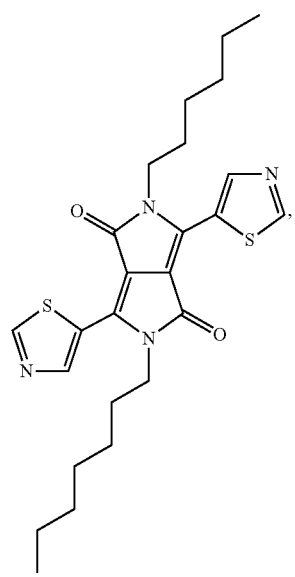
-continued
(A-4)
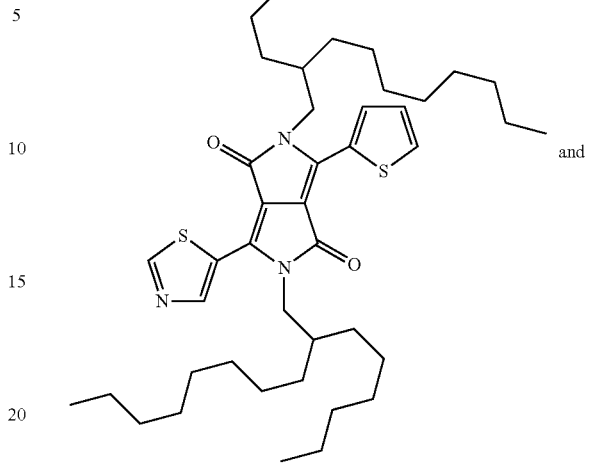
and
(A-5)
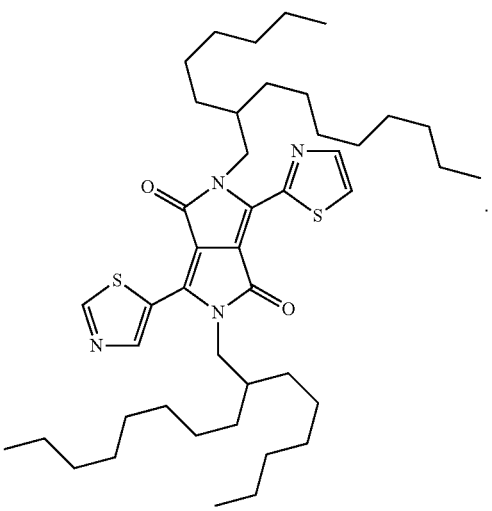
16. The semiconductor device of claim 9, wherein said device is a heterojunction solar cell.
* * * * *